(12) United States Patent
Knudsen et al.

(10) Patent No.: US 10,835,531 B1
(45) Date of Patent: Nov. 17, 2020

(54) METHODS FOR PREDICTING DRUG RESPONSIVENESS IN CANCER PATIENTS

(71) Applicant: Oncology Venture ApS, Høsholm (DK)

(72) Inventors: Steen Knudsen, Scottsdale, AZ (US); Peter Buhl Jensen, Farum (DK)

(73) Assignee: Oncology Venture ApS, Hørsholm (DK)

( * ) Notice: Subject to any disclaimer, the term of this patent is extended or adjusted under 35 U.S.C. 154(b) by 0 days.

(21) Appl. No.: 16/444,881

(22) Filed: Jun. 18, 2019

(51) Int. Cl.
| | | |
|---|---|---|
| *A61K 31/498* | (2006.01) | |
| *A61P 35/00* | (2006.01) | |
| *C12Q 1/6837* | (2018.01) | |
| *G16H 50/30* | (2018.01) | |
| *G01N 33/50* | (2006.01) | |
| *C12Q 1/6886* | (2018.01) | |
| *A61K 45/06* | (2006.01) | |

(52) U.S. Cl.
CPC ............ *A61K 31/498* (2013.01); *A61P 35/00* (2018.01); *C12Q 1/6837* (2013.01); *C12Q 1/6886* (2013.01); *G01N 33/5023* (2013.01); *G16H 50/30* (2018.01); *A61K 45/06* (2013.01); *G01N 2800/52* (2013.01)

(58) Field of Classification Search
None
See application file for complete search history.

(56) References Cited

PUBLICATIONS

Kim (Annal of Oncology 28 pages 1250-1259 2017).*
Abba et al. (BMC Genomics, 2005, 6:37, thirteen pages).*
Ross (Am J Clin Pathol 2005 vol. 124 Suppl 1 S29-S41).*

* cited by examiner

*Primary Examiner* — Amanda Haney
(74) *Attorney, Agent, or Firm* — Clark & Elbing LLP

(57) ABSTRACT

The present invention features methods, devices, and kits for detecting gene expression in a patient with a cancer or determining responsive of a patient with a cancer to a treatment, such as treatment with dovitinib or a pharmaceutically acceptable salt thereof. The invention further includes methods of treating a patient with a cancer by administering a treatment, e.g., treatment with dovitinib or a pharmaceutically acceptable salt thereof, in particular when the patient is determined to be responsive to the treatment based on the expression of the biomarkers described herein.

24 Claims, 3 Drawing Sheets
Specification includes a Sequence Listing.

SEQUENCE LISTING

<160> NUMBER OF SEQ ID NOS: 61

<210> SEQ ID NO 1
<211> LENGTH: 25
<212> TYPE: DNA
<213> ORGANISM: Homo sapiens

<400> SEQUENCE: 1
ggcagctatc ttacagacgc atgaa                                            25

<210> SEQ ID NO 2
<211> LENGTH: 25
<212> TYPE: DNA
<213> ORGANISM: Homo sapiens

<400> SEQUENCE: 2
gtccagcgaa tgacgtctgt ggcca                                            25

<210> SEQ ID NO 3
<211> LENGTH: 25
<212> TYPE: DNA
<213> ORGANISM: Homo sapiens

<400> SEQUENCE: 3
agtcaatgag tcgcttgtga attct                                            25

<210> SEQ ID NO 4
<211> LENGTH: 25
<212> TYPE: DNA
<213> ORGANISM: Homo sapiens

<400> SEQUENCE: 4
gagctgcgac aactggatga acatt                                            25

<210> SEQ ID NO 5
<211> LENGTH: 25
<212> TYPE: DNA
<213> ORGANISM: Homo sapiens

<400> SEQUENCE: 5
tattttggta cctgtgcttg ccaca                                            25

<210> SEQ ID NO 6
<211> LENGTH: 25
<212> TYPE: DNA
<213> ORGANISM: Homo sapiens

<400> SEQUENCE: 6
caacacagtt ttcttgtacc ctggg                                            25

<210> SEQ ID NO 7
<211> LENGTH: 25
<212> TYPE: DNA
<213> ORGANISM: Homo sapiens

```
<400> SEQUENCE: 7
tgaggtcaaa ttttatcttt tcact                                          25

<210> SEQ ID NO 8
<211> LENGTH: 25
<212> TYPE: DNA
<213> ORGANISM: Homo sapiens

<400> SEQUENCE: 8
tcattacttt ctgcttgacc ggaag                                          25

<210> SEQ ID NO 9
<211> LENGTH: 25
<212> TYPE: DNA
<213> ORGANISM: Homo sapiens

<400> SEQUENCE: 9
gagtggatct gcggtgaagc caagc                                          25

<210> SEQ ID NO 10
<211> LENGTH: 25
<212> TYPE: DNA
<213> ORGANISM: Homo sapiens

<400> SEQUENCE: 10
caataagtct ttctctccga aaccg                                          25

<210> SEQ ID NO 11
<211> LENGTH: 25
<212> TYPE: DNA
<213> ORGANISM: Homo sapiens

<400> SEQUENCE: 11
aatgcgggca tttaagtctg tccat                                          25

<210> SEQ ID NO 12
<211> LENGTH: 25
<212> TYPE: DNA
<213> ORGANISM: Homo sapiens

<400> SEQUENCE: 12
aaagccctgg tcgatgttgg agtgg                                          25

<210> SEQ ID NO 13
<211> LENGTH: 25
<212> TYPE: DNA
<213> ORGANISM: Homo sapiens

<400> SEQUENCE: 13
agaatgatgt ccccgttgta tgtat                                          25

<210> SEQ ID NO 14
<211> LENGTH: 25
<212> TYPE: DNA
<213> ORGANISM: Homo sapiens

<400> SEQUENCE: 14
tagaaagttt cttccactct ttgac                                          25

<210> SEQ ID NO 15
<211> LENGTH: 25
<212> TYPE: DNA
```

<213> ORGANISM: Homo sapiens

<400> SEQUENCE: 15
ggagacctgg ttgtgtgtgt gtgag                                    25

<210> SEQ ID NO 16
<211> LENGTH: 25
<212> TYPE: DNA
<213> ORGANISM: Homo sapiens

<400> SEQUENCE: 16
aagagccacc tgcaagatgg acacg                                    25

<210> SEQ ID NO 17
<211> LENGTH: 25
<212> TYPE: DNA
<213> ORGANISM: Homo sapiens

<400> SEQUENCE: 17
tgttcgtggt gagctacgcc aagga                                    25

<210> SEQ ID NO 18
<211> LENGTH: 25
<212> TYPE: DNA
<213> ORGANISM: Homo sapiens

<400> SEQUENCE: 18
gaattctaca tactaaatct ctctc                                    25

<210> SEQ ID NO 19
<211> LENGTH: 25
<212> TYPE: DNA
<213> ORGANISM: Homo sapiens

<400> SEQUENCE: 19
gatgagcaga cttctcggaa ttcat                                    25

<210> SEQ ID NO 20
<211> LENGTH: 25
<212> TYPE: DNA
<213> ORGANISM: Homo sapiens

<400> SEQUENCE: 20
aactaggaca ctaactgggt tccat                                    25

<210> SEQ ID NO 21
<211> LENGTH: 25
<212> TYPE: DNA
<213> ORGANISM: Homo sapiens

<400> SEQUENCE: 21
gtcccctgct tgaacactga agggc                                    25

<210> SEQ ID NO 22
<211> LENGTH: 25
<212> TYPE: DNA
<213> ORGANISM: Homo sapiens

<400> SEQUENCE: 22
aaatgttgct ctaatcagat tgctt                                    25

<210> SEQ ID NO 23
<211> LENGTH: 25

```
<212> TYPE: DNA
<213> ORGANISM: Homo sapiens

<400> SEQUENCE: 23
gacacctgtg tttcagcatt tggag                                   25

<210> SEQ ID NO 24
<211> LENGTH: 25
<212> TYPE: DNA
<213> ORGANISM: Homo sapiens

<400> SEQUENCE: 24
gacccatgag tggaggaact ttcag                                   25

<210> SEQ ID NO 25
<211> LENGTH: 25
<212> TYPE: DNA
<213> ORGANISM: Homo sapiens

<400> SEQUENCE: 25
atgacctgca gaaacagaac tgttc                                   25

<210> SEQ ID NO 26
<211> LENGTH: 25
<212> TYPE: DNA
<213> ORGANISM: Homo sapiens

<400> SEQUENCE: 26
gctggcacct tagttgcatg accac                                   25

<210> SEQ ID NO 27
<211> LENGTH: 25
<212> TYPE: DNA
<213> ORGANISM: Homo sapiens

<400> SEQUENCE: 27
tctgcccaac tgtcaacctt gacaa                                   25

<210> SEQ ID NO 28
<211> LENGTH: 25
<212> TYPE: DNA
<213> ORGANISM: Homo sapiens

<400> SEQUENCE: 28
gttataccat ttaaagctgg cacca                                   25

<210> SEQ ID NO 29
<211> LENGTH: 25
<212> TYPE: DNA
<213> ORGANISM: Homo sapiens

<400> SEQUENCE: 29
aaaggtatct gctgcatcga acttt                                   25

<210> SEQ ID NO 30
<211> LENGTH: 25
<212> TYPE: DNA
<213> ORGANISM: Homo sapiens

<400> SEQUENCE: 30
ttaagttcat tgacaccacc tccaa                                   25

<210> SEQ ID NO 31
```

```
<211> LENGTH: 25
<212> TYPE: DNA
<213> ORGANISM: Homo sapiens

<400> SEQUENCE: 31
ctgctctggt ggtgccgaag ggcaa                                              25

<210> SEQ ID NO 32
<211> LENGTH: 25
<212> TYPE: DNA
<213> ORGANISM: Homo sapiens

<400> SEQUENCE: 32
gattgactgt caggcatggc tttgt                                              25

<210> SEQ ID NO 33
<211> LENGTH: 25
<212> TYPE: DNA
<213> ORGANISM: Homo sapiens

<400> SEQUENCE: 33
ctgatttacc ctacagcttc aggcc                                              25

<210> SEQ ID NO 34
<211> LENGTH: 25
<212> TYPE: DNA
<213> ORGANISM: Homo sapiens

<400> SEQUENCE: 34
tagcttctgg tgttgttcct ttact                                              25

<210> SEQ ID NO 35
<211> LENGTH: 25
<212> TYPE: DNA
<213> ORGANISM: Homo sapiens

<400> SEQUENCE: 35
gagctactca cattagatgc atcct                                              25

<210> SEQ ID NO 36
<211> LENGTH: 25
<212> TYPE: DNA
<213> ORGANISM: Homo sapiens

<400> SEQUENCE: 36
gaaagttcag ccagaatctt cgtcc                                              25

<210> SEQ ID NO 37
<211> LENGTH: 25
<212> TYPE: DNA
<213> ORGANISM: Homo sapiens

<400> SEQUENCE: 37
atacagcagt tcgaaagccg cgtcc                                              25

<210> SEQ ID NO 38
<211> LENGTH: 25
<212> TYPE: DNA
<213> ORGANISM: Homo sapiens

<400> SEQUENCE: 38
ttcatctacc tctaccaacg gtgga                                              25
```

```
<210> SEQ ID NO 39
<211> LENGTH: 25
<212> TYPE: DNA
<213> ORGANISM: Homo sapiens

<400> SEQUENCE: 39
aggaggctcc gttttgcaaa gtgga                                     25

<210> SEQ ID NO 40
<211> LENGTH: 25
<212> TYPE: DNA
<213> ORGANISM: Homo sapiens

<400> SEQUENCE: 40
ctcagtagta ggtttctgtt ctatt                                     25

<210> SEQ ID NO 41
<211> LENGTH: 25
<212> TYPE: DNA
<213> ORGANISM: Homo sapiens

<400> SEQUENCE: 41
cattacgggt gttgaaggtg tcttc                                     25

<210> SEQ ID NO 42
<211> LENGTH: 25
<212> TYPE: DNA
<213> ORGANISM: Homo sapiens

<400> SEQUENCE: 42
ctgctagtct taagaactgc tttct                                     25

<210> SEQ ID NO 43
<211> LENGTH: 25
<212> TYPE: DNA
<213> ORGANISM: Homo sapiens

<400> SEQUENCE: 43
ggaaaacggg cagtctgctc tgctg                                     25

<210> SEQ ID NO 44
<211> LENGTH: 25
<212> TYPE: DNA
<213> ORGANISM: Homo sapiens

<400> SEQUENCE: 44
gccgttcagc ctggttagtt ttcta                                     25

<210> SEQ ID NO 45
<211> LENGTH: 25
<212> TYPE: DNA
<213> ORGANISM: Homo sapiens

<400> SEQUENCE: 45
gactgtcttg aacatcccaa atgcc                                     25

<210> SEQ ID NO 46
<211> LENGTH: 25
<212> TYPE: DNA
<213> ORGANISM: Homo sapiens

<400> SEQUENCE: 46
tcgcccacca accaagtgtt acaag                                     25
```

```
<210> SEQ ID NO 47
<211> LENGTH: 25
<212> TYPE: DNA
<213> ORGANISM: Homo sapiens

<400> SEQUENCE: 47
cgctttccac agtttgttac ctgca                                   25

<210> SEQ ID NO 48
<211> LENGTH: 25
<212> TYPE: DNA
<213> ORGANISM: Homo sapiens

<400> SEQUENCE: 48
ggacaaactg ccagttttgt ttcct                                   25

<210> SEQ ID NO 49
<211> LENGTH: 25
<212> TYPE: DNA
<213> ORGANISM: Homo sapiens

<400> SEQUENCE: 49
ctctcagata tggcctctta cagta                                   25

<210> SEQ ID NO 50
<211> LENGTH: 25
<212> TYPE: DNA
<213> ORGANISM: Homo sapiens

<400> SEQUENCE: 50
cttaagcaaa atactcccag gtctc                                   25

<210> SEQ ID NO 51
<211> LENGTH: 25
<212> TYPE: DNA
<213> ORGANISM: Homo sapiens

<400> SEQUENCE: 51
gcacagctgc ggtgatcgtc atgga                                   25

<210> SEQ ID NO 52
<211> LENGTH: 25
<212> TYPE: DNA
<213> ORGANISM: Homo sapiens

<400> SEQUENCE: 52
gtggtatgcc tgccaagaga cgcaa                                   25

<210> SEQ ID NO 53
<211> LENGTH: 25
<212> TYPE: DNA
<213> ORGANISM: Homo sapiens

<400> SEQUENCE: 53
tattcttgga ctgtactctt cgcat                                   25

<210> SEQ ID NO 54
<211> LENGTH: 25
<212> TYPE: DNA
<213> ORGANISM: Homo sapiens

<400> SEQUENCE: 54
gaaatcattg tgtctgcatt ggtca                                   25
```

```
<210> SEQ ID NO 55
<211> LENGTH: 25
<212> TYPE: DNA
<213> ORGANISM: Homo sapiens

<400> SEQUENCE: 55 gtagggggtta caattcacat tcctt                                    25

<210> SEQ ID NO 56
<211> LENGTH: 25
<212> TYPE: DNA
<213> ORGANISM: Homo sapiens

<400> SEQUENCE: 56
ggtctaggag atctgtccct tttag                                     25

<210> SEQ ID NO 57
<211> LENGTH: 25
<212> TYPE: DNA
<213> ORGANISM: Homo sapiens

<400> SEQUENCE: 57
ccataccacc actgagatct cattt                                     25

<210> SEQ ID NO 58
<211> LENGTH: 25
<212> TYPE: DNA
<213> ORGANISM: Homo sapiens

<400> SEQUENCE: 58
gaagcgaggc acaggcggtg tggac                                     25

<210> SEQ ID NO 59
<211> LENGTH: 25
<212> TYPE: DNA
<213> ORGANISM: Homo sapiens

<400> SEQUENCE: 59
gaggcagtaa gcgggcaggc agagc                                     25

<210> SEQ ID NO 60
<211> LENGTH: 25
<212> TYPE: DNA
<213> ORGANISM: Homo sapiens

<400> SEQUENCE: 60
tggtttaggg gttcatcggg gctga                                     25

<210> SEQ ID NO 61
<211> LENGTH: 25
<212> TYPE: DNA
<213> ORGANISM: Homo sapiens

<400> SEQUENCE: 61
accaaggttc tcatgaatct ccaac                                     25
```

US 10,835,531 B1

METHODS FOR PREDICTING DRUG RESPONSIVENESS IN CANCER PATIENTS

SEQUENCE LISTING

The instant application contains a Sequence Listing which has been submitted electronically in ASCII format and is hereby incorporated by reference in its entirety. Said ASCII copy, created on Jun. 10, 2019 is named "51167-018001_Sequence_Listing_6.10.19_ST25" and is 9,230 bytes in size.

FIELD OF THE INVENTION

The use of biomarkers to predict the responsiveness of a cancer in a subject to a cancer therapy.

BACKGROUND

DNA microarrays have been used to measure gene expression in tumor samples from patients and to facilitate diagnosis. Gene expression can reveal the presence of cancer in a patient in addition to the type, stage, and origin. Gene expression may even have a role in predicting the efficacy of cancer therapies. In recent decades, the National Cancer Institute (NCI) has tested cancer therapeutics for their effect in limiting the growth of 60 human cancer cell lines. The NCI has also measured gene expression in those 60 cancer cell lines using DNA microarrays. Various studies have explored the relationship between gene expression and therapeutic effect using the NCI datasets.

During cancer treatment, critical time is often lost due to a trial and error approach to finding an effective therapy. In addition, cancer cells often develop resistance to a previously effective therapy. In such situations, patient outcome would be greatly improved by early detection of such resistance.

Thus, there exists a need in the art for methods and devices that can predict the responsiveness of cancer patients to a medical treatment.

SUMMARY OF THE INVENTION

Featured are methods for detecting gene expression of a biomarker (e.g., one, two, three, four, five, ten, fifteen, twenty, twenty five, or all of the biomarkers shown in Tables 2 and/or 3, such as DDIT4 (SEQ ID NO: 1) and/or SCAMP5 (SEQ ID NO: 31)), respectively, in a patient, such as a patient with a cancer (e.g., a patient with breast cancer, endometrial cancer, renal cell cancer, or pancreatic cancer, or a recurrence thereof), and for determining responsiveness of a cancer patient (e.g., a patient with breast cancer, endometrial cancer, renal cell carcinoma (RCC), hepatocellular carcinoma (HCC), gastrointestinal stromal tumor (GIST), or lung cancer, or a recurrence thereof) to treatment with dovitinib or a pharmaceutically acceptable salt thereof. The invention also features methods of treating cancer in a patient in need thereof (e.g., a patient with breast cancer, endometrial cancer, RCC, HCC, GIST, or lung cancer, or a recurrence thereof) that include administering dovitinib or a pharmaceutically acceptable salt thereof to the patient, in which the patient is or has been determined to be responsive to dovitinib or a pharmaceutically acceptable salt thereof according to the diagnostic methods described herein.

Exemplary types of cancer that can be diagnosed or treated with the methods include, e.g., breast cancer (e.g., estrogen receptor-positive (ER pos) breast cancer or metastatic form of breast cancer), endometrial cancer (e.g., FGFR2-mutated or FGFR2-non-mutated advanced or metastatic endometrial cancer), renal cell carcinoma (RCC), hepatocellular carcinoma (HCC), gastrointestinal stromal tumor (GIST), lung cancer (e.g., non-small cell lung carcinoma, large cell carcinoma, bronchogenic carcinoma, and papillary adenocarcinoma), myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, prostate cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), ovarian cancer (e.g., ovarian adenocarcinoma or embryonal carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), breast cancer (e.g., medullary carcinoma), ER-positive cancer, bladder cancer, head and neck cancer (e.g., squamous cell carcinoma of the head and neck), metastatic cancer, oral cavity cancer, uterine cancer, testicular cancer (e.g., seminoma and embryonal carcinoma), skin cancer (e.g., squamous cell carcinoma, and basal cell carcinoma), thyroid cancer (e.g., papillary carcinoma and medullary carcinoma), brain cancer (e.g., astrocytoma and craniopharyngioma), stomach cancer, intraepithelial cancer, bone cancer, biliary tract cancer, eye cancer, liver cancer (e.g., hepatocellular carcinoma or hepatoma), larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, or neoplasms of the central nervous system. For example, the cancer may be a solid tumor or a hematological cancer.

A first aspect features a method of determining responsiveness of a patient with a cancer (e.g., one of the cancers noted above, such as breast cancer, endometrial cancer, RCC, HCC, GIST, or lung cancer) to dovitinib or a pharmaceutically acceptable salt thereof. In particular, the patient may have recurrence of cancer, such as recurrence of breast cancer, endometrial cancer, RCC, HCC, GIST, or lung cancer. The method includes: (a) contacting a sample (e.g., a tumor sample) from the patient including one or more nucleic acid molecules with a device (e.g., a microarray, such as a deoxyribonucleic acid (DNA)-based platform) including: (i) one or more single-stranded nucleic acid molecules capable of specifically hybridizing with the nucleotides of one or more biomarkers of sensitivity selected from the biomarkers of Table 2 (e.g., DDIT4 (SEQ ID NO: 1)); and/or (ii) one or more single-stranded nucleic acid molecules capable of specifically hybridizing with the nucleotides of one or more biomarkers of resistance selected from the biomarkers of Table 3 (e.g., SCAMP3 (SEQ ID NO: 31)); and (b) measuring hybridization between the one or more nucleic acid molecules from the patient and the single-stranded nucleic acid molecules of the device to detect a level of expression of the one or more biomarkers of sensitivity and/or the one or more biomarkers of resistance. The patient is determined to be responsive to dovitinib or a pharmaceutically acceptable salt thereof if: (i) the level of expression of the biomarker(s) of sensitivity (e.g., DDIT4 (SEQ ID NO: 1)) is substantially similar to the level of expression of the biomarker(s) of sensitivity in a cell (e.g., a cancer cell) or tissue (e.g., a tumor tissue) known to be sensitive to dovitinib or a pharmaceutically acceptable salt thereof (e.g., a tumor sample from a reference subject having the same diagnosis as the patient and that has been determined to be responsive to dovitinib or a pharmaceutically acceptable salt thereof); (ii) the level of expression of the biomarker(s) of resistance (e.g., SCAMP3 (SEQ ID NO: 31)) is substantially similar to the level of expression of the biomarker(s) of resistance in a cell (e.g., a cancer cell) or tissue (e.g., a tumor tissue) known to be sensitive to dovitinib or a pharmaceutically acceptable salt thereof (e.g., a tumor sample from a reference subject having the same diagnosis as the patient and that has been determined to be responsive to dovitinib or a pharmaceutically acceptable salt thereof); (iii) the level of expression of the biomarker(s) of sensitivity (e.g., DDIT4 (SEQ ID NO: 1)) is substantially dissimilar to the level of expression of the biomarker(s) of sensitivity in a cell (e.g., a cancer cell) or tissue (e.g., a tumor tissue) known to be resistant to dovitinib or a pharmaceutically acceptable salt thereof (e.g., a tumor sample from a reference subject having the same diagnosis as the patient and that has been determined to be resistant to dovitinib or a pharmaceutically acceptable salt thereof); and/or (iv) the level of expression of the biomarker(s) of resistance (e.g., SCAMP3 (SEQ ID NO: 31)) is substantially dissimilar to the level of expression of the biomarker(s) of resistance in a cell (e.g., a cancer cell) or tissue (e.g., a tumor tissue) known to be resistant to dovitinib or a pharmaceutically acceptable salt thereof (e.g., a tumor sample from a reference subject having the same diagnosis as the patient and that has been determined to be resistant to dovitinib or a pharmaceutically acceptable salt thereof). Responsiveness of the patient to dovitinib or a pharmaceutically acceptable salt thereof can also be assessed by calculating a difference score for the patient (mean of expression of the biomarkers of sensitivity noted above minus the mean of expression of the biomarkers of resistance noted above).

The method of the first aspect can further include administering dovitinib or a pharmaceutically acceptable salt thereof to the patient having: (i) a level of expression of the biomarker(s) of sensitivity (e.g., DDIT4 (SEQ ID NO: 1)) that is substantially similar to the level of expression of the biomarker(s) of sensitivity in a cell (e.g., a cancer cell) or tissue (e.g., a tumor tissue) known to be sensitive to dovitinib or a pharmaceutically acceptable salt thereof; (ii) a level of expression of the biomarker(s) of resistance (e.g., SCAMP3 (SEQ ID NO: 31)) that is substantially similar to the level of expression of the biomarker(s) of resistance in a cell (e.g., a cancer cell) or tissue (e.g., a tumor tissue) known to be sensitive to dovitinib or a pharmaceutically acceptable salt thereof; (iii) a level of expression of the biomarker(s) of sensitivity (e.g., DDIT4 (SEQ ID NO: 1)) that is substantially dissimilar to the level of expression of the biomarker(s) of sensitivity in a cell (e.g., a cancer cell) or tissue (e.g., a tumor tissue) known to be resistant to dovitinib or a pharmaceutically acceptable salt thereof; and/or (iv) a level of expression of the biomarker(s) of resistance (e.g., SCAMP3 (SEQ ID NO: 31)) that is substantially dissimilar to the level of expression of the biomarker(s) of resistance in a cell (e.g., a cancer cell) or tissue (e.g., a tumor tissue) known to be resistant to dovitinib or a pharmaceutically acceptable salt thereof. The method can further include administering one or more cancer therapies other than dovitinib or a pharmaceutically acceptable salt thereof to the patient having: (i) a level of expression of the biomarker(s) of sensitivity (e.g., DDIT4 (SEQ ID NO: 1)) that is substantially dissimilar to the level of expression of the biomarker(s) of sensitivity in a cell (e.g., a cancer cell) or tissue (e.g., a tumor tissue) known to be sensitive to dovitinib or a pharmaceutically acceptable salt thereof; (ii) a level of expression of the biomarker(s) of resistance (e.g., SCAMP3 (SEQ ID NO: 31)) that is substantially dissimilar to the level of expression of the biomarker(s) of resistance in a cell (e.g., a cancer cell) or tissue (e.g., a tumor tissue) known to be sensitive to dovitinib or a pharmaceutically acceptable salt thereof; (iii) a level of expression of the biomarker(s) of sensitivity (e.g., DDIT4 (SEQ ID NO: 1)) that is substantially similar to the level of expression of the biomarker(s) of sensitivity in a cell (e.g., a cancer cell) or tissue (e.g., a tumor tissue) known to be resistant to dovitinib or a pharmaceutically acceptable salt thereof; and/or (iv) a level of expression of the biomarker(s) of resistance (e.g., SCAMP3 (SEQ ID NO: 31)) that is substantially similar to the level of expression of the biomarker(s) of resistance in a cell (e.g., a cancer cell) or tissue (e.g., a tumor tissue) known to be resistant to dovitinib or a pharmaceutically acceptable salt thereof. In particular, the one or more cancer therapies can include surgery, radiation, or a therapeutic agent, such as a histone deacetylase (HDAC) inhibitor, an immune checkpoint inhibitor (e.g., a PD1 inhibitor, a PD-L1 inhibitor, or a CTLA-4 inhibitor), ipilimumab, a cyclin-dependent kinase inhibitor (e.g., a CDK inhibitor selective for CDK4 and CDK6, such as palbociclib (IBRANCE®) and abemaciclib (VERZENIO®, VERZENIOS®)), venetoclax (VENCLEXTA®, VENCLYXTO®), ibrutinib (IMBRUVICA®), bortezomib, carfilzomib, thalidomide, lenalidomide, pomalidomide, prednisone, dexamethasone, cyclophosphamide, vincristine, doxorubicin, melphalan, capecitabine, tegafur, irinotecan, oxaliplatin, cetuximab, leucovorin, SN-38, everolimus, temsirolimus, bleomycin, lomustine, depsipeptide, carboplatin, erlotinib, gemcitabine, mitoxantrone, cisplatin, busulfan, epirubicin, arsenic trioxide, bendamustine, fulvestrant, teniposide, adriamycin, decitabine, estramustine, etoposide, azaguanine, aclarubicin, mitoxantrone, mitomycin, paclitaxel, taxotere, Irofulven, 5-FU, ara-c, methylprednisolone, methotrexate, methyl-gag, belinostat, carboplatin, idarubicin, IL4-PR38, valproic acid, all-trans retinoic acid (ATRA), cytoxan, topotecan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, tamoxifen, floxuridine, thioguanine, PSC 833, herceptin, bevacizumab, celecoxib, iressa, anastrozole, letrozole, or rituximab.

Also featured is a method of treating cancer in a patient in need thereof (e.g., a patient with one of the cancers noted above, such as breast cancer, endometrial cancer, RCC, HCC, GIST, or lung cancer) that includes administering dovitinib or a pharmaceutically acceptable salt thereof to the patient, in which the patient has been determined to be responsive to dovitinib or a pharmaceutically acceptable salt thereof according to the method of the first aspect of the invention. In particular, the patient may have recurrence of cancer, such as recurrence of breast cancer, endometrial cancer, RCC, HCC, GIST, or lung cancer.

A second aspect features a method of treating a patient having cancer (e.g., one of the cancers noted above, such as breast cancer, endometrial cancer, RCC, HCC, GIST, or lung cancer). In particular, the patient may have recurrence of cancer, such as recurrence of breast cancer, endometrial cancer, RCC, HCC, GIST, or lung cancer. The method includes: (a) contacting a sample (e.g., a tumor sample) from the patient including one or more nucleic acid molecules with a device including: (i) one or more single-stranded nucleic acid molecules capable of specifically hybridizing with the nucleotides of one or more biomarkers of sensitivity selected from the biomarkers of Table 2 (e.g., DDIT4 (SEQ ID NO: 1)); and/or (ii) one or more single-stranded nucleic acid molecules capable of specifically hybridizing with the nucleotides of one or more biomarkers of resistance selected from the biomarkers of Table 3 (e.g., SCAMP3 (SEQ ID NO: 31)); (b) measuring hybridization between the one or more nucleic acid molecules from the patient and the single-stranded nucleic acid molecules of the device to detect a level of expression of the one or more biomarkers of sensitivity and/or the one or more biomarkers of resistance; and (c) administering dovitinib or a pharmaceutically acceptable salt thereof to the patient. Dovitinib or a pharmaceutically acceptable salt thereof can be administered to the patient if: (i) the level of expression of the biomarker(s) of sensitivity (e.g., DDIT4 (SEQ ID NO: 1)) is substantially similar to the level of expression of the biomarker(s) of sensitivity in a cell (e.g., a cancer cell) or tissue (e.g., a tumor tissue) known to be sensitive to dovitinib or a pharmaceutically acceptable salt thereof; (ii) the level of expression of the biomarker(s) of resistance (e.g., SCAMP3 (SEQ ID NO: 31)) is substantially similar to the level of expression of the biomarker(s) of resistance in a cell (e.g., a cancer cell) or tissue (e.g., a tumor tissue) known to be sensitive to dovitinib or a pharmaceutically acceptable salt thereof; (iii) the level of expression of the biomarker(s) of sensitivity (e.g., DDIT4 (SEQ ID NO: 1)) is substantially dissimilar to the level of expression of the biomarker(s) of sensitivity in a cell (e.g., a cancer cell) or tissue (e.g., a tumor tissue) known to be resistant to dovitinib or a pharmaceutically acceptable salt thereof; and/or (iv) the level of expression of the biomarker(s) of resistance (e.g., SCAMP3 (SEQ ID NO: 31)) is substantially dissimilar to the level of expression of the biomarker(s) of resistance in a cell (e.g., a cancer cell) or tissue (e.g., a tumor tissue) known to be resistant to dovitinib or a pharmaceutically acceptable salt thereof.

The method of the second aspect may further include administering one or more additional therapies (e.g., surgery, radiation, or a therapeutic agent) to the patient prior to, concurrently with, or after administration of dovitinib or a pharmaceutically acceptable salt thereof. In some embodiments, a therapeutic agent that is administered to the patient prior to, concurrently with, or after administration of dovitinib or a pharmaceutically acceptable salt thereof is one or more of a histone deacetylase (HDAC) inhibitor, an immune checkpoint inhibitor, an antiestrogen, an aromatase inhibitor, an antigonadotropin, a proteasome inhibitor, an immunomodulator, a glucocorticoid, a folic acid, a monoclonal antibody, or an antineoplastic agent. In particular embodiments, a therapeutic agent that is administered to the patient prior to, concurrently with, or after administration of dovitinib or a pharmaceutically acceptable salt thereof is one or more of a HDAC inhibitor, an immune checkpoint inhibitor (e.g., a PD1 inhibitor (e.g., Pembrolizumab, Nivolumab, and Cemiplimab), a PD-L1 inhibitor (e.g., Atezolizumab, Avelumab, and Durvalumab), and a CTLA-4 inhibitor (e.g., Ipilimumab, and Tremelimumab)), an aromatase inhibitor (e.g., a non-selective aromatase inhibitor, such as Aminoglutethimide and Testolactone; a selective aromatase inhibitor, such as anastrozole, letrozole, exemestane, vorozole, formestane, and fadrozole; and other aromatase inhibitors, such as 1,4,6-Androstatrien-3,17-dione (ATD) and 4-Androstene-3,6,17-trione (6-OXO)), an antiestrogen (e.g., a selective estrogen receptor modulator (SERM) (e.g., tamoxifen, clomifene, and raloxifene), an estrogen receptor silent antagonist, and selective estrogen receptor degrader (SERD) (e.g., fulvestrant)), an antigonadotropin (e.g., gonadotropin-releasing hormone (GnRH) analogue, compounds acting on sex steroid hormone receptors (e.g., progestogens, androgens, and estrogens), and steroid synthesis inhibitors (e.g., danazol and gestrinone)), a cyclin-dependent kinase inhibitor (e.g., a CDK inhibitor selective for CDK4 and CDK6, such as palbociclib (IBRANCE®) and abemaciclib (VERZENIO®, VERZENIOS®)), venetoclax (VENCLEXTA®, VENCLYXTO®), ibrutinib (IMBRUVICA®), bortezomib, carfilzomib, thalidomide, lenalidomide, pomalidomide, prednisone, dexamethasone, cyclophosphamide, vincristine, doxorubicin, melphalan, capecitabine, tegafur, irinotecan, oxaliplatin, cetuximab, leucovorin, SN-38, everolimus, temsirolimus, bleomycin, lomustine, depsipeptide, carboplatin, erlotinib, gemcitabine, mitoxantrone, cisplatin, busulfan, epirubicin, arsenic trioxide, bendamustine, teniposide, adriamycin, decitabine, estramustine, etoposide, azaguanine, aclarubicin, mitoxantrone, mitomycin, paclitaxel, taxotere, Irofulven, 5-FU, ara-c, methylprednisolone, methotrexate, methyl-gag, belinostat, carboplatin, idarubicin, IL4-PR38, valproic acid, all-trans retinoic acid (ATRA), cytoxan, topotecan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, floxuridine, thioguanine, PSC 833, herceptin, bevacizumab, celecoxib, iressa, anastrozole, letrozole, or rituximab. The therapeutic agent can be administered parenterally (e.g. intravenously, intramuscularly, transdermally, intradermally, intra-arterially, intracranially, subcutaneously, intraorbitally, intraventricularly, intraspinally, intraperitoneally, or intranasally), enterally, or topically.

In some embodiments, the method of administering an immune checkpoint inhibitor in combination with dovitinib or a pharmaceutically acceptable salt thereof further includes a step of determining responsiveness of a sample (e.g., a tumor sample, such as a tumor sample from a subject) to the immune checkpoint inhibitor. The method includes assessing an expression level of a three-gene biomarker of checkpoint inhibition, in which the expression level of the three-gene biomarker of checkpoint inhibition can include, e.g., an average of expression level of the three genes (e.g., PD-1 (e.g., SEQ ID NO: 59), PD-L1 (e.g., SEQ ID NO: 60), and FAS (e.g., SEQ ID NO: 61)) listed in Table 4. In particular embodiments, the expression level of the three-gene biomarker of checkpoint inhibition can be compared to a reference population (e.g., corresponding to tumor samples of the same type as the tested sample (such as, e.g., from subjects diagnosed with the same type of tumor)), in which an expression level at the $50^{th}$ percentile of the reference population, or the $60^{th}$ percentile, or the $70^{th}$ percentile, or the 80th percentile, or the 90th percentile, or greater, indicates that the sample (or the subject from whom the sample was taken) is predicted to be responsive to treatment with an immune checkpoint inhibitor. The confidence of the prediction increases as the percentile level increases (e.g., an expression level above the 90th percentile of a reference population indicates a greater likelihood of treatment responsiveness than an expression level at the 50th percentile). Conversely, an expression level in the tested sample of below the 50th percentile of the reference population indicates that the sample (or the subject from whom the sample was taken) is predicted to be non-responsive to treatment with an immune checkpoint inhibitor.

In the first or second aspect, dovitinib or a pharmaceutically acceptable salt thereof may be administered parenterally (e.g. intravenously, intramuscularly, transdermally, intradermally, intra-arterially, intracranially, subcutaneously, intraorbitally, intraventricularly, intraspinally, intraperitoneally, or intranasally), enterally (e.g., orally), or topically. Preferably, dovitinib or a pharmaceutically acceptable salt thereof is administered orally. Dovitinib or a pharmaceutically acceptable salt thereof may be administered to the patient two or more times, such as one or more times daily (e.g., once daily for up to six days), weekly, every two weeks, every three weeks, or monthly. Preferably, dovitinib or a pharmaceutically acceptable salt thereof is administered once daily. In particular, dovitinib or a pharmaceutically acceptable salt thereof is administered once daily for five days. In some embodiments of any of the above aspects, dovitinib or a pharmaceutically acceptable salt thereof may be administered in an ON: OFF schedule, such as a schedule that includes an ON schedule and an OFF schedule, wherein dovitinib or a pharmaceutically acceptable salt thereof is administered during the ON schedule, and dovitinib or a pharmaceutically acceptable salt thereof is not administered during the OFF schedule. In some embodiments, dovitinib or a pharmaceutically acceptable salt thereof is administered in a one-ten days (e.g., one day, two days, three days, four days, five days, six days, seven days, eight days, nine days, or ten days) ON: one-ten days (e.g., one day, two days, three days, four days, five days, six days, seven days, eight days, nine days, or ten days) OFF schedule, wherein dovitinib or a pharmaceutically acceptable salt thereof is administered for one-ten days during the ON schedule and dovitinib or a pharmaceutically acceptable salt thereof is not administered for one-ten days (e.g., one-ten days (e.g., one day, two days, three days, four days, five days, six days, seven days, eight days, nine days, or ten days) following the ON schedule) during the OFF schedule. Preferably, dovitinib or a pharmaceutically acceptable salt thereof is administered in a five days ON: two days OFF schedule. The method may further include administering a second dose of dovitinib or a pharmaceutically acceptable salt thereof to the subject (e.g., patient) two days, four days, six days, one week, two weeks, three weeks, four weeks, or five weeks after administration of a first dose of dovitinib or a pharmaceutically acceptable salt thereof. Dovitinib or a pharmaceutically acceptable salt thereof may be administered in a particular dosage form (e.g., liquid, tablet, capsule, etc.) and it may be administered at a dose of about 5-5000 mg (e.g., about 50-800 mg). In particular, dovitinib or a pharmaceutically acceptable salt thereof may be administered at doses of about 10 mg, 50 mg, 200 mg, or 500 mg. Preferably, about 500 mg of dovitinib or a pharmaceutically acceptable salt thereof is administered daily (e.g., once daily, such as 500 mg once daily). In particular embodiments, about 500 mg of dovitinib or a pharmaceutically acceptable salt thereof may be administered once daily for five days. Preferably, about 500 mg of dovitinib or a pharmaceutically acceptable salt thereof is administered once daily in a five days ON: two days OFF schedule. Dovitinib or a pharmaceutically acceptable salt thereof can be administered in the form of hard gelatin capsules (e.g., hard gelatin capsules of 10 mg, 50 mg, 100 mg, 200 mg, or 250 mg) or film coated tablets (e.g., film coated tablets of 10 mg, 50 mg, 100 mg, 200 mg, or 250 mg). Preferably, dovitinib or a pharmaceutically acceptable salt thereof is administered in the form of hard gelatin capsules of 100 mg (e.g., 5×100 mg hard gelatin capsules daily) or film coated tablets of 250 mg (e.g., 2×250 mg film coated tablets daily). In particular embodiments of the first and second aspects, the contacting step (a) and the measuring step (b) may occur prior to, concurrent to, or after administration of dovitinib or a pharmaceutically acceptable salt thereof to the patient. Each of the contacting step (a) and the measuring step (b) may occur multiple times.

In any of the above aspects, the device (e.g., a microarray, such as a DNA-based platform) can include at least two, at least three, at least four, at least five, at least six, at least seven, at least eight, at least nine, at least ten, or more single-stranded nucleic acid molecules capable of specifically hybridizing with the nucleotides of one or more biomarkers of sensitivity selected from the biomarkers of Table 2 (e.g., DDIT4 (SEQ ID NO: 1)); and/or at least two, at least three, at least four, at least five, at least six, at least seven, at least eight, at least nine, at least ten, or more single-stranded nucleic acid molecules capable of specifically hybridizing with the nucleotides of one or more biomarkers of resistance selected from the biomarkers of Table 3 (e.g., SCAMP3 (SEQ ID NO: 31)). For example, the device may have single-stranded nucleic acid molecule(s) having the sequence of or complementary to each of the biomarkers of sensitivity selected from the biomarkers of Table 2 and for each of the biomarkers of resistance selected from the biomarkers of Table 3 that are affixed to the device and can be used to detect the level of expression of the biomarkers, e.g., by hybridization. In particular, one or more of the single-stranded nucleic acid molecules of the device have a length in the range of 10 to 100 nucleotides in length (e.g., a length in the range of 20 to 60 nucleotides).

In any of the aforementioned aspects, the sensitivity and/or resistance of a cell (e.g., a cancer cell) or tissue (e.g., a tumor tissue) known to be sensitive and/or resistant to dovitinib is based on GI50 data of NCI60 cell lines.

In any of the above aspects, the method may include converting the level of expression of one or more of the biomarkers of sensitivity (e.g., one, two, three, four, five, ten, fifteen, twenty, twenty five, or all of the biomarkers shown in Table 2 (e.g., the top one biomarker, the top two biomarkers, the top three biomarkers, the top four biomarkers, the top five biomarkers, the top ten biomarkers, the top fifteen biomarkers, the top twenty biomarkers, the top twenty five biomarkers, or all of the biomarkers shown in Table 2), such as DDIT4 (SEQ ID NO: 1)) and/or one or more of the biomarkers of resistance (e.g., one, two, three, four, five, ten, fifteen, twenty, twenty five, or all of the biomarkers shown in Table 3 (e.g., the top one biomarker, the top two biomarkers, the top three biomarkers, the top four biomarkers, the top five biomarkers, the top ten biomarkers, the top fifteen biomarkers, the top twenty biomarkers, the top twenty five biomarkers, or all of the biomarkers shown in Table 3), such as SCAMP3 (SEQ ID NO: 31)) into a mean score, in which the mean score indicates the responsiveness of the patient to dovitinib or a pharmaceutically acceptable salt thereof. The method can further include subtracting the mean score for one or more of the biomarkers of resistance (e.g., one, two, three, four, five, ten, fifteen, twenty, twenty five, or all of the biomarkers shown in Table 3 (e.g., the top one biomarker, the top two biomarkers, the top three biomarkers, the top four biomarkers, the top five biomarkers, the top ten biomarkers, the top fifteen biomarkers, the top twenty biomarkers, the top twenty five biomarkers, or all of the biomarkers shown in Table 3), such as SCAMP3 (SEQ ID NO: 31)) from the mean score for one or more of the biomarkers of sensitivity (e.g., one, two, three, four, five, ten, fifteen, twenty, twenty five, or all of the biomarkers shown in Table 2 (e.g., the top one biomarker, the top two biomarkers, the top three biomarkers, the top four biomarkers, the top five biomarkers, the top ten biomarkers, the top fifteen biomarkers, the top twenty biomarkers, the top twenty five biomarkers, or all of the biomarkers shown in Table 2), such as DDIT4 (SEQ ID NO: 1)) to obtain a difference score, in which the difference score indicates the responsiveness of the patient to dovitinib. In particular, the mean score and/or the difference score can be compared to a reference population of tumor samples of the same type (e.g., from subjects diagnosed with the same type of tumor), in which the 50$^{th}$ percentile of the reference population, or the 60$^{th}$ percentile, or the 70$^{th}$ percentile, or the 80$^{th}$ percentile, or the 90$^{th}$ percentile, or greater, can be used to predict the likelihood that a tumor (or a subject from whom the tumor sample is taken) will be responsive or non-responsive to a treatment (e.g., treatment with dovitinib or a pharmaceutically acceptable salt thereof). For example, an expression level (or the mean score and/or the difference score thereof) of a sample (e.g., a tumor sample from a subject) at the 50$^{th}$ percentile of the reference population, or the 60$^{th}$ percentile, or the 70$^{th}$ percentile, or the 80$^{th}$ percentile, or the 90$^{th}$ percentile, or greater, indicates that the sample (or the subject from whom the sample was taken) is predicted to be responsive to treatment with dovitinib or a pharmaceutically acceptable salt thereof. The confidence of the prediction increases as the percentile level increases (e.g., an expression level above the 90$^{th}$ percentile of a reference population indicates a greater likelihood of treatment responsiveness than an expression level at the 50$^{th}$ percentile). Conversely, an expression level in the tested sample of below the 50$^{th}$ percentile of the reference population indicates that the sample (or the subject from whom the sample was taken) is predicted to be non-responsive to treatment with dovitinib or a pharmaceutically acceptable salt thereof.

In any of the above aspects, the device can be a microarray, such as a DNA-based platform. The expression level of the biomarkers of sensitivity (e.g., one, two, three, four, five, ten, fifteen, twenty, twenty five, or all of the biomarkers shown in Table 2 (e.g., the top one biomarker, the top two biomarkers, the top three biomarkers, the top four biomarkers, the top five biomarkers, the top ten biomarkers, the top fifteen biomarkers, the top twenty biomarkers, the top twenty five biomarkers, or all of the biomarkers shown in Table 2), such as DDIT4 (SEQ ID NO: 1)) and/or the biomarkers of resistance (e.g., one, two, three, four, five, ten, fifteen, twenty, twenty five, or all of the biomarkers shown in Table 3 (e.g., the top one biomarker, the top two biomarkers, the top three biomarkers, the top four biomarkers, the top five biomarkers, the top ten biomarkers, the top fifteen biomarkers, the top twenty biomarkers, the top twenty five biomarkers, or all of the biomarkers shown in Table 3), such as SCAMP3 (SEQ ID NO: 31)) can be measured using microarray analysis or nucleic acid amplification methods (e.g., reverse transcription quantitative real-time polymerase chain reaction (RT-qPCR)). In particular, the level of expression of the biomarkers of sensitivity and/or the biomarkers of resistance is determined by detecting the level of mRNA transcribed from a gene coding one or more of the biomarkers of Table(s) 2 and/or 3.

In any of the above aspects, the biomarker of sensitivity may be selected from one or more of DDIT4 (SEQ ID NO: 1), ZNF395 (SEQ ID NO: 2), lncRNA (SEQ ID NO: 3), LSM4 (SEQ ID NO: 4), SEL1L3 (SEQ ID NO: 5), FABP5 (SEQ ID NO: 6), TRIM22 (SEQ ID NO: 7), TPK1 (SEQ ID NO: 8), SLC16A3 (SEQ ID NO: 9), INSIG1 (SEQ ID NO: 10), HOXA10-HOXA9 HOXA9 MIR196B (SEQ ID NO: 11), DPP4 (SEQ ID NO: 12), LDLR (SEQ ID NO: 13), HSPE1 (SEQ ID NO: 14), VEGFA (SEQ ID NO: 15), TMSB10 (SEQ ID NO: 16), SLC16A3 (SEQ ID NO: 17), VEGFA (SEQ ID NO: 18), CAV2 (SEQ ID NO: 19), P4HA1 (SEQ ID NO: 20), APOL1 (SEQ ID NO: 21), CAV2 (SEQ ID NO: 22), PTPRE (SEQ ID NO: 23), DPYSL2 (SEQ ID NO: 24), ANP32B (SEQ ID NO: 25), STAT6 (SEQ ID NO: 26), RPL27A SNORA3 (SEQ ID NO: 27), EPB41 L2 (SEQ ID NO: 28), RPL38 (SEQ ID NO: 29), and RNU86 RPL3 SNORD83B (SEQ ID NO: 30).

In any of the above aspects, the biomarker of resistance may be selected from one or more of SCAMP3 (SEQ ID NO: 31), BAGS (SEQ ID NO: 32), ABCF1 (SEQ ID NO: 33), MARCH6 (SEQ ID NO: 34), EMC3 (SEQ ID NO: 35), UCP2 (SEQ ID NO: 36), TUG1 (SEQ ID NO: 37), CLPTM1 (SEQ ID NO: 38), IGFBP5 (SEQ ID NO: 39), MAGEA1 (SEQ ID NO: 40), ATM (SEQ ID NO: 41), GATA3 (SEQ ID NO: 42), SPDEF (SEQ ID NO: 43), LDOC1 (SEQ ID NO: 44), HRAS (SEQ ID NO: 45), SRM (SEQ ID NO: 46), ZNF331 (SEQ ID NO: 47), GATA3 (SEQ ID NO: 48), TOB1 (SEQ ID NO: 49), APITD1 CORT (SEQ ID NO: 50), NDUFV1 (SEQ ID NO: 51), BAG6 (SEQ ID NO: 52), CUL3 (SEQ ID NO: 53), CCDC90A (SEQ ID NO: 54), CERS2 (SEQ ID NO: 55), LOC100506032 NBPF10 NBPF11 NBPF12 NBPF15 NBPF16 NBPF24 NBPF7 NBPF8 NBPF9 (SEQ ID NO: 56), PPP1R11 (SEQ ID NO: 57), and CKB (SEQ ID NO: 58).

In particular embodiments, the biomarkers of sensitivity may include one or more of: (a) SEQ ID NOs: 1-15; and/or (b) SEQ ID NOs: 16-30. In more specific embodiments, the biomarker of sensitivity may be DDIT4 (SEQ ID NO: 1).

In particular embodiments, the biomarkers of resistance may include one or more of: (a) SEQ ID NOs: 31-45; and/or (b) SEQ ID NOs: 46-58. In more specific embodiments, the biomarker of resistance may be SCAMP3 (SEQ ID NO: 31).

In particular embodiments, the biomarker of sensitivity may be DDIT4 (e.g., SEQ ID NO: 1) and the biomarker of resistance may be SCAMP3 (e.g., SEQ ID NO: 31).

In particular embodiments, the biomarkers of sensitivity may be selected from at least 5, at least 10, at least 15, at least 20, at least 25, or at least 27 of the biomarkers of Table 2 (e.g., at least the top 5 biomarkers, at least the top 10 biomarkers, at least the top 15 biomarkers, at least the top 20 biomarkers, at least the top 25 biomarkers, or at least the top 27 biomarkers of Table 2). The biomarkers of resistance may be selected from at least 5, at least 10, at least 15, at least 20, at least 25, or at least 27 of the biomarkers of Table 3 (e.g., at least the top 5 biomarkers, at least the top 10 biomarkers, at least the top 15 biomarkers, at least the top 20 biomarkers, at least the top 25 biomarkers, or at least the top 27 biomarkers of Table 3).

In any of the above aspects, the cancer is selected from a solid tumor cancer and a hematological cancer. For example, the cancer is, e.g., multiple myeloma, breast cancer, acute myelogenous leukemia (AML), acute lympho-blastic leukemia (ALL), chronic lymphocytic leukemia (CLL), myelodysplastic syndrome (MDS), chronic myelogenous leukemia—chronic phase (CMLCP), diffuse large B-cell lymphoma (DLBCL), cutaneous T-cell lymphoma (CTCL), peripheral T-cell lymphoma (PTCL), Hodgkin's lymphoma, hepatocellular carcinoma (HCC), cervical cancer, prostate cancer, kidney cancer, renal cell carcinoma (RCC), esophageal cancer, melanoma, glioma, pancreatic cancer, ovarian cancer, gastrointestinal stromal tumors (GIST), sarcoma, breast cancer, estrogen receptor-positive (ERpos) breast cancer, metastatic breast cancer, endometrial cancer, lung cancer, non-small cell lung carcinoma (NSCLC), mesothelioma, intestinal cancer, colon cancer, bladder cancer, adrenal cancer, gallbladder cancer, or squamous cell carcinoma of the head and neck (SCCHN). In some embodiments, the cancer is breast cancer (e.g., estrogen receptor-positive (ER pos) breast cancer, or a metastatic form of breast cancer). In other embodiments, the cancer is endometrial cancer. In some embodiments, the cancer is renal cell carcinoma (RCC). In another embodiment, the cancer is hepatocellular carcinoma (HCC). In some embodiments, the cancer is gastrointestinal stromal tumor (GIST). In another embodiment, the cancer is lung cancer.

DEFINITIONS

As used herein, "a" or "an" means "at least one" or "one or more" unless otherwise indicated. In addition, the singular forms "a", "an", and "the" include plural referents unless the context clearly dictates otherwise.

As used herein, "about" refers to an amount ±10% of the recited value.

As used herein, the term "dovitinib," "TKI-258," or "TKI 258" refers to 4-amino-5-fluoro-3-[6-(4-methylpiperazin-1-yl)-1H-benzimidazol-2-yl]-1H-quinolin-2-one or a tautomer thereof, or a mixture of tautomers thereof. 4-amino-5-fluoro-3-[6-(4-methylpiperazin-1-yl)-1H-benzimidazol-2-yl]-1H-quinolin-2-one has the following structure:

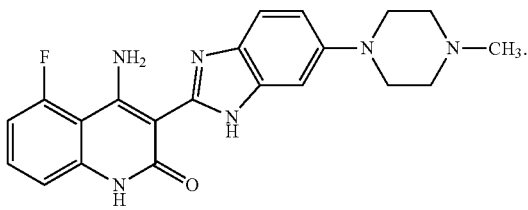 [SMILES: CN1CCN(c2ccc3nc(-c4c(N)c5c(F)cccc5[nH]c4=O)[nH]c3c2)CC1]

Dovitinib is a small molecule targeted inhibitor of protein kinases (e.g., tyrosine receptor kinases (RTKs)). Receptor tyrosine kinases (RTKs) are transmembrane polypeptides that regulate developmental cell growth and differentiation, remodeling and regeneration of adult tissues. Polypeptide ligands known as growth factors or cytokines, are known to activate RTKs. Signaling RTKs involves ligand binding and a shift in conformation in the external domain of the receptor resulting in its dimerization. Binding of the ligand to the RTK results in receptor trans-phosphorylation at specific tyrosine residues and subsequent activation of the catalytic domains for the phosphorylation of cytoplasmic substrates.

Dovitinib, or a hydrate or solvate thereof, exists in a variety of polymorphs. Dovitinib, or a hydrate or solvate thereof, or a polymorph thereof, is useful for inhibiting angiogenesis and treating proliferative diseases.

The structure and activity of 4-amino-5-fluoro-3-[6-(4-methylpiperazin-1-yl)-1H-benzimidazol-2-yl]-1H-quinolin-2-one or a tautomer thereof is described in WO 2002/022598 and WO 2012/001074, hereby incorporated by reference.

By "biomarker" is meant a nucleic acid molecule (e.g., an mRNA or its complement, for example, a cDNA) or a protein encoded by the nucleic acid molecule present in, or from, a cell or tissue. The expression of the biomarker correlates to the responsiveness (e.g., sensitivity or resistance) of the cell or tissue (and thus, the patient containing the cell or tissue or the patient from which the cell or tissue was obtained) to a cancer treatment (e.g., dovitinib or a pharmaceutically acceptable salt thereof). In particular, a biomarker of sensitivity is a nucleic acid molecule (e.g., a mRNA or its complement) expressed from any one of the genes shown in Table 2, or the protein encoded by the nucleic acid molecule, and a biomarker of resistance is a nucleic acid molecule (e.g., a mRNA or its complement) expressed from any one of the genes shown in Table 3, or the protein encoded by the nucleic acid molecule.

The terms "cancer" and "cancerous" refer to or describe the physiological condition in mammals (e.g., humans) that is typically characterized by unregulated cell proliferation. Examples of cancer include, but are not limited to, myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, prostate cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), ovarian cancer (e.g., ovarian adenocarcinoma or embryonal carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), breast cancer (e.g., medullary carcinoma), ER-positive cancer, bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma and basal cell carcinoma), thyroid cancer (e.g., papillary carcinoma and medullary carcinoma), brain cancer (e.g., astrocytoma and craniopharyngioma), stomach cancer, intra-epithelial cancer, bone cancer, biliary tract cancer, eye cancer, liver cancer (e.g., hepatocellular carcinoma or hepatoma), larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, and neoplasms of the central nervous system. The term cancer includes hematological cancers (e.g., cancer of the blood, such as multiple myeloma) and solid tumors (e.g., breast cancer).

The terms "expression level" and "level of expression," as used herein interchangeably, refer to the amount of a gene product in a cell, tissue, biological sample, organism, or patient, e.g., amounts of DNA, RNA (e.g. messenger RNA (mRNA)), or proteins of a given gene.

"Gene" as used herein indicates a coding or noncoding gene whose activity can be determined by measuring the produced RNA. Examples include protein coding genes, microRNAs, small nuclear RNAs and other RNAs with catalytic, regulatory or coding properties.

To "inhibit growth" as used herein means causing a reduction in cell growth (e.g., cancer cell growth, e.g., as compared to the growth inhibition of the NCI60 cancer cell lines as a reference) in vivo or in vitro by, e.g., 10%, 20%, 30%, 40%, 50%, 60%, 70%, 80%, 90%, 95%, or 99% or more, as evident by a reduction in the proliferation of cells exposed to a treatment (e.g., dovitinib or a pharmaceutically acceptable salt thereof), relative to the proliferation of cells in the absence of the treatment. Growth inhibition may be the result of a treatment (e.g., dovitinib or a pharmaceutically acceptable salt thereof) that induces apoptosis in a cell, induces necrosis in a cell, slows cell cycle progression, disrupts cellular metabolism, induces cell lysis, or induces some other mechanism that reduces the proliferation of cells.

"Microarray" as used herein means a device employed by any method that quantifies one or more subject oligonucleotides, e.g., RNA, DNA, cDNA, or analogues thereof, at a time. For example, many DNA microarrays, including those made by Affymetrix (e.g., an Affymetrix HG-U133A array), use several probes for determining the expression of a single gene. The DNA microarray may contain oligonucleotide probes that may be, e.g., full-length cDNAs complementary to an RNA or cDNA fragments that hybridize to part of an RNA. The DNA microarray may also contain modified versions of DNA or RNA, such as locked nucleic acids or LNA. Exemplary RNAs include mRNA, miRNA, and miRNA precursors.

As used herein, the term "percent (%) sequence identity" refers to the percentage of nucleic acid residues of a candidate sequence, e.g., a probe or primer of the invention, that are identical to the nucleic acid residues of a reference sequence, e.g., a biomarker sequence of the invention, after aligning the sequences and introducing gaps, if necessary, to achieve the maximum percent sequence identity (e.g., gaps can be introduced in one or both of the candidate and reference sequences for optimal alignment and non-homologous sequences can be disregarded for comparison purposes). Alignment for purposes of determining percent sequence identity can be achieved in various ways that are within the skill in the art, for instance, using computer software, such as BLAST, BLAST-2, BLAST-P, BLAST-N, BLAST-X, WU-BLAST-2, ALIGN, ALIGN-2, CLUSTAL, Megalign (DNASTAR). In addition, those skilled in the art can determine appropriate parameters for measuring alignment, including any algorithms needed to achieve optimal alignment over the length of the sequences being compared.

"NCI60" as used herein means a panel of 60 cancer cell lines from lung, colon, breast, ovarian, leukemia, renal, melanoma, prostate and brain cancers including the following cancer cell lines: NSCLC_NCIH23, NSCLC_NCIH522, NSCLC_A549ATCC, NSCLC_EKVX, NSCLC_NCIH226, NSCLC_NCIH332M, NSCLC_H460, NSCLC_HOP62, NSCLC_HOP92, COLON_HT29, COLON_HCC-2998, COLON_HCT116, COLON_SW620, COLON_COL0205, COLON_HCT15, COLON_KM12, BREAST_MCF7, BREAST_MCF7ADRr, BREAST_MDAMB231, BREAST_HS578T, BREAST_MDAMB435, BREAST_MDN, BREAST_BT549, BREAST_T47D, OVAR_OVCAR3, OVAR_OVCAR4, OVAR_OVCAR5, OVAR_OVCAR8, OVAR_IGROV1, OVAR_SKOV3, LEUK_CCRFCEM, LEUK_K562, LEUK_MOLT4, LEUK_HL60, LEUK_RPMI8266, LEUK_SR, RENAL_UO31, RENAL_SN12C, RENAL_A498, RENAL_CAKI1, RENAL_RXF393, RENAL_7860, RENAL_ACHN, RENAL_TK10, MELAN_LOXIMVI, MELAN_MALME3M, MELAN_SKMEL2, MELAN_SKMEL5, MELAN_SKMEL28, MELAN_M14, MELAN_UACC62, MELAN_UACC257, PROSTATE_PC3, PROSTATE_DU145, CNS_SNB19, CNS_SNB75, CNS_U251, CNS_SF268, CNS_SF295, and CNS_SF539.

The terms "patient" and "subject," as used interchangeably herein, refer to any animal (e.g., a mammal, such as a human). A patient to be treated or tested for responsiveness to a treatment (e.g., dovitinib or a pharmaceutically acceptable salt thereof) according to the methods described herein may be one who has been diagnosed with a cancer, such as ovarian cancer or breast cancer. Diagnosis may be performed by any method or techniques known in the art, such as x-ray, MRI, or biopsy, and confirmed by a physician. To minimize exposure of a patient to drug treatments that may not be therapeutic, the patient may be determined to be either responsive or non-responsive to a cancer treatment, such as dovitinib or a pharmaceutically acceptable salt thereof, according to the methods described herein.

"Resistance" as used herein means that a cell (e.g., a cancer cell) or a tissue (e.g., a tumor) in vitro or in vivo (e.g., in a subject with a cancer, such as a human) is tolerant to treatment with an anti-cancer agent (e.g., dovitinib or a pharmaceutically acceptable salt thereof), e.g., the cell or tissue is able to survive and grow despite exposure to (e.g., treatment with) an anti-cancer agent (e.g., dovitinib or a pharmaceutically acceptable salt thereof). Resistance may arise via exploitation by a cell or tissue of one or more of drug inactivation, drug target alteration, drug efflux, DNA damage repair, cell death inhibition, cell cycle regulation, epithelial-mesenchymal transition (EMT), epigenetics, and other mechanisms. A "resistant" cell or tissue refers to a cell (e.g., a cancer cell) or a tissue (e.g., a tumor), respectively, in vitro or in vivo (e.g., in a subject with a cancer, such as a human) that has acquired and/or exhibits resistance to a treatment (e.g., dovitinib or a pharmaceutically acceptable salt thereof). For example, a resistant cell or tissue is one that, upon exposure of the cell (e.g., a cancer cell) or the tissue (e.g., a tumor), respectively, to a cancer therapeutic (e.g., dovitinib or a pharmaceutically acceptable salt thereof) exhibits an inhibition in growth of the cell or tumor of less than 30%, 25%, 20%, 15%, 10%, 5%, or 1% relative to the growth of a cell or tissue not exposed to the treatment. Resistance to treatment may be determined by a cell proliferation assay, e.g., a cell-based assay, which measures the growth of treated cells as a function of the absorbance of the cells of an incident light beam, such as the NCI60 assays described herein. In this assay, greater absorbance indicates greater cell growth, and thus, resistance to the treatment.

The terms "sensitivity" and "responsiveness," as used herein, refer to the likelihood that a cancer treatment (e.g., dovitinib or a pharmaceutically acceptable salt thereof) has (e.g., induces) a desired effect, or alternatively refers to the strength of a desired effect caused or induced by the treatment in a cell (e.g., a cancer cell) or a tissue (e.g., a tumor) in vitro or in vivo (e.g., in a subject with a cancer, such as a human). For example, the desired effect can include inhibition of the growth of a cell (e.g., a cancer cell) in vitro by more than 30%, 35%, 40%, 45%, 50%, 55%, 60%, 65%, 70%, 75%, 80%, 85%, 90%, 95%, or 100% relative to the growth of a cell (e.g., a cancer cell) not exposed to the treatment. The desired effect can also include reduction in tumor mass by, e.g., about 30%, 35%, 40%, 45%, 50%, 55%, 60%, 65%, 70%, 75%, 80%, 85%, 90%, 95%, or 100%. "Sensitive" and "responsive" as used herein refer to a cell (e.g., a cancer cell) or a tissue (e.g., a tumor) in vitro or in vivo (e.g., in a subject with a cancer, such as a human) that is responsive to exposure to a therapeutic (e.g., dovitinib or a pharmaceutically acceptable salt thereof). Responsiveness to treatment may be determined by a cell proliferation assay, e.g., a cell-based assay, which measures the growth of treated cells as a function of the absorbance of the cells of an incident light beam, such as the NCI60 assays described herein. In this assay, lesser absorbance indicates lesser cell growth, and thus, sensitivity or responsiveness to the treatment. A greater reduction in growth indicates more sensitivity or responsiveness to the treatment.

The term "sample," as used herein, refers to any specimen (such as cells, tissue (e.g., a tissue sample obtained by biopsy), blood, serum, plasma, urine, cerebrospinal fluid, or pancreatic fluid) taken from a subject. Preferably, the sample is taken from a portion of the body affected by a cancer (e.g., a biopsy of the cancer tissue). Biopsy may involve fine needle aspiration biopsy, core needle biopsy (e.g., stereotactic core needle biopsy, vacuum-assisted core biopsy, or magnetic resonance imaging (MRI) guided biopsy), or surgical biopsy (e.g., incisional biopsy or excisional biopsy). The sample may undergo additional purification and processing, for example, to remove cell debris and other unwanted molecules. Additional processing may further involve amplification, e.g., using PCR (e.g., RT-PCR). The standard methods of sample purification, such as removal of unwanted molecules, are known in the art.

"Substantially similar" or "corresponds," as used herein with respect to a numerical value of a parameter of one or more of the biomarker(s) of sensitivity and/or resistance (e.g., biomarker expression level, difference score, or mean score), e.g., as determined in a test sample (e.g., a tumor biopsy) from a cancer patient, means that the numerical value of the parameter in the test sample is ±0-30% of the numerical value of the parameter in a reference sample (e.g., a cell (e.g., a cancer cell) or tissue (e.g., a tumor) known to be sensitive or resistant to dovitinib or a pharmaceutically acceptable salt thereof). For example, a numerical value of a parameter in a test sample may be substantially similar to, or may correspond to, the numerical value of the parameter in a reference sample if the parameter values of the test and reference samples differ by, e.g., less than 30%, less than 29%, less than 28%, less than 27%, less than 26%, less than 25%, less than 24%, less than 23%, less than 22%, less than 21%, less than 20%, less than 19%, less than 18%, less than 17%, less than 16%, less than 15%, less than 14%, less than 13%, less than 12%, less than 11%, less than 10%, less than 9%, less than 8%, less than 7%, less than 6%, less than 5%, less than 4%, less than 3%, less than 2%, or less than 1%.

"Substantially dissimilar," as used herein with respect to a numerical value of a parameter of one or more of the biomarker(s) of sensitivity and/or resistance (e.g., biomarker expression level, difference score, or mean score), e.g., as determined in a test sample (e.g., a tumor biopsy) from a cancer patient, means that the numerical value of the parameter in the test sample deviates by greater than 30% from the numerical value of the parameter in a reference sample (e.g., a cell (e.g., a cancer cell) or tissue (e.g., a tumor) known to be sensitive or resistant to dovitinib or a pharmaceutically acceptable salt thereof). For example, a numerical value of a parameter in a test sample may be substantially dissimilar to the numerical value of the parameter in a reference sample if the parameter values of the test and reference samples differ by, e.g., greater than 35%, 40%, 45%, 50%, 55%, 60%, 65%, 70%, 75%, 80%, 85%, 90%, 95%, 100% or more.

"Treatment," "medical treatment," to "treat," and "therapy," as used interchangeably herein, refer to administering or exposing a patient with a cancer (e.g., a human), a cancer cell, or a tumor to an anti-cancer agent (e.g., a drug, a protein, an antibody, a nucleic acid, a chemotherapeutic agent, or a radioactive agent), or to some other form of medical intervention used to treat or prevent a disease, disorder, or condition (e.g., surgery, cryotherapy, radiation therapy, or combinations thereof). In particular, a medical treatment can include dovitinib or a pharmaceutically acceptable salt thereof. For example, the cancer to be treated is a hematological cancer or a solid tumor. Examples of cancer include, e.g., myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, prostate cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), ovarian cancer (e.g., ovarian adenocarcinoma or embryonal carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), breast cancer (e.g., medullary carcinoma), ER-positive cancer, endometrial cancer, bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma, and basal cell carcinoma), thyroid cancer (e.g., papillary carcinoma and medullary carcinoma), brain cancer (e.g., astrocytoma and craniopharyngioma), stomach cancer, intra-epithelial cancer, bone cancer, biliary tract cancer, eye cancer, liver cancer (e.g., hepatocellular carcinoma or hepatoma), larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, or neoplasms of the central nervous system. Radiation therapy includes the administration of a radioactive agent to a patient or exposure of a patient to radiation. The radiation may be generated from sources such as particle accelerators and related medical devices or agents that emit, e.g., X-radiation, gamma radiation, or electron (Beta radiation) beams. A treatment may be or further include surgery, e.g., to remove a tumor from a subject or living organism.

Other features and advantages of the invention will be apparent from the following Detailed Description, the drawings, and the claims.

DETAILED DESCRIPTION OF THE INVENTION

Figure 1:
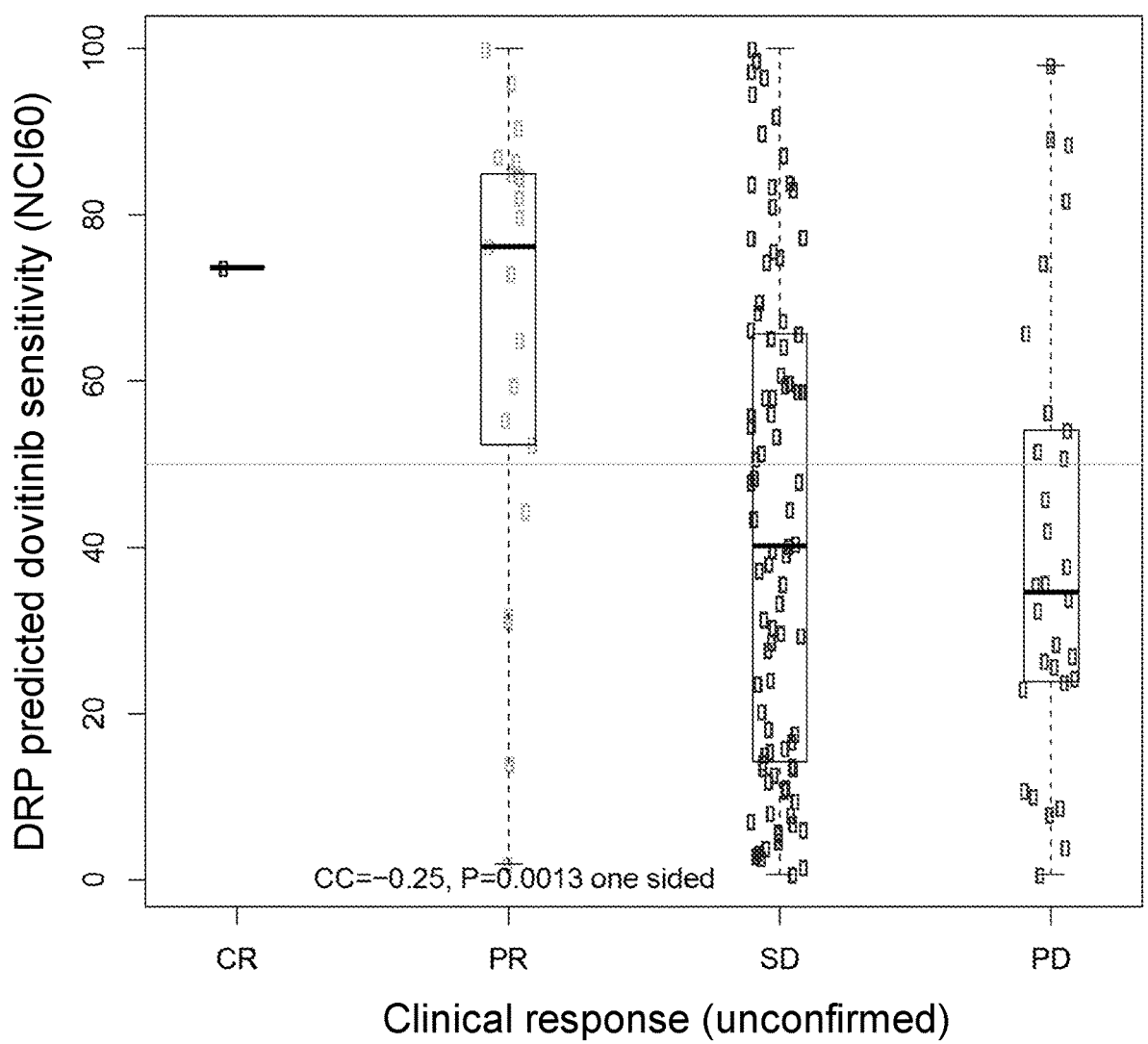
FIG. 1 is a graph showing comparison between drug response predictor (DRP) score and clinical response for five trials. A Pearson correlation between percentile score and clinical response (complete remission (CR)=1, partial response (PR)=2, stable disease (SD)=3, progressive disease (PD)=4, non-CR/non-PD=3, central evaluation without confirmation, where available) is −0.25, P=0.0013 one sided. The horizontal line shows a cutoff of 50. RCC, N=73; GIST, N=14; endometrial cancer, N=29; HCC, N=6; and breast cancer, N=19.

We have discovered that the expression levels of the biomarkers shown in Tables 2 and/or 3 can be used to determine whether a subject with a cancer will likely be responsive to dovitinib or a pharmaceutically acceptable salt thereof. A device, such as a microarray, with one or more single-stranded oligonucleotide probes that have substantial identity (e.g., at least 85%, 90%, 95%, 99%, or 100% sequence identity) to a sequence that is complementary or identical to the nucleic acid sequence of one or more (e.g., all) biomarkers shown in Tables 2 and/or 3 can be used according to the method described herein to assess the responsiveness of a cancer patient to treatment with dovitinib or a pharmaceutically acceptable salt thereof. For example, the probes can be used to detect one or more (e.g., two, three, four, five, ten, fifteen, twenty, twenty five, or all) of the biomarkers of sensitivity listed in Table 2, such as DDIT4 (SEQ ID NO: 1), in a sample (e.g., a tumor sample) from a patient having cancer. Additionally, the probes can be used to detect one or more (e.g., two, three, four, five, ten, fifteen, twenty, twenty five, or all) of the biomarkers of resistance listed in Table 3, such as SCAMP3 (SEQ ID NO: 31), in a sample (e.g., a tumor sample) from a patient having cancer. Accordingly, the invention features individual biomarkers (e.g., DDIT4 (SEQ ID NO: 1) or SCAMP3 (SEQ ID NO: 31)) and sets of biomarkers shown in Tables 2 and/or 3 that can be used to determine the responsiveness of a cancer patient to dovitinib or a pharmaceutically acceptable salt thereof at various stages of disease progression (e.g., patients diagnosed with cancer or patients after cancer recurrence) and at different times during the treatment process (e.g., prior to administration of any cancer treatment, after administration of one or more cancer treatments other than dovitinib or a pharmaceutically acceptable salt thereof, prior to administration of dovitinib or a pharmaceutically acceptable salt thereof, or during administration of dovitinib or a pharmaceutically acceptable salt thereof).

TABLE 2

Biomarkers of sensitivity to dovitinib. Dashes mean that the Affymetrix probeset has not been mapped to a specific gene. Affymetrix IDs refer to the array type HG-U11_Plus_2.

| Gene name | Affy ID | CC | Representative probe sequence | SEQ ID NO: |
|---|---|---|---|---|
| DDIT4 | 202887_s_at | 0.563 | GGCAGCTATCTTACAGACGCATGAA | 1 |
| ZNF395 | 218149_s_at | 0.331 | GTCCAGCGAATGACGTCTGTGGCCA | 2 |
| lncRNA | 216246_at | 0.326 | AGTCAATGAGTCGCTTGTGAATTCT | 3 |
| LSM4 | 202736_s_at | 0.307 | GAGCTGCGACAACTGGATGAACATT | 4 |
| SEL1L3 | 212314_at | 0.301 | TATTTTGGTACCTGTGCTTGCCACA | 5 |
| FAB P5 | 202345_s_at | 0.296 | CAACACAGTTTTCTTGTACCCTGGG | 6 |
| TRIM22 | 213293_s_at | 0.293 | TGAGGTCAAATTTTATCTTTTCACT | 7 |
| TPK1 | 221218_s_at | 0.293 | TCATTACTTTCTGCTTGACCGGAAG | 8 |
| SLC16A3 | 202856_s_at | 0.291 | GAGTGGATCTGCGGTGAAGCCAAGC | 9 |
| INSIG1 | 201626_at | 0.288 | CAATAAGTCTTTCTCTCCGAAACCG | 10 |
| HOXA10-HOXA9 HOXA9 MIR196B | 214651_s_at | 0.284 | AATGCGGGCATTTAAGTCTGTCCAT | 11 |
| DPP4 | 203716_s_at | 0.281 | AAAGCCCTGGTCGATGTTGGAGTGG | 12 |
| LDLR | 202068_s_at | 0.277 | AGAATGATGTCCCCGTTGTATGTAT | 13 |
| HSPE1 | 205133_s_at | 0.275 | TAGAAAGTTTCTTCCACTCTTTGAC | 14 |
| VEGFA | 212171_x_at | 0.274 | GGGAGACCTGGTTGTGTGTGTGTGAG | 15 |
| TMSB10 | 217733_s_at | 0.272 | AAGAGCCACCTGCAAGATGGACACG | 16 |
| SLC16A3 | 202855_s_at | 0.271 | TGTTCGTGGTGAGCTACGCCAAGGA | 17 |
| VEGFA | 210512_s_at | 0.271 | GAATTCTACATACTAAATCTCTCTC | 18 |
| CAV2 | 203323_at | 0.269 | GATGAGCAGACTTCTCGGAATTCAT | 19 |
| P4HA1 | 207543_s_at | 0.267 | AACTAGGACACTAACTGGGTTCCAT | 20 |

TABLE 2-continued

Biomarkers of sensitivity to dovitinib. Dashes mean that the Affymetrix probeset has not been mapped to a specific gene. Affymetrix IDs refer to the array type HG-U11_Plus_2.

| Gene name | Affy ID | CC | Representative probe sequence | SEQ ID NO: |
|---|---|---|---|---|
| APOL1 | 209546_s_at | 0.265 | GTCCCCTGCTTGAACACTGAAGGGC | 21 |
| CAV2 | 203324_s_at | 0.264 | AAATGTTGCTCTAATCAGATTGCTT | 22 |
| PTPRE | 221840_at | 0.263 | GACACCTGTGTTTCAGCATTTGGAG | 23 |
| DPYSL2 | 200762_at | 0.262 | GACCCATGAGTGGAGGAACTTTCAG | 24 |
| ANP32B | 201305_x_at | 0.262 | ATGACCTGCAGAAACAGAACTGTTC | 25 |
| STAT6 | 201331_s_at | 0.26 | GCTGGCACCTTAGTTGCATGACCAC | 26 |
| RPL27A SNORA3 | 203034_s_at | 0.259 | TCTGCCCAACTGTCAACCTTGACAA | 27 |
| EPB41L2 | 201719_s_at | 0.258 | GTTATACCATTTAAAGCTGGCACCA | 28 |
| RPL38 | 202028_s_at | 0.255 | AAAGGTATCTGCTGCATCGAACTTT | 29 |
| RNU86 RPL3 SNORD83B | 211073_x_at | 0.253 | TTAAGTTCATTGACACCACCTCCAA | 30 |

Note that VEGFA is targeted by two different probesets (SEQ ID NOs. 15 and 18), SLC16A3 is targeted by two probesets (SEQ ID NOs. 9 and 17), and CAV2 is targeted by two probesets (SEQ ID NOs. 19 and 22).

TABLE 3

Biomarkers of resistance to dovitinib. Dashes mean that the Affymetrix probeset has not been mapped to a specific gene. Affymetrix IDs refer to the array type HG-U133_Plus_2. All correlations are negative.

| Gene name | Affy ID | CC | Representative probe sequence | SEQ ID NO: |
|---|---|---|---|---|
| SCAMP3 | 201771_at | −0.397 | CTGCTCTGGTGGTGCCGAAGGGCAA | 31 |
| BAG5 | 202985_s_at | −0.329 | GATTGACTGTCAGGCATGGCTTTGT | 32 |
| ABCF1 | 200045_at | −0.325 | CTGATTTACCCTACAGCTTCAGGCC | 33 |
| MARCH6 | 201736_s_at | −0.313 | TAGCTTCTGGTGTTGTTCCTTTACT | 34 |
| EMC3 | 217882_at | −0.312 | GAGCTACTCACATTAGATGCATCCT | 35 |
| UCP2 | 208998_at | −0.304 | GAAAGTTCAGCCAGAATCTTCGTCC | 36 |
| TUG1 | 212337_at | −0.295 | ATACAGCAGTTCGAAAGCCGCGTCC | 37 |
| CLPTM1 | 211136_s_at | −0.286 | TTCATCTACCTCTACCAACGGTGGA | 38 |
| IGFBP5 | 211958_at | −0.285 | AGGAGGCTCCGTTTTGCAAAGTGGA | 39 |
| MAGEA1 | 207325_x_at | −0.278 | CTCAGTAGTAGGTTTCTGTTCTATT | 40 |
| ATM | 208442_s_at | −0.278 | CATTACGGGTGTTGAAGGTGTCTTC | 41 |
| GATA3 | 209602_s_at | −0.278 | CTG CTAGTCTTAAGAACTGCTTTCT | 42 |
| SPDEF | 220192_x_at | −0.278 | GGAAAACGGGCAGTCTGCTCTGCTG | 43 |
| LDOC1 | 204454_at | −0.276 | GCCGTTCAGCCTGGTTAGTTTTCTA | 44 |
| HRAS | 212983_at | −0.276 | GACTGTCTTGAACATCCCAAATGCC | 45 |
| SRM | 201516_at | −0.275 | TCGCCCACCAACCAAGTGTTACAAG | 46 |
| ZNF331 | 219228_at | −0.274 | CGCTTTCCACAGTTTGTTACCTGCA | 47 |
| GATA3 | 209604_s_at | −0.272 | GGACAAACTGCCAGTTTTGTTTCCT | 48 |
| TOB1 | 202704_at | −0.271 | CTCTCAGATATGGCCTCTTACAGTA | 49 |
| APITD1 CORT | 213454_at | −0.271 | CTTAAGCAAAATACTCCCAGGTCTC | 50 |
| NDUFV1 | 208714_at | −0.27 | GCACAGCTGCGGTGATCGTCATGGA | 51 |
| BAG6 | 213318_s_at | −0.27 | GTGGTATGCCTGCCAAGAGACGCAA | 52 |
| CUL3 | 201371_s_at | −0.269 | TATTCTTGGACTGTACTCTTCGCAT | 53 |
| CCDC90A | 220094_s_at | −0.268 | GAAATCATTGTGTCTGCATTGGTCA | 54 |
| CE R52 | 222212_s_at | −0.262 | GTAGGGGTTACAATTCACATTCCTT | 55 |
| LOC100506032 NBPF10 NBPF11 NBPF12 NBPF15 NBPF16 NBPF24 NBPF7 NBPF8 NBPF9 | 201103_x_at | −0.26 | GGTCTAGGAGATCTGTCCCTTTTAG | 56 |
| PPP1R11 | 201500_s_at | −0.258 | CCATACCACCACTGAGATCTCATTT | 57 |
| CKB | 200884_at | −0.254 | GAAGCGAGGCACAGGCGGTGTGGAC | 58 |

Note that GATA3 is targeted by two probesets (SEQ ID NOs. 42 and 48).

In particular, featured are methods for determining whether a patient may be responsive to dovitinib or a pharmaceutically acceptable salt thereof by, e.g., detecting the expression level (e.g., mRNA or protein expression level) of one or more of the biomarkers shown in Table(s) 2 and/or 3 (e.g., DDIT4 (SEQ ID NO: 1) and/or SCAMP3 (SEQ ID NO: 31)) in a biological sample (e.g., a tumor biopsy) obtained from the subject using a device (e.g., a microarray). The expression level of one or more of the biomarkers of sensitivity may then be compared to the expression level of the biomarker(s) in a cell or tissue known to be sensitive or resistant to dovitinib or a pharmaceutically acceptable salt thereof (e.g., a tumor sample from a reference subject having the same diagnosis as the patient and that has been determined to be sensitive or resistant to dovitinib or a pharmaceutically acceptable salt thereof) to determine the patient's responsiveness to dovitinib or a pharmaceutically acceptable salt thereof.

The patient may be responsive to dovitinib or a pharmaceutically acceptable salt thereof if the expression level of the one or more biomarkers of sensitivity (e.g., one or more of DDIT4 (SEQ ID NO: 1), ZNF395 (SEQ ID NO: 2), lncRNA (SEQ ID NO: 3), LSM4 (SEQ ID NO: 4), SEL1L3 (SEQ ID NO: 5), FABP5 (SEQ ID NO: 6), TRIM22 (SEQ ID NO: 7), TPK1 (SEQ ID NO: 8), SLC16A3 (SEQ ID NO: 9), INSIG1 (SEQ ID NO: 10), HOXA10-HOXA9 HOXA9 MIR196B (SEQ ID NO: 11), DPP4 (SEQ ID NO: 12), LDLR (SEQ ID NO: 13), HSPE1 (SEQ ID NO: 14), VEGFA (SEQ ID NO: 15), TMSB10 (SEQ ID NO: 16), SLC16A3 (SEQ ID NO: 17), VEGFA (SEQ ID NO: 18), CAV2 (SEQ ID NO: 19), P4HA1 (SEQ ID NO: 20), APOL1 (SEQ ID NO: 21), CAV2 (SEQ ID NO: 22), PTPRE (SEQ ID NO: 23), DPYSL2 (SEQ ID NO: 24), ANP32B (SEQ ID NO: 25), STAT6 (SEQ ID NO: 26), RPL27A SNORA3 (SEQ ID NO: 27), EPB41L2 (SEQ ID NO: 28), RPL38 (SEQ ID NO: 29), and RNU86 RPL3 SNORD83B (SEQ ID NO: 30)) is substantially similar to the expression level of the biomarker(s) of sensitivity in a cell (e.g., a cancer cell) or tissue (e.g., a tumor) known to be sensitive to dovitinib or a pharmaceutically acceptable salt thereof (e.g., a tumor sample from a reference subject having the same diagnosis as the patient and that has been determined to be responsive to dovitinib or a pharmaceutically acceptable salt thereof). The patient may also be responsive to dovitinib or a pharmaceutically acceptable salt thereof if the level of expression of one or more of the biomarkers of resistance (e.g., one or more of SCAMP3 (SEQ ID NO: 31), BAG5 (SEQ ID NO: 32), ABCF1 (SEQ ID NO: 33), MARCH6 (SEQ ID NO: 34), EMC3 (SEQ ID NO: 35), UCP2 (SEQ ID NO: 36), TUG1 (SEQ ID NO: 37), CLPTM1 (SEQ ID NO: 38), IGFBP5 (SEQ ID NO: 39), MAGEA1 (SEQ ID NO: 40), ATM (SEQ ID NO: 41), GATA3 (SEQ ID NO: 42), SPDEF (SEQ ID NO: 43), LDOC1 (SEQ ID NO: 44), HRAS (SEQ ID NO: 45), SRM (SEQ ID NO: 46), ZNF331 (SEQ ID NO: 47), GATA3 (SEQ ID NO: 48), TOB1 (SEQ ID NO: 49), APITD1 CORT (SEQ ID NO: 50), NDUFV1 (SEQ ID NO: 51), BAG6 (SEQ ID NO: 52), CUL3 (SEQ ID NO: 53), CCDC90A (SEQ ID NO: 54), CERS2 (SEQ ID NO: 55), LOC100506032 NBPF10 NBPF11 NBPF12 NBPF15 NBPF16 NBPF24 NBPF7 NBPF8 NBPF9 (SEQ ID NO: 56), PPP1R11 (SEQ ID NO: 57), and CKB (SEQ ID NO: 58)) is substantially similar to the expression level of the biomarker(s) of resistance in a cell or tissue known to be sensitive to dovitinib or a pharmaceutically acceptable salt thereof (e.g., a tumor sample from a reference subject having the same diagnosis as the patient and that has been determined to be responsive to dovitinib or a pharmaceutically acceptable salt thereof). The patient may also be responsive to dovitinib or a pharmaceutically acceptable salt thereof if the level of expression of one or more of the biomarkers of sensitivity is substantially dissimilar to the expression level of the biomarker(s) of sensitivity in a cell (e.g., a cancer cell) or tissue (e.g., a tumor) known to be resistant to dovitinib or a pharmaceutically acceptable salt thereof (e.g., a tumor sample from a reference subject having the same diagnosis as the patient and that has been determined to be resistant to dovitinib or a pharmaceutically acceptable salt thereof). Also, the patient may be responsive to dovitinib or a pharmaceutically acceptable salt thereof if the level of expression of one or more of the biomarkers of resistance is substantially dissimilar to the expression level of the biomarker(s) of resistance in a cell or tissue known to be resistant to dovitinib or a pharmaceutically acceptable salt thereof (e.g., a tumor sample from a reference subject having the same diagnosis as the patient and that has been determined to be resistant to dovitinib or a pharmaceutically acceptable salt thereof).

Also featured are methods of treating a patient with a cancer, such as a patient having recurrence of cancer, by detecting the expression levels of one or more of the biomarkers shown in Tables 2 and/or 3 (e.g., DDIT4 (SEQ ID NO: 1) and/or SCAMP5 (SEQ ID NO: 31)) in a sample (e.g., a tumor sample) from the patient, and then administering dovitinib or a pharmaceutically acceptable salt thereof based on the expression levels of the biomarker(s). In particular, a patient with a cancer may be administered dovitinib or a pharmaceutically acceptable salt thereof if the expression level of one or more biomarkers of sensitivity is substantially similar to the expression level of the biomarker(s) of sensitivity in a cell or tissue known to be sensitive to dovitinib or a pharmaceutically acceptable salt thereof. Moreover, a patient with a cancer may be administered dovitinib or a pharmaceutically acceptable salt thereof if the expression level of one or more biomarkers of resistance is substantially similar to the expression level of the biomarker(s) of resistance in a cell or tissue known to be sensitive to dovitinib or a pharmaceutically acceptable salt thereof. Additionally, a patient with a cancer may be administered dovitinib or a pharmaceutically acceptable salt thereof if the expression level of one or more biomarkers of sensitivity is substantially dissimilar to the expression level of the biomarker(s) of sensitivity in a cell or tissue known to be resistant to dovitinib or a pharmaceutically acceptable salt thereof. Also, a patient with a cancer may be administered dovitinib or a pharmaceutically acceptable salt thereof if the expression level of one or more biomarkers of resistance is substantially dissimilar to the expression level of the biomarker(s) of resistance in a cell or tissue known to be resistant to dovitinib or a pharmaceutically acceptable salt thereof. Thus, the methods can be used to treat a cancer patient predicted to be responsive to dovitinib or a pharmaceutically acceptable salt thereof, such as a patient with, e.g., multiple myeloma, breast cancer, acute myelogenous leukemia (AML), acute lympho-blastic leukemia (ALL), chronic lymphocytic leukemia (CLL), myelodysplastic syndrome (MDS), chronic myelogenous leukemia—chronic phase (CMLCP), diffuse large B-cell lymphoma (DLBCL), cutaneous T-cell lymphoma (CTCL), peripheral T-cell lymphoma (PTCL), Hodgkin's lymphoma, hepatocellular carcinoma (HCC), cervical cancer, prostate cancer, kidney cancer, renal cell carcinoma (RCC), esophageal cancer, melanoma, glioma, pancreatic cancer, ovarian cancer, gastrointestinal stromal tumors (GIST), sarcoma, breast cancer, estrogen receptor-positive (ERpos) breast cancer, metastatic breast cancer, endometrial cancer, lung cancer, non-small cell lung carcinoma (NSCLC), mesothelioma, intestinal cancer, colon cancer, bladder cancer, adrenal cancer, gallbladder cancer, or squamous cell carcinoma of the head and neck (SCCHN).

Methods are described herein for identifying biomarkers of drug responsiveness, detecting biomarker gene expression in a cancer patient, determining the responsiveness of a cancer patient to dovitinib or a pharmaceutically acceptable salt thereof, and treating cancer in a patient with dovitinib or a pharmaceutically acceptable salt thereof. Also described are devices and kits for use in these methods.

Methods for Identifying Biomarkers of Drug Responsiveness

Also featured are methods for identifying biomarkers (e.g., one or more of the biomarkers of Tables 2 and/or 3) that can be used to determine the responsiveness of a cancer patient to a cancer treatment, such as treatment with dovitinib or a pharmaceutically acceptable salt thereof. Such methods can involve, for example, an algorithm based on growth inhibition values (GI50) of cell lines (e.g., NCI60 cell lines) subjected to treatment with dovitinib or a pharmaceutically acceptable salt thereof, followed by measurement of gene expression (e.g., using a microarray (e.g., an Affymetrix HG-U133A Genechip array)).

Methodology of the In Vitro Cancer Growth Inhibition Screen

The human tumor cell lines of the cancer screening panel may be grown in RPMI 1640 medium containing 5% fetal bovine serum and 2 mM L-glutamine. Cells may be inoculated into 96 well microtiter plates in 100 μL at plating densities ranging from 5,000 to 40,000 cells/well depending on the doubling time of individual cell lines. After cell inoculation, the microtiter plates may be incubated at 37° C., 5% CO2, 95% air and 100% relative humidity for 24 hours prior to addition of experimental compounds.

After 24 hours, two plates of each cell line may be fixed in situ with TCA, to represent a measurement of the cell population for each cell line at the time of compound addition (Tz). Experimental compounds may be solubilized in dimethyl sulfoxide at 400-fold the desired final maximum test concentration and stored frozen prior to use. At the time of compound (e.g., dovitinib or a pharmaceutically acceptable salt thereof) addition, an aliquot of frozen concentrate may be thawed and diluted to twice the desired final maximum test concentration with complete medium containing 50 μg/ml Gentamicin. Additional four, 10-fold or ½ log serial dilutions are made to provide a total of five concentrations plus control. Aliquots of 100 μl of these different compound dilutions are added to the appropriate microtiter wells already containing 100 μl of medium, resulting in the required final compound concentrations.

Following compound (e.g., dovitinib or a pharmaceutically acceptable salt thereof) addition, the plates may be incubated for an additional 48 h at 37° C., 5% CO2, 95% air, and 100% relative humidity. For adherent cells, the assay may be terminated by the addition of cold TCA. Cells may be fixed in situ by the gentle addition of 50 μl of cold 50% (w/v) TCA (final concentration, 10% TCA) and incubated for 60 minutes at 4° C. The supernatant may be discarded, and the plates may be washed five times with tap water and air-dried. Sulforhodamine B (SRB) solution (100 μl) at 0.4% (w/v) in 1% acetic acid may be added to each well, and plates are incubated for 10 minutes at room temperature. After staining, unbound dye may be removed by washing five times with 1% acetic acid and the plates may be air-dried. Bound stain may be subsequently solubilized with 10 mM trizma base, and the absorbance may be read on an automated plate reader at a wavelength of 515 nm. For suspension cells, the methodology may be the same, except that the assay may be terminated by fixing settled cells at the bottom of the wells by gently adding 50 μl of 80% TCA (final concentration, 16% TCA). Using the seven absorbance measurements [time zero, (Tz), control growth, (C), and test growth in the presence of compound (e.g., dovitinib or a pharmaceutically acceptable salt thereof) at the five concentration levels (Ti)], the percentage growth may be calculated at each of the compound concentrations levels. Percentage growth inhibition may be calculated as:

$[(Ti-Tz)/(C \times Tz)] \times 100$ for concentrations for which $Ti >/= Tz$ $[(Ti-Tz)/Tz] \times 100$ for concentrations for which $Ti < Tz$ Three dose response parameters may be calculated for each experimental agent (e.g., dovitinib or a pharmaceutically acceptable salt thereof). Growth inhibition of 50% (GI50) is calculated from $[(Ti-Tz)/(C-Tz)] \times 100 = 50$, which is the agent (e.g., dovitinib) concentration resulting in a 50% reduction in the net protein increase (as measured by SRB staining) in control cells during the compound incubation. The compound concentration resulting in total growth inhibition (TGI) is calculated from Ti=Tz. The LC50 (concentration of compound resulting in a 50% reduction in the measured protein at the end of the compound treatment as compared to that at the beginning) indicating a net loss of cells following treatment is calculated from $[(Ti-Tz)/Tz] \times 100 = -50$. Values are calculated for each of these three parameters if the level of activity is reached; however, if the effect is not reached or is exceeded, the value for that parameter is expressed as greater or less than the maximum or minimum concentration tested.

Gene Expression and Growth Inhibition Analysis

The gene expression measurements of NCI60 cancer cell lines can be obtained from a publically available database (e.g., the National Cancer Institute and the Massachusetts Institute of Technology). Each dataset can be normalized so that sample expression measured by different chips can be compared. The preferred method of normalization is the logit transformation, which may be performed for each gene y on each chip, as follows:

$$\text{logit}(y) = \log[(y-\text{background})/(\text{saturation}-y)],$$

where background is calculated as the minimum intensity measured on the chip minus 0.1% of the signal intensity range: min−0.001*(max−min), and saturation is calculated as the maximum intensity measured on the chip plus 0.1% of the signal intensity range: max+0.001*(max−min). The resulting logit transformed data may then be z-transformed to mean zero and standard deviation 1.

Next, gene expression can be correlated to cancer cell growth inhibition. Growth inhibition data (GI50) of the NCI60 cell lines in the presence of a cancer treatment, such as dovitinib or a pharmaceutically acceptable salt thereof, can be obtained from the NCI. The correlation between the logit-transformed expression level of each gene in each cell line and the logarithm of GI50 (the concentration of a given compound that results in a 50% inhibition of growth) can be calculated, e.g., using the Pearson correlation coefficient or the Spearman Rank-Order correlation coefficient. Instead of using GI50s, any other measure of patient sensitivity to a given treatment (e.g., dovitinib or a pharmaceutically acceptable salt thereof) may be correlated to a gene expression levels of the patient. Since a plurality of measurements may be available for a single gene, the most accurate determination of correlation coefficient can be, e.g., the median of the correlation coefficients calculated for all probes measuring expression of the same gene.

For example, the median correlation coefficient of gene expression measured on a probe to growth inhibition or patient sensitivity to dovitinib or a pharmaceutically acceptable salt thereof can be calculated for all genes of interest. Genes that have a median correlation above, e.g., 0.25, 0.30, 0.31, 0.32, 0.33, 0.34, 0.35, 0.36, 0.37, 0.38, 0.39, 0.40, or higher, can be used as biomarkers of sensitivity for assessing responsiveness of a cancer patient (e.g., a patient have recurrence of cancer) to dovitinib or a pharmaceutically acceptable salt thereof. Likewise, genes that have a median correlation below, e.g., −0.25, −0.30, −0.31, −0.32, −0.33, −0.34, −0.35, −0.36, −0.37, −0.38, −0.39, −0.40, or lower, can be used as biomarkers of resistance for assessing responsiveness of a cancer patient (e.g., a patient have recurrence of cancer) to dovitinib or a pharmaceutically acceptable salt thereof. Preferably, the correlation coefficient of a biomarker of sensitivity will exceed 0.25, while the correlation coefficient of a biomarker of resistance will be less than −0.25. The result is a list of biomarker genes that correlate to sensitivity or resistance to dovitinib or a pharmaceutically acceptable salt thereof, as shown in Tables 2 and 3, respectively.

Cancer Types

The methods, devices, and kits of the invention can be used for diagnosing, prognosing, monitoring, treating, and/or reducing cancer in a subject suffering from, diagnosed with, or susceptible to cancer. Non-limiting examples of cancers that can be diagnosed, prognosed, monitored, treated, or reduced using the methods include hematological and solid tumors. In particular, cancers include, e.g., colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myeloma (e.g., multiple myeloma), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, prostate cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), ovarian cancer (e.g., ovarian adenocarcinoma or embryonal carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), breast cancer (e.g., medullary carcinoma), ER-positive cancer, bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma and basal cell carcinoma), thyroid cancer (e.g., papillary carcinoma and medullary carcinoma), brain cancer (e.g., astrocytoma and craniopharyngioma), stomach cancer, intra-epithelial cancer, bone cancer, biliary tract cancer, eye cancer, liver cancer (e.g., hepatocellular carcinoma or hepatoma), larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, and neoplasms of the central nervous system.

In particular, the methods are useful for diagnosing, prognosing, monitoring, treating, or preventing, e.g., multiple myeloma, breast cancer, acute myelogenous leukemia (AML), acute lympho-blastic leukemia (ALL), chronic lymphocytic leukemia (CLL), myelodysplastic syndrome (MDS), chronic myelogenous leukemia—chronic phase (CMLCP), diffuse large B-cell lymphoma (DLBCL), cutaneous T-cell lymphoma (CTCL), peripheral T-cell lymphoma (PTCL), Hodgkin's lymphoma, hepatocellular carcinoma (HCC), cervical cancer, prostate cancer, kidney cancer, renal cell carcinoma (RCC), esophageal cancer, melanoma, glioma, pancreatic cancer, ovarian cancer, gastrointestinal stromal tumors (GIST), sarcoma, breast cancer, estrogen receptor-positive (ERpos) breast cancer, metastatic breast cancer, endometrial cancer, lung cancer, non-small cell lung carcinoma (NSCLC), mesothelioma, intestinal cancer, colon cancer, bladder cancer, adrenal cancer, gallbladder cancer, and/or squamous cell carcinoma of the head and neck (SCCHN). For example, the cancer can be a breast cancer, such as medullary carcinoma. The cancer can be estrogen receptor-positive (ER pos) breast cancer. The cancer can be a metastatic form of breast cancer. The breast cancer can be, for example, a Stage 0, Stage I, Stage II, Stage III, or Stage IV breast cancer. Alternatively, the cancer can be endometrial cancer. In alternative embodiments, the cancer can be RCC. Alternatively, the cancer can be HCC. In alternative embodiments, the cancer can be GIST. Alternatively, the cancer can be lung cancer.

Methods for Detecting Biomarker Gene Expression in a Cancer Patient

A cancer patient can be assessed for sensitivity or resistance to dovitinib or a pharmaceutically acceptable salt thereof by detecting gene expression of a biomarker (e.g., one or more of the biomarkers of Tables 2 and/or 3) in a biological sample obtained from the cancer patient (e.g., a patient with the cancer or a recurrence thereof). The biological sample can include, for example, cells, tissue (e.g., a tissue sample obtained by biopsy), blood, serum, plasma, urine, sputum, cerebrospinal fluid, lymph tissue or fluid, or pancreatic fluid. For example, the biological sample can be fresh frozen or formalin-fixed paraffin embedded (FFPE) tissue obtained from the subject, such as a tumor sample (e.g., a biopsy) from the tissue of interest (e.g., lymph nodes, thymus, spleen, bone marrow, breast, colorectal, pancreatic, cervical, prostate, bladder, lung, gastrointestinal, head, neck, or ovarian tissue).

RNA Extraction and Biomarker Expression Measurement

Cell samples or tissue samples may be snap frozen in liquid nitrogen until processing. RNA may be extracted using, e.g., Trizol Reagent from Invitrogen following manufacturer's instructions, and detected directly or converted to cDNA for detection. RNA may be amplified using, e.g., MessageAmp kit from Ambion following manufacturer's instructions. Amplified RNA may be quantified using, e.g., HG-U133A or HG-U133_Plus2 GeneChip from Affymetrix Inc. and compatible apparatus e.g. GCS3000Dx from Affymetrix, using the manufacturer's instructions. The Affymetrix array typically contains 11 probes (also known as a probe set) specific to each gene. In general, confidence in a prediction of responsiveness or non-responsiveness increases with an increase in the number of probes used in the analysis. In Tables 2 and 3, a representative probe of the typical 11 probes is shown for each gene. The resulting biomarker expression measurements may be further analyzed as described herein. The procedures described can be implemented using, e.g., R software available from R-Project and supplemented with packages available from Bioconductor.

One or more of the biomarkers shown in Tables 2 and/or 3 (e.g., DDIT4 (SEQ ID NO: 1) and/or SCAMPS (SEQ ID NO: 31)) may be measured in a biological sample (e.g., a tumor sample) obtained from the cancer patient (e.g., a patient with any of the cancer types described herein, such as a patient with recurrence of cancer) using, e.g., polymerase chain reaction (PCR), reverse transcriptase PCR (RT-PCR), quantitative real-time PCR (qPCR), an array (e.g., a microarray), a genechip, pyrosequencing, nanopore sequencing, sequencing by synthesis, sequencing by expansion, single molecule real time technology, sequencing by ligation, microfluidics, infrared fluorescence, next generation sequencing (e.g., RNA-Seq techniques), Northern blots, Western blots, Southern blots, NanoString nCounter technologies (e.g., those described in U.S. Patent Application Nos. US 2011/0201515, US 2011/0229888, and US 2013/0017971, each of which is incorporated by reference in its entirety), proteomic techniques (e.g., mass spectrometry or protein arrays), and combinations thereof.

Devices

Devices of the invention can be used for detecting the level of expression of one or more biomarkers shown in Table(s) 2 and/or 3. The device may include at least one single-stranded nucleic acid (e.g., a probe) having at least 85% sequence identity (e.g., 85%, 90%, 95%, 97%, 98%, 99%, or 100% sequence identity) to a nucleic acid sequence that is complementary or identical to at least 5 (e.g., at least 10, at least 15, at least 20, or more) consecutive nucleotides of one or more biomarkers shown in Table(s) 2 and/or 3 (e.g., DDIT4 (SEQ ID NO: 1) or SCAMP3 (SEQ ID NO: 31)), in which the at least one single-stranded nucleic acid is sufficient for the detection of the level of expression of the one or more biomarkers. The device may be used to detect the expression level of a given biomarker by specific hybridization between the single-stranded nucleic acid and the biomarker (e.g., an mRNA, genomic DNA, or non-coding RNA), a nucleic acid encoding the biomarker (e.g., an mRNA), or a complementary nucleic acid thereof. The device may be, or may include, a microarray. The device may also include or be used with reagents and materials for next generation sequencing (e.g., sequencing by synthesis). The device may also include or be used with NanoString reagents and at least one nCounter cartridge. The device may be, or include a protein array, which contains one or more protein binding moieties (e.g., proteins, antibodies, nucleic acids, aptamers, affibodies, lipids, phospholipids, small molecules, labeled variants of any of the above, and any other moieties useful for protein detection as well known in the art) capable of detectably binding to the polypeptide product (s) of one or more biomarkers shown in Table(s) 2 and/or 3. For example, the device may have single-stranded nucleic acid molecule(s) having the sequence of or complementary to each of the biomarkers of sensitivity selected from the biomarkers of Table 2 and/or for each of the biomarkers of resistance selected from the biomarkers of Table 3 that are affixed to the device and can be used to detect the level of expression of the biomarkers, e.g., by hybridization.

Microarrays

The level of expression of the biomarkers (e.g., the biomarkers listed in Table(s) 2 and/or 3 (e.g., DDIT4 (SEQ ID NO: 1) or SCAMP3 (SEQ ID NO: 31)) may be determined using high-throughput expression profiling platforms, such as microarrays. In particular, a microarray for use in the methods for assessing the responsiveness of a subject with cancer (e.g., a patient with recurrence of cancer) to dovitinib or a pharmaceutically acceptable salt thereof contains or is produced by generating oligonucleotide probes (e.g., DNA, cDNA, or RNA probes) capable of hybridizing to one or more biomarkers of interest (e.g., one or more of the biomarkers of Table(s) 2 and/or 3) or the complement sequences thereof. Each probe can have, e.g., at least 10, 15, 20, 25, 30, or more contiguous nucleic acid residues (e.g., at least 15) that are complementary or identical to a nucleic acid sequence of a selected biomarker. The probe nucleic acid sequence can also have at least 85% (e.g., 90%, 95%, 99%, or 100%) sequence identity to the nucleic acid sequence of the gene coding the biomarker (e.g., DDIT4 (SEQ ID NO: 1)) or the complement sequence thereof. In particular, the probe sequences can be complementary to all or a portion of the nucleic acid sequence of the biomarker(s).

For example, microarrays of the invention for determining dovitinib (e.g., dovitinib or a pharmaceutically acceptable salt thereof) responsiveness can include probes for one or more (e.g., at least 5, 10, 15, or 20 (e.g., at least the top 5, 10, 15, or 20), or more (e.g., all)) biomarkers of sensitivity shown in Table 2, such as DDIT4 (SEQ ID NO: 1), ZNF395 (SEQ ID NO: 2), lncRNA (SEQ ID NO: 3), LSM4 (SEQ ID NO: 4), SEL1 L3 (SEQ ID NO: 5), FABP5 (SEQ ID NO: 6), TRIM22 (SEQ ID NO: 7), TPK1 (SEQ ID NO: 8), SLC16A3 (SEQ ID NO: 9), INSIG1 (SEQ ID NO: 10), HOXA10-HOXA9 HOXA9 MIR196B (SEQ ID NO: 11), DPP4 (SEQ ID NO: 12), LDLR (SEQ ID NO: 13), HSPE1 (SEQ ID NO: 14), VEGFA (SEQ ID NO: 15), TMSB10 (SEQ ID NO: 16), SLC16A3 (SEQ ID NO: 17), VEGFA (SEQ ID NO: 18), CAV2 (SEQ ID NO: 19), P4HA1 (SEQ ID NO: 20), APOL1 (SEQ ID NO: 21), CAV2 (SEQ ID NO: 22), PTPRE (SEQ ID NO: 23), DPYSL2 (SEQ ID NO: 24), ANP32B (SEQ ID NO: 25), STAT6 (SEQ ID NO: 26), RPL27A SNORA3 (SEQ ID NO: 27), EPB41 L2 (SEQ ID NO: 28), RPL38 (SEQ ID NO: 29), and RNU86 RPL3 SNORD83B (SEQ ID NO: 30).

Microarrays of the invention for determining dovitinib (e.g., dovitinib or a pharmaceutically acceptable salt thereof) responsiveness can also include probes for one or more (e.g., at least 5, 10, 15, or 20 (e.g., at least the top 5, 10, 15, or 20), or more (e.g., all)) biomarkers of resistance listed in Table 3, such as SCAMPS (SEQ ID NO: 31), BAGS (SEQ ID NO: 32), ABCF1 (SEQ ID NO: 33), MARCH6 (SEQ ID NO: 34), EMC3 (SEQ ID NO: 35), UCP2 (SEQ ID NO: 36), TUG1 (SEQ ID NO: 37), CLPTM1 (SEQ ID NO: 38), IGFBP5 (SEQ ID NO: 39), MAGEA1 (SEQ ID NO: 40), ATM (SEQ ID NO: 41), GATA3 (SEQ ID NO: 42), SPDEF (SEQ ID NO: 43), LDOC1 (SEQ ID NO: 44), HRAS (SEQ ID NO: 45), SRM (SEQ ID NO: 46), ZNF331 (SEQ ID NO: 47), GATA3 (SEQ ID NO: 48), TOB1 (SEQ ID NO: 49), APITD1 CORT (SEQ ID NO: 50), NDUFV1 (SEQ ID NO: 51), BAG6 (SEQ ID NO: 52), CUL3 (SEQ ID NO: 53), CCDC90A (SEQ ID NO: 54), CERS2 (SEQ ID NO: 55), LOC100506032 NBPF10 NBPF11 NBPF12 NBPF15 NBPF16 NBPF24 NBPF7 NBPF8 NBPF9 (SEQ ID NO: 56), PPP1R11 (SEQ ID NO: 57), and CKB (SEQ ID NO: 58).

A microarray probe may be single-stranded or double-stranded. The probe may be labeled (e.g., detectably labeled with a fluorescent molecule, dye molecule, small molecule, epitope tag, barcode sequence, polypeptide, or any other detectable molecule). Probes can be detectably labeled and immobilized on a solid support to form the microarray. For example, probes can be either prefabricated and spotted to the surface or directly synthesized on to the surface (in situ) of the microarray. The microarray can also be configured such that the sequence and position of each member (e.g., probe) of the array is known. For example, a selection of biomarkers whose expression correlates with an increased likelihood of responsiveness to dovitinib or a pharmaceutically acceptable salt thereof can be arrayed on a solid support. Hybridization of a labeled probe with a particular target nucleic acid (e.g., an mRNA corresponding to one or more biomarkers of Table(s) 2 and/or 3) indicates that the sample from which the mRNA was derived expresses that biomarker (e.g., the biomarker of sensitivity or resistance to dovitinib or a pharmaceutically acceptable salt thereof).

PCR-Based Techniques

As few as one and up to 25 or more of the biomarkers (e.g., 5 to 25 (e.g., the top 5 to 25) or 10 to 25 (e.g., the top 10 to 25), or at least the top 25 of the biomarkers listed in Table(s) 2 and/or 3) may be used to determine responsiveness of a cancer patient to dovitinib or a pharmaceutically acceptable salt thereof using the methods described herein. Tissue or cell samples from a cancer patient (e.g., a patient having recurrence of cancer) can be conveniently assayed for gene expression levels using nucleic acid amplification methods, such as polymerase chain reaction (PCR). Such PCR-based techniques may include reverse transcription PCR (RT-PCR), quantitative real-time PCR (qPCR), reverse transcription qPCR (RT-qPCR), or quantitative loop-mediated isothermal amplification (q-LAMP). For example, an mRNA corresponding to a biomarker of Table 2 or 3 can be detected in a biological sample by (a) producing cDNA from the sample by reverse transcription using at least one primer; (b) amplifying the cDNA so produced using a target polynucleotide as sense and antisense primers to amplify target cDNAs therein; and (c) detecting the presence of the amplified target cDNA using polynucleotide probes. The primers and probes including the target sequences shown in Table(s) 2 and/or 3, such as DDIT4 (SEQ ID NO: 1) and/or SCAMP3 (SEQ ID NO: 31), may be used to detect the level of expression of one or more of the indicated biomarkers using PCR. The methods can include one or more steps that allow determination of the levels of target mRNA in a biological sample (e.g., by simultaneously examining the levels of a comparative control mRNA sequence or "housekeeping" gene, such as an actin family member or GAPDH). The primers for these PCR-based techniques may be labeled for detection according to methods known in the art.

Sequencing

The level of expression of the biomarkers shown in Table(s) 2 and/or 3, such as DDIT4 (SEQ ID NO: 1) and/or SCAMP3 (SEQ ID NO: 31), may be determined using sequencing technologies, such as next generation sequencing platforms (e.g., RNA-Seq), as described in Mortazavi et al., *Nat. Methods* 5: 621-628, 2008, hereby incorporated by reference. RNA-Seq is a robust technology for monitoring expression by direct sequencing of the RNA molecules in a sample. This methodology may include fragmentation of RNA to an average length of, e.g., 200 nucleotides, conversion to cDNA by random priming, and synthesis of double-stranded cDNA (e.g., using the Just cDNA DoubleStranded cDNA Synthesis Kit from Agilent Technology). The cDNA may then be converted into a molecular library for sequencing by addition of sequence adapters for each library (e.g., from Illumina®/Solexa), and the resulting 50 to 100 nucleotide reads are mapped onto the genome. Exemplary sequencing platforms suitable for use according to the methods include, e.g., 454 pyrosequencing, Illumina sequencing by synthesis, SOLiD sequencing, Ion Torrent sequencing, and PacBio RS sequencing.

Methods of Determining the Responsiveness of a Patient to Dovitinib

The invention features diagnostic methods for the detection and screening of cancer patients (e.g., patients with cancer or a recurrence thereof) that may be responsive to dovitinib or a pharmaceutically acceptable salt thereof using one or more of the biomarkers shown in Table(s) 2 and/or 3 (e.g., DDIT4 (SEQ ID NO: 1) and/or SCAMP3 (SEQ ID NO: 31)). The methods of the invention may be used for predicting a patient's responsiveness to dovitinib or a pharmaceutically acceptable salt thereof, and optionally, treating the cancer patient throughout the progression of cancer and/or in cases of recurrence (e.g., after a first line treatment, a second line treatment, and/or a third line treatment).

The invention provides individual biomarkers (e.g., DDIT4 (SEQ ID NO: 1) or SCAMP3 (SEQ ID NO: 31)) and sets of biomarkers (e.g., two or more of the biomarkers listed in Table(s) 2 and/or 3), the expression levels of which, as detected in a biological sample (e.g., a tumor sample, such as a biopsy) obtained from a cancer patient (e.g., a human with cancer), are indicative of responsiveness to dovitinib or a pharmaceutically acceptable salt thereof. The biomarkers were identified using methods similar to those previously described in, e.g., Chen et al. (*Mol. Cancer Ther.* 11:34-33, 2012), Wang et al. (*J. Nat. Cancer Inst.* 105: 1284-1291, 2013), and Knudsen et al. (*PLoS One*, 9: e87415, 2014), Buhl et al (*PLoS One* 13(3):e0194609, 2018) each of which are incorporated by reference herein in their entirety. In particular, an algorithm based on growth inhibition values (GI50) of a cell line (e.g., NCI60 cells) is used. The cell line is subjected to treatment with dovitinib or a pharmaceutically acceptable salt thereof and baseline gene expression is determined (e.g., by microarray analysis, RT-PCR, qPCR, or next generation sequencing). After normalization, genes with, e.g., a Pearson correlation coefficient greater than 0.25 or below −0.25 can be classified as biomarkers of sensitivity or resistance, respectively. In particular, a correlation coefficient of 0.25 or greater is a statistically significant cut-off known in the art for establishing whether the expression levels of, e.g., the genes shown in Table(s) 2 and/or 3, correlate with the likelihood of cancer treatment sensitivity, such as sensitivity to dovitinib or a pharmaceutically acceptable salt thereof, as described in van't Veer et al. *Nature* 415(6871):530-536, 2002, hereby incorporated by reference.

Alternatively, after normalization, genes, or means of genes, or differences between means of genes, that have an expression level above a cutoff value of the $50^{th}$ percentile in a reference population with the same diagnosis as the patient, or greater (e.g., $60^{th}$ percentile, $70^{th}$ percentile, $80^{th}$ percentile, or $90^{th}$ percentile, or greater), indicates that the sample (or the subject from whom the sample was taken) is predicted to be responsive (e.g., for the biomarkers of sensitivity) or non-responsive (e.g., for the biomarkers of resistance), respectively, to the treatment, e.g., treatment with dovitinib or a pharmaceutically acceptable salt thereof.

Comparison of Biomarker Expression Levels

One or more biomarkers of sensitivity and/or resistance, identified as described herein, can be used to predict responsiveness to dovitinib or a pharmaceutically acceptable salt thereof by measuring the level of expression of the biomarker(s) in a biological sample obtained from the cancer patient. A single biomarker (e.g., any of the biomarkers of Table 2 or 3, such as DDIT4 (SEQ ID NO: 1) or SCAMP3 (SEQ ID NO: 31)) or a set of biomarkers (e.g., one, two, three, four, five, ten, fifteen, twenty, twenty five, or all of the biomarkers of Tables 2 and/or 3 (e.g., the top one, the top two, the top three, the top four, the top five, the top ten, the top fifteen, the top twenty, the top twenty five, or all of the biomarkers of Tables 2 and/or 3)) may be used to determine the responsiveness of a cancer patient (e.g., a patient with cancer recurrence) to dovitinib or a pharmaceutically acceptable salt thereof. After determining the level of expression of the biomarker(s) in a sample (e.g., a tumor sample) from the cancer patient, the level of expression of the biomarker(s) in the sample may be compared to the level of expression of the biomarker(s) in a cell (e.g., a cancer cell) or tissue (e.g., a tumor tissue) known to be sensitive to treatment with dovitinib or a pharmaceutically acceptable salt thereof. If the level of expression of the biomarker(s) in the sample from the cancer patient is substantially similar to the expression level of the biomarker(s) in the cell or tissue known to be sensitive to dovitinib or a pharmaceutically acceptable salt thereof, then the cancer patient is predicted to be responsive to treatment with dovitinib or a pharmaceutically acceptable salt thereof. Alternatively, if the expression level of the biomarker(s) in the sample from the cancer patient is substantially dissimilar to the expression level of the biomarker(s) in the cell or tissue known to be sensitive to dovitinib or a pharmaceutically acceptable salt thereof, then the cancer patient is predicted to be non-responsive to treatment with dovitinib or a pharmaceutically acceptable salt thereof.

The expression level of the biomarker(s) (e.g., DDIT4 (SEQ ID NO: 1) or SCAMP3 (SEQ ID NO: 31)) in a sample from the cancer patient may also be compared to the expression level of the biomarker(s) in a cell (e.g., a cancer cell) or tissue (e.g., a tumor tissue) known to be resistant to treatment with dovitinib or a pharmaceutically acceptable salt thereof. If the expression level of the biomarker(s) in the sample from the cancer patient is substantially similar to the expression level of the biomarker(s) in the cell or tissue known to be resistant to dovitinib or a pharmaceutically acceptable salt thereof, then the cancer patient is predicted to be non-responsive to treatment with dovitinib or a pharmaceutically acceptable salt thereof. Alternatively, if the expression level of the biomarker(s) in the sample from the cancer patient is substantially dissimilar to the expression level of the biomarker(s) in the cell or tissue known to be resistant to dovitinib or a pharmaceutically acceptable salt thereof, then the cancer patient is predicted to be responsive to treatment with dovitinib or a pharmaceutically acceptable salt thereof.

The responsiveness of a cancer patient (e.g., a patient with cancer recurrence) to dovitinib or a pharmaceutically acceptable salt thereof can also be predicted by comparing the expression level of a biomarker (e.g., DDIT4 (SEQ ID NO: 1) or SCAMP3 (SEQ ID NO: 31)) to the expression level of the biomarker in one or more cells or tissues (e.g., from a cancer patient population) known to be sensitive to treatment with dovitinib or a pharmaceutically acceptable salt thereof, and one or more cells or tissues (e.g., from a cancer patient population) known to be resistant to treatment with dovitinib or a pharmaceutically acceptable salt thereof. In particular, the patient may be responsive to treatment with dovitinib or a pharmaceutically acceptable salt thereof if the expression level of the biomarker(s) is substantially similar to the expression level of the biomarker(s) in a cell or tissue known to be sensitive to treatment with dovitinib or a pharmaceutically acceptable salt thereof, and if the expression level of the biomarker(s) is substantially dissimilar to the expression level of the biomarker(s) in a cell or tissue known to be resistant to treatment with dovitinib or a pharmaceutically acceptable salt thereof. Alternatively, the patient may be non-responsive to treatment with dovitinib or a pharmaceutically acceptable salt thereof if the expression level of the biomarker(s) is substantially similar to the expression level of the biomarker(s) in a cell or tissue known to be resistant to treatment with dovitinib or a pharmaceutically acceptable salt thereof, and if the expression level of the biomarker(s) is substantially dissimilar to the expression level of the biomarker(s) in a cell or tissue known to be sensitive to treatment with dovitinib or a pharmaceutically acceptable salt thereof.

Additionally, one or more biomarkers of sensitivity (e.g., one or more of DDIT4 (SEQ ID NO: 1), ZNF395 (SEQ ID NO: 2), lncRNA (SEQ ID NO: 3), LSM4 (SEQ ID NO: 4), SEL1 L3 (SEQ ID NO: 5), FABP5 (SEQ ID NO: 6), TRIM22 (SEQ ID NO: 7), TPK1 (SEQ ID NO: 8), SLC16A3 (SEQ ID NO: 9), INSIG1 (SEQ ID NO: 10), HOXA10-HOXA9 HOXA9 MIR196B (SEQ ID NO: 11), DPP4 (SEQ ID NO: 12), LDLR (SEQ ID NO: 13), HSPE1 (SEQ ID NO: 14), VEGFA (SEQ ID NO: 15), TMSB10 (SEQ ID NO: 16), SLC16A3 (SEQ ID NO: 17), VEGFA (SEQ ID NO: 18), CAV2 (SEQ ID NO: 19), P4HA1 (SEQ ID NO: 20), APOL1 (SEQ ID NO: 21), CAV2 (SEQ ID NO: 22), PTPRE (SEQ ID NO: 23), DPYSL2 (SEQ ID NO: 24), ANP32B (SEQ ID NO: 25), STAT6 (SEQ ID NO: 26), RPL27A SNORA3 (SEQ ID NO: 27), EPB41 L2 (SEQ ID NO: 28), RPL38 (SEQ ID NO: 29), and RNU86 RPL3 SNORD83B (SEQ ID NO: 30)) and one or more biomarkers of resistance (e.g., one or more of SCAMPS (SEQ ID NO: 31), BAGS (SEQ ID NO: 32), ABCF1 (SEQ ID NO: 33), MARCH6 (SEQ ID NO: 34), EMC3 (SEQ ID NO: 35), UCP2 (SEQ ID NO: 36), TUG1 (SEQ ID NO: 37), CLPTM1 (SEQ ID NO: 38), IGFBP5 (SEQ ID NO: 39), MAGEA1 (SEQ ID NO: 40), ATM (SEQ ID NO: 41), GATA3 (SEQ ID NO: 42), SPDEF (SEQ ID NO: 43), LDOC1 (SEQ ID NO: 44), HRAS (SEQ ID NO: 45), SRM (SEQ ID NO: 46), ZNF331 (SEQ ID NO: 47), GATA3 (SEQ ID NO: 48), TOB1 (SEQ ID NO: 49), APITD1 CORT (SEQ ID NO: 50), NDUFV1 (SEQ ID NO: 51), BAG6 (SEQ ID NO: 52), CUL3 (SEQ ID NO: 53), CCDC90A (SEQ ID NO: 54), CERS2 (SEQ ID NO: 55), LOC100506032 NBPF10 NBPF11 NBPF12 NBPF15 NBPF16 NBPF24 NBPF7 NBPF8 NBPF9 (SEQ ID NO: 56), PPP1R11 (SEQ ID NO: 57), and CKB (SEQ ID NO: 58)) may be used in combination to determine the responsiveness of a cancer patient (e.g., a patient with cancer recurrence) to treatment with dovitinib or a pharmaceutically acceptable salt thereof. For example, the predicted responsiveness of a cancer patient may be determined from, e.g., the difference score, which may be defined as the difference between the mean score (i.e., mean of the expression level) of the one or more biomarkers of sensitivity of Table 2 (e.g., DDIT4 (SEQ ID NO: 1)) and the mean score (i.e., mean of the expression level) of the one or more biomarkers of resistance of Table 3 (e.g., SCAMP3 (SEQ ID NO: 31)).

The difference score of the cancer patient can then be compared to the difference score in a cell (e.g., a cancer cell) or tissue (e.g., a tumor tissue) known to be sensitive or resistant to treatment with dovitinib or a pharmaceutically acceptable salt thereof. In particular, the patient may be responsive to treatment with dovitinib or a pharmaceutically acceptable salt thereof if the difference score is substantially similar to the difference score in a cell or tissue known to be sensitive to treatment with dovitinib or a pharmaceutically acceptable salt thereof. Additionally, the patient may be responsive to treatment with dovitinib or a pharmaceutically acceptable salt thereof if the difference score is substantially dissimilar to the difference score in a cell or tissue known to be resistant to treatment with dovitinib or a pharmaceutically acceptable salt thereof. Alternatively, the patient may be non-responsive to treatment with dovitinib or a pharmaceutically acceptable salt thereof if the difference score is substantially similar to the difference score in a cell or tissue known to be resistant to treatment with dovitinib or a pharmaceutically acceptable salt thereof. Moreover, the patient may be non-responsive to treatment with dovitinib or a pharmaceutically acceptable salt thereof if the difference score is substantially dissimilar to the difference score in a cell or tissue known to be sensitive to treatment with dovitinib or a pharmaceutically acceptable salt thereof.

Additionally, the patient may be responsive to treatment with dovitinib or a pharmaceutically acceptable salt thereof if the difference score is substantially similar to the difference score in a cell or tissue known to be sensitive to treatment with dovitinib or a pharmaceutically acceptable salt thereof, relative to the difference score in a cell or tissue known to be resistant to treatment with dovitinib or a pharmaceutically acceptable salt thereof. Also, the patient may be responsive to treatment with dovitinib or a pharmaceutically acceptable salt thereof if the difference score is substantially dissimilar to the difference score in a cell or tissue known to be resistant to treatment with dovitinib or a pharmaceutically acceptable salt thereof, relative to the difference score in a cell or tissue known to be sensitive to treatment with dovitinib or a pharmaceutically acceptable salt thereof. Alternatively, the patient may be non-responsive to treatment with dovitinib or a pharmaceutically acceptable salt thereof if the difference score is substantially similar to the difference score in a cell or tissue known to be resistant to treatment with dovitinib or a pharmaceutically acceptable salt thereof, relative to the difference score in a cell or tissue known to be sensitive to treatment with dovitinib or a pharmaceutically acceptable salt thereof. Furthermore, the patient may be non-responsive to treatment with dovitinib or a pharmaceutically acceptable salt thereof if the difference score is substantially dissimilar to the difference score in a cell or tissue known to be sensitive to treatment with dovitinib or a pharmaceutically acceptable salt thereof, relative to the difference score in a cell or tissue known to be resistant to treatment with dovitinib or a pharmaceutically acceptable salt thereof.

Additionally, the cancer patient (e.g., a patient with cancer recurrence) may be determined to be responsive to treatment with dovitinib or a pharmaceutically acceptable salt thereof if the difference score is compared to a score from a reference population (e.g., a score determined using a tumor sample(s) from subjects diagnosed with the same type(s) of tumor as the subject), in which an expression level at the $50^{th}$ percentile of the reference population, or the $60^{th}$ percentile, or the $70^{th}$ percentile, or the $80^{th}$ percentile, or the $90^{th}$ percentile, or greater, indicates that the sample (or the subject from whom the sample was taken) is predicted to be responsive to treatment with dovitinib or a pharmaceutically acceptable salt thereof. The confidence of the prediction increases as the percentile level increases (e.g., an expression level above the $90^{th}$ percentile of a reference population indicates a greater likelihood of treatment responsiveness than an expression level at the $50^{th}$ percentile). Conversely, an expression level in the tested sample of below the $50^{th}$ percentile of the reference population indicates that the sample (or the subject from whom the sample was taken) is predicted to be non-responsive to treatment with dovitinib or a pharmaceutically acceptable salt thereof.

Additionally, the mean score (i.e., mean of the expression level) of the one or more biomarkers of sensitivity of Table 2 and/or the mean score (i.e., mean of the expression level) of the one or more biomarkers of resistance of Table 3 can be used to predict responsiveness of a cancer patient (e.g., a patient with cancer recurrence) to dovitinib or a pharmaceutically acceptable salt thereof. After determining the mean score of the biomarker(s) in a sample (e.g., a tumor sample) from the cancer patient, the mean score of the biomarker(s) in the sample may be compared to the mean score of the biomarker(s) in a cell (e.g., a cancer cell) or tissue (e.g., a tumor tissue) known to be sensitive to treatment with dovitinib or a pharmaceutically acceptable salt thereof. If the mean score of the biomarker(s) in the sample from the cancer patient is substantially similar to the mean score of the biomarker(s) in the cell or tissue known to be sensitive to dovitinib or a pharmaceutically acceptable salt thereof, then the cancer patient is predicted to be responsive to treatment with dovitinib or a pharmaceutically acceptable salt thereof. Alternatively, if the mean score of the biomarker(s) in the sample from the cancer patient is substantially dissimilar to the mean score of the biomarker(s) in the cell or tissue known to be sensitive to dovitinib or a pharmaceutically acceptable salt thereof, then the cancer patient is predicted to be non-responsive to treatment with dovitinib or a pharmaceutically acceptable salt thereof.

The mean score (i.e., mean of the expression level) of the one or more biomarkers of sensitivity of Table 2 and/or the mean score (i.e., mean of the expression level) of the one or more biomarkers of resistance of Table 3 in a sample from the cancer patient may also be compared to the mean score of the biomarker(s) in a cell (e.g., a cancer cell) or tissue (e.g., a tumor tissue) known to be resistant to treatment with dovitinib or a pharmaceutically acceptable salt thereof. If the mean score of the biomarker(s) in the sample from the cancer patient is substantially similar to the mean score of the biomarker(s) in the cell or tissue known to be resistant to dovitinib or a pharmaceutically acceptable salt thereof, then the cancer patient is predicted to be non-responsive to treatment with dovitinib or a pharmaceutically acceptable salt thereof. Alternatively, if the mean score of the biomarker(s) in the sample from the cancer patient is substantially dissimilar to the mean score of the biomarker(s) in the cell or tissue known to be resistant to dovitinib or a pharmaceutically acceptable salt thereof, then the cancer patient is predicted to be responsive to treatment with dovitinib or a pharmaceutically acceptable salt thereof.

The responsiveness of a cancer patient (e.g., a patient with cancer recurrence) to dovitinib or a pharmaceutically acceptable salt thereof can also be predicted by comparing the mean score (i.e., mean of the expression level) of the one or more biomarkers of sensitivity of Table 2 and/or the mean score (i.e., mean of the expression level) of the one or more biomarkers of resistance of Table 3 in a sample from the cancer patient to the mean score of the biomarker(s) in one or more cells or tissues (e.g., from a cancer patient population) known to be sensitive to treatment with dovitinib or a pharmaceutically acceptable salt thereof and one or more cells or tissues (e.g., from a cancer patient population) known to be resistant to treatment with dovitinib or a pharmaceutically acceptable salt thereof. In particular, the patient may be responsive to treatment with dovitinib or a pharmaceutically acceptable salt thereof if the mean score of the biomarker(s) is substantially similar to the mean score of the biomarker(s) in a cell or tissue known to be sensitive to treatment with dovitinib or a pharmaceutically acceptable salt thereof, relative to the mean score in a cell or tissue known to be resistant to treatment with dovitinib or a pharmaceutically acceptable salt thereof. Additionally, the patient may be responsive to treatment with dovitinib or a pharmaceutically acceptable salt thereof if the mean score of the biomarker(s) is substantially dissimilar to the mean score of the biomarker(s) in a cell or tissue known to be resistant to treatment with dovitinib or a pharmaceutically acceptable salt thereof, relative to the mean score in a cell or tissue known to be sensitive to treatment with dovitinib or a pharmaceutically acceptable salt thereof.

Alternatively, the patient may be non-responsive to treatment with dovitinib or a pharmaceutically acceptable salt thereof if the mean score of the biomarker(s) is substantially similar to the mean score of the biomarker(s) in a cell or tissue known to be resistant to treatment with dovitinib or a pharmaceutically acceptable salt thereof, relative to the mean score in a cell or tissue known to be sensitive to treatment with dovitinib or a pharmaceutically acceptable salt thereof. Furthermore, the patient may be non-responsive to treatment with dovitinib or a pharmaceutically acceptable salt thereof if the mean score of the biomarker(s) is substantially dissimilar to the mean score of the biomarker(s) in a cell or tissue known to be sensitive to treatment with dovitinib or a pharmaceutically acceptable salt thereof, relative to the mean score in a cell or tissue known to be resistant to treatment with dovitinib or a pharmaceutically acceptable salt thereof.

In addition, the cancer patient (e.g., a patient with cancer recurrence) may be determined to be responsive to treatment with dovitinib or a pharmaceutically acceptable salt thereof if the mean score (i.e., mean of the expression level) of the one or more biomarkers of sensitivity of Table 2 is compared to a mean score from a reference population (e.g., a mean score determined using a tumor sample(s) from subjects diagnosed with the same type(s) of tumor as the subject), in which an expression level at the $50^{th}$ percentile of the reference population, or the $60^{th}$ percentile, or the $70^{th}$ percentile, or the $80^{th}$ percentile, or the $90^{th}$ percentile, or greater, indicates that the sample (or the subject from whom the sample was taken) is predicted to be responsive to treatment with dovitinib or a pharmaceutically acceptable salt thereof. The confidence of the prediction increases as the percentile level increases (e.g., an expression level above the $90^{th}$ percentile of a reference population indicates a greater likelihood of treatment responsiveness than an expression level at the $50^{th}$ percentile). Conversely, an expression level in the tested sample of below the $50^{th}$ percentile of the reference population indicates that the sample (or the subject from whom the sample was taken) is predicted to be non-responsive to treatment with dovitinib or a pharmaceutically acceptable salt thereof Additionally, the cancer patient (e.g., a patient with cancer recurrence) may be determined to be non-responsive to treatment with dovitinib or a pharmaceutically acceptable salt thereof if the mean score (i.e., mean of the expression level) of the one or more biomarkers of resistance of Table 3 is compared to a mean score from a reference population (e.g., a mean score determined using a tumor sample(s) from subjects diagnosed with the same type(s) of tumor as the subject), in which an expression level at the $50^{th}$ percentile of the reference population, or the $60^{th}$ percentile, or the $70^{th}$ percentile, or the $80^{th}$ percentile, or the $90^{th}$ percentile, or greater, indicates that the sample (or the subject from whom the sample was taken) is predicted to be non-responsive to treatment with dovitinib or a pharmaceutically acceptable salt thereof. The confidence of the prediction increases as the percentile level increases (e.g., an expression level above the $90^{th}$ percentile of a reference population indicates a greater likelihood of treatment non-responsiveness than an expression level at the $50^{th}$ percentile).

One or more biomarkers of sensitivity and/or resistance, identified as described herein, can be used to predict responsiveness to dovitinib or a pharmaceutically acceptable salt thereof by measuring the expression level of the biomarker(s) in a biological sample obtained from the cancer patient. A single biomarker (e.g., any of the biomarkers of Tables 2 and/or 3, such as DDIT4 (SEQ ID NO: 1) or SCAMPS (SEQ ID NO: 31)) or a set of biomarkers (e.g., one, two, three, four, five, ten, fifteen, twenty, twenty five, or all of the biomarkers of Tables 2 and/or 3 (e.g., the top one, the top two, the top three, the top four, the top five, the top ten, the top fifteen, the top twenty, the top twenty five, or all of the biomarkers of Tables 2 and/or 3)) may be used to determine the responsiveness of a cancer patient (e.g., a patient with cancer recurrence) to dovitinib or a pharmaceutically acceptable salt thereof. After determining the expression level of the biomarker(s) in a sample (e.g., a tumor sample) from the cancer patient, the expression level of the biomarker(s) in the sample may be compared to the expression level of the biomarker(s) in a cell (e.g., a cancer cell) or tissue (e.g., a tumor tissue) known to be sensitive to treatment with dovitinib or a pharmaceutically acceptable salt thereof. If the expression level of the biomarker(s) in the sample from the cancer patient corresponds to the expression level of the biomarker(s) in the cell or tissue known to be sensitive to dovitinib or a pharmaceutically acceptable salt thereof, then the cancer patient is predicted to be responsive to treatment with dovitinib or a pharmaceutically acceptable salt thereof. Alternatively, if the expression level of the biomarker(s) in the sample from the cancer patient is substantially dissimilar to the expression level of the biomarker(s) in the cell or tissue known to be sensitive to dovitinib or a pharmaceutically acceptable salt thereof, then the cancer patient is predicted to be non-responsive to treatment with dovitinib or a pharmaceutically acceptable salt thereof.

The expression level of the biomarker(s) (e.g., DDIT4 (SEQ ID NO: 1) and/or SCAMP3 (SEQ ID NO: 31)) in a sample from the cancer patient may also be compared to the expression level of the biomarker(s) in a cell (e.g., a cancer cell) or tissue (e.g., a tumor tissue) known to be resistant to treatment with dovitinib or a pharmaceutically acceptable salt thereof. If the expression level of the biomarker(s) in the sample from the cancer patient corresponds to the expression level of the biomarker(s) in the cell or tissue known to be resistant to dovitinib or a pharmaceutically acceptable salt thereof, then the cancer patient is predicted to be non-responsive to treatment with dovitinib or a pharmaceutically acceptable salt thereof. Alternatively, if the expression level of the biomarker(s) in the sample from the cancer patient is substantially dissimilar to the expression level of the biomarker(s) in the cell or tissue known to be resistant to dovitinib or a pharmaceutically acceptable salt thereof, then the cancer patient is predicted to be responsive to treatment with dovitinib.

The responsiveness of a cancer patient (e.g., a patient with cancer recurrence) to dovitinib or a pharmaceutically acceptable salt thereof can also be predicted by comparing the expression level of the biomarker(s) (e.g., DDIT4 (SEQ ID NO: 1) and/or SCAMP3 (SEQ ID NO: 31)) to the expression level of the biomarker(s) in one or more cells or tissues (e.g., from a cancer patient population, such as a cancer patient population having the same diagnosis as the cancer patient) known to be sensitive to treatment with dovitinib or a pharmaceutically acceptable salt thereof, and one or more cells or tissues (e.g., from a cancer patient population, such as a cancer patient population having the same diagnosis as the cancer patient) known to be resistant to treatment with dovitinib or a pharmaceutically acceptable salt thereof. In particular, the patient may be responsive to treatment with dovitinib or a pharmaceutically acceptable salt thereof if the expression level of the biomarker(s) corresponds to the expression level of the biomarker(s) in a cell or tissue known to be sensitive to treatment with dovitinib or a pharmaceutically acceptable salt thereof, relative to the expression level of the biomarker(s) in a cell or tissue known to be resistant to treatment with dovitinib or a pharmaceutically acceptable salt thereof. Moreover, the patient may be responsive to treatment with dovitinib or a pharmaceutically acceptable salt thereof if the expression level of the biomarker(s) is substantially dissimilar to the expression level of the biomarker(s) in a cell or tissue known to be resistant to treatment with dovitinib or a pharmaceutically acceptable salt thereof, relative to the expression level of the biomarker(s) in a cell or tissue known to be sensitive to treatment with dovitinib or a pharmaceutically acceptable salt thereof. Alternatively, the patient may be non-responsive to treatment with dovitinib or a pharmaceutically acceptable salt thereof if the expression level of the biomarker(s) corresponds to the expression level of the biomarker(s) in a cell or tissue known to be resistant to treatment with dovitinib or a pharmaceutically acceptable salt thereof, relative to the expression level of the biomarker(s) in a cell or tissue known to be sensitive to treatment with dovitinib or a pharmaceutically acceptable salt thereof. Also, the patient may be non-responsive to treatment with dovitinib or a pharmaceutically acceptable salt thereof if the expression level of the biomarker(s) is substantially dissimilar to the expression level of the biomarker(s) in a cell or tissue known to be sensitive to treatment with dovitinib or a pharmaceutically acceptable salt thereof, relative to the expression level of the biomarker(s) in a cell or tissue known to be resistant to treatment with dovitinib or a pharmaceutically acceptable salt thereof.

Additionally, one or more biomarkers of sensitivity (e.g., one or more of DDIT4 (SEQ ID NO: 1), ZNF395 (SEQ ID NO: 2), lncRNA (SEQ ID NO: 3), LSM4 (SEQ ID NO: 4), SEL1 L3 (SEQ ID NO: 5), FABP5 (SEQ ID NO: 6), TRIM22 (SEQ ID NO: 7), TPK1 (SEQ ID NO: 8), SLC16A3 (SEQ ID NO: 9), INSIG1 (SEQ ID NO: 10), HOXA10-HOXA9 HOXA9 MIR196B (SEQ ID NO: 11), DPP4 (SEQ ID NO: 12), LDLR (SEQ ID NO: 13), HSPE1 (SEQ ID NO: 14), VEGFA (SEQ ID NO: 15), TMSB10 (SEQ ID NO: 16), SLC16A3 (SEQ ID NO: 17), VEGFA (SEQ ID NO: 18), CAV2 (SEQ ID NO: 19), P4HA1 (SEQ ID NO: 20), APOL1 (SEQ ID NO: 21), CAV2 (SEQ ID NO: 22), PTPRE (SEQ ID NO: 23), DPYSL2 (SEQ ID NO: 24), ANP32B (SEQ ID NO: 25), STAT6 (SEQ ID NO: 26), RPL27A SNORA3 (SEQ ID NO: 27), EPB41 L2 (SEQ ID NO: 28), RPL38 (SEQ ID NO: 29), and RNU86 RPL3 SNORD83B (SEQ ID NO: 30)) and one or more biomarkers of resistance (e.g., one or more of SCAMP3 (SEQ ID NO: 31), BAGS (SEQ ID NO: 32), ABCF1 (SEQ ID NO: 33), MARCH6 (SEQ ID NO: 34), EMC3 (SEQ ID NO: 35), UCP2 (SEQ ID NO: 36), TUG1 (SEQ ID NO: 37), CLPTM1 (SEQ ID NO: 38), IGFBP5 (SEQ ID NO: 39), MAGEA1 (SEQ ID NO: 40), ATM (SEQ ID NO: 41), GATA3 (SEQ ID NO: 42), SPDEF (SEQ ID NO: 43), LDOC1 (SEQ ID NO: 44), HRAS (SEQ ID NO: 45), SRM (SEQ ID NO: 46), ZNF331 (SEQ ID NO: 47), GATA3 (SEQ ID NO: 48), TOB1 (SEQ ID NO: 49), APITD1 CORT (SEQ ID NO: 50), NDUFV1 (SEQ ID NO: 51), BAG6 (SEQ ID NO: 52), CUL3 (SEQ ID NO: 53), CCDC90A (SEQ ID NO: 54), CERS2 (SEQ ID NO: 55), LOC100506032 NBPF10 NBPF11 NBPF12 NBPF15 NBPF16 NBPF24 NBPF7 NBPF8 NBPF9 (SEQ ID NO: 56), PPP1R11 (SEQ ID NO: 57), and CKB (SEQ ID NO: 58)) may be used in combination to determine the responsiveness of a cancer patient (e.g., a patient with cancer recurrence) to treatment with dovitinib or a pharmaceutically acceptable salt thereof. For example, the predicted responsiveness of a cancer patient may be determined from, e.g., the difference score, which may be defined as the difference between the mean score (i.e., mean of the expression level) of the one or more biomarkers of sensitivity of Table 2 (e.g., DDIT4 (SEQ ID NO: 1)) and the mean score (i.e., mean of the expression level) of the one or more biomarkers of resistance of Table 3 (e.g., SCAMP3 (SEQ ID NO: 31)).

The difference score of the cancer patient can then be compared to the difference score in a cell (e.g., a cancer cell) or tissue (e.g., a tumor tissue) known to be sensitive or resistant to treatment with dovitinib or a pharmaceutically acceptable salt thereof. In particular, the patient may be responsive to treatment with dovitinib or a pharmaceutically acceptable salt thereof if the difference score corresponds to the difference score in a cell or tissue known to be sensitive to treatment with dovitinib or a pharmaceutically acceptable salt thereof. Additionally, the patient may be responsive to treatment with dovitinib or a pharmaceutically acceptable salt thereof if the difference score is substantially dissimilar to the difference score in a cell or tissue known to be resistant to treatment with dovitinib or a pharmaceutically acceptable salt thereof. Alternatively, the patient may be non-responsive to treatment with dovitinib or a pharmaceutically acceptable salt thereof if the difference score corresponds to the difference score in a cell or tissue known to be resistant to treatment with dovitinib or a pharmaceutically acceptable salt thereof. Also, the patient may be non-responsive to treatment with dovitinib or a pharmaceutically acceptable salt thereof if the difference score is substantially dissimilar to the difference score in a cell or tissue known to be sensitive to treatment with dovitinib or a pharmaceutically acceptable salt thereof.

Additionally, the patient may be responsive to treatment with dovitinib or a pharmaceutically acceptable salt thereof if the difference score corresponds to the difference score in a cell or tissue known to be sensitive to treatment with dovitinib or a pharmaceutically acceptable salt thereof, relative to the difference score in a cell or tissue known to be resistant to treatment with dovitinib or a pharmaceutically acceptable salt thereof. Furthermore, the patient may be responsive to treatment with dovitinib or a pharmaceutically acceptable salt thereof if the difference score is substantially dissimilar to the difference score in a cell or tissue known to be resistant to treatment with dovitinib or a pharmaceutically acceptable salt thereof, relative to the difference score in a cell or tissue known to be sensitive to treatment with dovitinib or a pharmaceutically acceptable salt thereof. Alternatively, the patient may be non-responsive to treatment with dovitinib or a pharmaceutically acceptable salt thereof if the difference score corresponds to the difference score in a cell or tissue known to be resistant to treatment with dovitinib or a pharmaceutically acceptable salt thereof, relative to the difference score in a cell or tissue known to be sensitive to treatment with dovitinib or a pharmaceutically acceptable salt thereof. Additionally, the patient may be non-responsive to treatment with dovitinib or a pharmaceutically acceptable salt thereof if the difference score is substantially dissimilar to the difference score in a cell or tissue known to be sensitive to treatment with dovitinib or a pharmaceutically acceptable salt thereof, relative to the difference score in a cell or tissue known to be resistant to treatment with dovitinib or a pharmaceutically acceptable salt thereof.

Alternatively, the patient may be determined to be responsive to treatment with dovitinib or a pharmaceutically acceptable salt thereof if the difference score is above a cutoff value of the $50^{th}$ percentile in a reference population with the same diagnosis as the patient, or greater (e.g., the difference score is above a cutoff value of the $60^{th}$ percentile, $70^{th}$ percentile, $80^{th}$ percentile, or $90^{th}$ percentile, or greater; see, e.g., FIG. 1).

Preferably, the cell or tissue known to be either sensitive or resistant to dovitinib or a pharmaceutically acceptable salt thereof is of the same cancer type as the cancer patient with an unknown responsiveness to dovitinib or a pharmaceutically acceptable salt thereof. For example, the cancer patient and the cell or tissue known to be either sensitive or resistant to dovitinib or a pharmaceutically acceptable salt thereof may both have a cancer type selected from a hematological cancer or a solid tumor, such as, e.g., myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, prostate cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), ovarian cancer (e.g., ovarian adenocarcinoma or embryonal carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), breast cancer (e.g., medullary carcinoma), ER-positive cancer, endometrial cancer, bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma and basal cell carcinoma), thyroid cancer (e.g., papillary carcinoma and medullary carcinoma), brain cancer (e.g., astrocytoma and craniopharyngioma), stomach cancer, intra-epithelial cancer, bone cancer, biliary tract cancer, eye cancer, liver cancer (e.g., hepatocellular carcinoma or hepatoma), larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, and neoplasms of the central nervous system. In particular, the cancer of the patient and the cell or tissue with known resistance or sensitivity to dovitinib or a pharmaceutically acceptable salt thereof is, e.g., multiple myeloma, breast cancer, acute myelogenous leukemia (AML), acute lymphoblastic leukemia (ALL), chronic lymphocytic leukemia (CLL), myelodysplastic syndrome (MDS), chronic myelogenous leukemia—chronic phase (CMLCP), diffuse large B-cell lymphoma (DLBCL), cutaneous T-cell lymphoma (CTCL), peripheral T-cell lymphoma (PTCL), Hodgkin's lymphoma, hepatocellular carcinoma (HCC), cervical cancer, prostate cancer, kidney cancer, renal cell carcinoma (RCC), esophageal cancer, melanoma, glioma, pancreatic cancer, ovarian cancer, gastrointestinal stromal tumors (GIST), sarcoma, breast cancer, estrogen receptor-positive (ERpos) breast cancer, metastatic breast cancer, endometrial cancer, lung cancer, non-small cell lung carcinoma (NSCLC), mesothelioma, intestinal cancer, colon cancer, bladder cancer, adrenal cancer, gallbladder cancer, or squamous cell carcinoma of the head and neck (SCCHN). In particular, the cancer of the patient and the cell or tissue with known resistance or sensitivity to dovitinib or a pharmaceutically acceptable salt thereof may be estrogen receptor-positive (ER pos) breast cancer. In particular instances, the cancer of the patient and the cell or tissue with known resistance or sensitivity to dovitinib or a pharmaceutically acceptable salt thereof may be a metastatic form of breast cancer. Alternatively, the cancer of the patient and the cell or tissue with known resistance or sensitivity to dovitinib or a pharmaceutically acceptable salt thereof may be endometrial cancer. In additional embodiments, the cancer of the patient and the cell or tissue with known resistance or sensitivity to dovitinib or a pharmaceutically acceptable salt thereof may be RCC. Alternatively, the cancer of the patient and the cell or tissue with known resistance or sensitivity to dovitinib or a pharmaceutically acceptable salt thereof may be HCC. In additional embodiments, the cancer of the patient and the cell or tissue with known resistance or sensitivity to dovitinib or a pharmaceutically acceptable salt thereof may be GIST. Alternatively, the cancer of the patient and the cell or tissue with known resistance or sensitivity to dovitinib or a pharmaceutically acceptable salt thereof may be lung cancer. The methods, devices, and kits described herein can be used to determine responsiveness of multiple types of cancer (e.g., breast cancer, endometrial cancer, RCC, HCC, GIST, lung cancer (e.g., non-small cell lung carcinoma), head and neck squamous cell carcinoma, melanoma, or others) to dovitinib or a pharmaceutically acceptable salt thereof. This is evident from the comparison of drug response predictor (DRP) score and clinical response depicted in FIG. 1, which shows aggregated data from clinical trials associated with different cancer types.

Also described herein is a method of determining responsiveness of multiple types of cancer (e.g., breast cancer, endometrial cancer, RCC, HCC, GIST, lung cancer (e.g., non-small cell lung carcinoma), head and neck squamous cell carcinoma, melanoma, or others) to an immune checkpoint inhibitor (e.g., a PD-1 inhibitor, a PD-L1 inhibitor, or a CTLA-4 inhibitor) that can be administered to a patient prior to, concurrently with, or after administration of dovitinib or a pharmaceutically acceptable salt thereof. This is evident from the comparison of DRP score of a three-gene biomarker of checkpoint inhibition and clinical response depicted in FIG. 3, which shows aggregated data from different types of solid tumors.

Machine learning techniques such as Neural Networks, Support Vector Machines, K Nearest Neighbor, and Nearest Centroids may also be employed to develop models that discriminate patients sensitive to treatment with dovitinib or a pharmaceutically acceptable salt thereof from those resistant to treatment with dovitinib or a pharmaceutically acceptable salt thereof using biomarker expression as model variables, which assign each patient a classification as sensitive or resistant to treatment with dovitinib or a pharmaceutically acceptable salt thereof. Machine learning techniques used to classify patients using various measurements are described in U.S. Pat. No. 5,822,715; U.S. Patent Application Publication Nos. 2003/0073083, 2005/0227266, 2005/0208512, 2005/0123945, 2003/0129629, and 2002/0006613; and in Vapnik V N. Statistical Learning Theory, John Wiley & Sons, New York, 1998; Hastie et al., 2001, The Elements of Statistical Learning: Data Mining, Inference, and Prediction, Springer, N.Y.; Agresti, 1996, An Introduction to Categorical Data Analysis, John Wiley & Sons, New York; V. Tresp et al., "Neural Network Modeling of Physiological Processes," in Hanson S. J. et al. (Eds.), Computational Learning Theory and Natural Learning Systems 2, MIT Press, 1994, each of which are hereby incorporated by reference in their entirety.

Biomarkers of Sensitivity and Resistance

The expression levels of one or more biomarkers of Table(s) 2 and/or 3 can be used to determine responsiveness of a cancer patient to treatment with dovitinib or a pharmaceutically acceptable salt thereof. In certain embodiments, the biomarker(s) of sensitivity can be selected from (a) one or more of SEQ ID NOs: 1-15; and/or (b) one or more of SEQ ID NOs: 16-30 from Table 2. Moreover, in certain embodiments, the biomarker(s) of resistance can be selected from (a) one or more of SEQ ID NOs: 31-45; and/or (b) one or more of SEQ ID NOs: 46-58 of Table 3. In particular embodiments, at least one (e.g., at least 1, at least 5, at least 10, at least 15, at least 20, at least 25, or at least 27 (e.g., at least the top 1, at least the top 5, at least the top 10, at least the top 15, at least the top 20, at least the top 25, or at least the top 27)) of the biomarkers of sensitivity of Table 2 and/or at least one (e.g., at least 1, at least 5, at least 10, at least 15, at least 20, at least 25, or at least 27 (e.g., at least the top 1, at least the top 5, at least the top 10, at least the top 15, at least the top 20, at least the top 25, or at least the top 27)) of the biomarkers of resistance of Table 3 can be used to determine responsiveness of a cancer patient to treatment with dovitinib or a pharmaceutically acceptable salt thereof. In more specific embodiments, one biomarker of sensitivity from Table 2 (e.g., DDIT4 (SEQ ID NO: 1)), and/or one biomarker of resistance from Table 3 (e.g., SCAMP3 (SEQ ID NO: 31)) can be used to determine responsiveness of a cancer patient to treatment with dovitinib or a pharmaceutically acceptable salt thereof. Once determined to be sensitive, the patient can be treated with dovitinib or a pharmaceutically acceptable salt thereof.

In particular, the biomarker of SEQ ID NO: 1 may be used to assess the responsiveness of a cancer patient (e.g., a patient with a cancer or a recurrence thereof) to dovitinib or a pharmaceutically acceptable salt thereof. The expression level of the biomarker of SEQ ID NO: 1 may be assessed using nucleic acid amplification methods (e.g., PCR) or a device (e.g., a microarray). As is described above, the expression level of the biomarker of SEQ ID NO: 1 in the patient sample may then be compared, e.g., to the expression level of the biomarker of SEQ ID NO: 1 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 1 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 2-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 2 may be used to assess the responsiveness of a cancer patient (e.g., a patient with a cancer or a recurrence thereof) to dovitinib or a pharmaceutically acceptable salt thereof. The expression level of the biomarker of SEQ ID NO: 2 may be assessed using nucleic acid amplification methods (e.g., PCR) or a device (e.g., a microarray). As is described above, the expression level of the biomarker of SEQ ID NO: 2 in the patient sample may then be compared, e.g., to the expression level of the biomarker of SEQ ID NO: 2 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 2 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1, 3-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 3 may be used to assess the responsiveness of a cancer patient (e.g., a patient with a cancer or a recurrence thereof) to dovitinib or a pharmaceutically acceptable salt thereof. The expression level of the biomarker of SEQ ID NO: 3 may be assessed using nucleic acid amplification methods (e.g., PCR) or a device (e.g., a microarray). As is described above, the expression level of the biomarker of SEQ ID NO: 3 in the patient sample may then be compared, e.g., to the expression level of the biomarker of SEQ ID NO: 3 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 3 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1, 2, 4-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 4 may be used to assess the responsiveness of a cancer patient (e.g., a patient with a cancer or a recurrence thereof) to dovitinib or a pharmaceutically acceptable salt thereof. The expression level of the biomarker of SEQ ID NO: 4 may be assessed using nucleic acid amplification methods (e.g., PCR) or a device (e.g., a microarray). As is described above, the expression level of the biomarker of SEQ ID NO: 4 in the patient sample may then be compared, e.g., to the expression level of the biomarker of SEQ ID NO: 4 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 4 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-3, 5-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 5 may be used to assess the responsiveness of a cancer patient (e.g., a patient with a cancer or a recurrence thereof) to dovitinib or a pharmaceutically acceptable salt thereof. The expression level of the biomarker of SEQ ID NO: 5 may be assessed using nucleic acid amplification methods (e.g., PCR) or a device (e.g., a microarray). As is described above, the expression level of the biomarker of SEQ ID NO: 5 in the patient sample may then be compared, e.g., to the expression level of the biomarker of SEQ ID NO: 5 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 5 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-4, 6-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 6 may be used to assess the responsiveness of a cancer patient (e.g., a patient with a cancer or a recurrence thereof) to dovitinib or a pharmaceutically acceptable salt thereof. The expression level of the biomarker of SEQ ID NO: 6 may be assessed using nucleic acid amplification methods (e.g., PCR) or a device (e.g., a microarray). As is described above, the expression level of the biomarker of SEQ ID NO: 6 in the patient sample may then be compared, e.g., to the expression level of the biomarker of SEQ ID NO: 6 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 6 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-5, 7-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 7 may be used to assess the responsiveness of a cancer patient (e.g., a patient with a cancer or a recurrence thereof) to dovitinib or a pharmaceutically acceptable salt thereof. The expression level of the biomarker of SEQ ID NO: 7 may be assessed using nucleic acid amplification methods (e.g., PCR) or a device (e.g., a microarray). As is described above, the expression level of the biomarker of SEQ ID NO: 7 in the patient sample may then be compared, e.g., to the expression level of the biomarker of SEQ ID NO: 7 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 7 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-6, 8-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 8 may be used to assess the responsiveness of a cancer patient (e.g., a patient with a cancer or a recurrence thereof) to dovitinib or a pharmaceutically acceptable salt thereof. The expression level of the biomarker of SEQ ID NO: 8 may be assessed using nucleic acid amplification methods (e.g., PCR) or a device (e.g., a microarray). As is described above, the expression level of the biomarker of SEQ ID NO: 8 in the patient sample may then be compared, e.g., to the expression level of the biomarker of SEQ ID NO: 8 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 8 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-7, 9-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 9 may be used to assess the responsiveness of a cancer patient (e.g., a patient with a cancer or a recurrence thereof) to dovitinib or a pharmaceutically acceptable salt thereof. The expression level of the biomarker of SEQ ID NO: 9 may be assessed using nucleic acid amplification methods (e.g., PCR) or a device (e.g., a microarray). As is described above, the expression level of the biomarker of SEQ ID NO: 9 in the patient sample may then be compared, e.g., to the expression level of the biomarker of SEQ ID NO: 9 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 9 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-8, 10-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 10 may be used to assess the responsiveness of a cancer patient (e.g., a patient with a cancer or a recurrence thereof) to dovitinib or a pharmaceutically acceptable salt thereof. The expression level of the biomarker of SEQ ID NO: 10 may be assessed using nucleic acid amplification methods (e.g., PCR) or a device (e.g., a microarray). As is described above, the expression level of the biomarker of SEQ ID NO: 10 in the patient sample may then be compared, e.g., to the expression level of the biomarker of SEQ ID NO: 10 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 10 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-9, 11-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 11 may be used to assess the responsiveness of a cancer patient (e.g., a patient with a cancer or a recurrence thereof) to dovitinib or a pharmaceutically acceptable salt thereof. The expression level of the biomarker of SEQ ID NO: 11 may be assessed using nucleic acid amplification methods (e.g., PCR) or a device (e.g., a microarray). As is described above, the expression level of the biomarker of SEQ ID NO: 11 in the patient sample may then be compared, e.g., to the expression level of the biomarker of SEQ ID NO: 11 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 11 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-10, 12-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 12 may be used to assess the responsiveness of a cancer patient (e.g., a patient with a cancer or a recurrence thereof) to dovitinib or a pharmaceutically acceptable salt thereof. The expression level of the biomarker of SEQ ID NO: 12 may be assessed using nucleic acid amplification methods (e.g., PCR) or a device (e.g., a microarray). As is described above, the expression level of the biomarker of SEQ ID NO: 12 in the patient sample may then be compared, e.g., to the expression level of the biomarker of SEQ ID NO: 12 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 12 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-11, 13-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 13 may be used to assess the responsiveness of a cancer patient (e.g., a patient with a cancer or a recurrence thereof) to dovitinib or a pharmaceutically acceptable salt thereof. The expression level of the biomarker of SEQ ID NO: 13 may be assessed using nucleic acid amplification methods (e.g., PCR) or a device (e.g., a microarray). As is described above, the expression level of the biomarker of SEQ ID NO: 13 in the patient sample may then be compared, e.g., to the expression level of the biomarker of SEQ ID NO: 13 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 13 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-12, 14-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 14 may be used to assess the responsiveness of a cancer patient (e.g., a patient with a cancer or a recurrence thereof) to dovitinib or a pharmaceutically acceptable salt thereof. The expression level of the biomarker of SEQ ID NO: 14 may be assessed using nucleic acid amplification methods (e.g., PCR) or a device (e.g., a microarray). As is described above, the expression level of the biomarker of SEQ ID NO: 14 in the patient sample may then be compared, e.g., to the expression level of the biomarker of SEQ ID NO: 14 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 14 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-13, 15-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 15 may be used to assess the responsiveness of a cancer patient (e.g., a patient with a cancer or a recurrence thereof) to dovitinib or a pharmaceutically acceptable salt thereof. The expression level of the biomarker of SEQ ID NO: 15 may be assessed using nucleic acid amplification methods (e.g., PCR) or a device (e.g., a microarray). As is described above, the expression level of the biomarker of SEQ ID NO: 15 in the patient sample may then be compared, e.g., to the expression level of the biomarker of SEQ ID NO: 15 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 15 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-14, 16-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 16 may be used to assess the responsiveness of a cancer patient (e.g., a patient with a cancer or a recurrence thereof) to dovitinib or a pharmaceutically acceptable salt thereof. The expression level of the biomarker of SEQ ID NO: 16 may be assessed using nucleic acid amplification methods (e.g., PCR) or a device (e.g., a microarray). As is described above, the expression level of the biomarker of SEQ ID NO: 16 in the patient sample may then be compared, e.g., to the expression level of the biomarker of SEQ ID NO: 16 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 16 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-15, 17-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 17 may be used to assess the responsiveness of a cancer patient (e.g., a patient with a cancer or a recurrence thereof) to dovitinib or a pharmaceutically acceptable salt thereof. The expression level of the biomarker of SEQ ID NO: 17 may be assessed using nucleic acid amplification methods (e.g., PCR) or a device (e.g., a microarray). As is described above, the expression level of the biomarker of SEQ ID NO: 17 in the patient sample may then be compared, e.g., to the expression level of the biomarker of SEQ ID NO: 17 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 17 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-16, 18-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 18 may be used to assess the responsiveness of a cancer patient (e.g., a patient with a cancer or a recurrence thereof) to dovitinib or a pharmaceutically acceptable salt thereof. The expression level of the biomarker of SEQ ID NO: 18 may be assessed using nucleic acid amplification methods (e.g., PCR) or a device (e.g., a microarray). As is described above, the expression level of the biomarker of SEQ ID NO: 18 in the patient sample may then be compared, e.g., to the expression level of the biomarker of SEQ ID NO: 18 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 18 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-17, 19-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 19 may be used to assess the responsiveness of a cancer patient (e.g., a patient with a cancer or a recurrence thereof) to dovitinib or a pharmaceutically acceptable salt thereof. The expression level of the biomarker of SEQ ID NO: 19 may be assessed using nucleic acid amplification methods (e.g., PCR) or a device (e.g., a microarray). As is described above, the expression level of the biomarker of SEQ ID NO: 19 in the patient sample may then be compared, e.g., to the expression level of the biomarker of SEQ ID NO: 19 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 19 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-18, 20-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 20 may be used to assess the responsiveness of a cancer patient (e.g., a patient with a cancer or a recurrence thereof) to dovitinib or a pharmaceutically acceptable salt thereof. The expression level of the biomarker of SEQ ID NO: 20 may be assessed using nucleic acid amplification methods (e.g., PCR) or a device (e.g., a microarray). As is described above, the expression level of the biomarker of SEQ ID NO: 20 in the patient sample may then be compared, e.g., to the expression level of the biomarker of SEQ ID NO: 20 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 20 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-19, 21-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 21 may be used to assess the responsiveness of a cancer patient (e.g., a patient with a cancer or a recurrence thereof) to dovitinib or a pharmaceutically acceptable salt thereof. The expression level of the biomarker of SEQ ID NO: 21 may be assessed using nucleic acid amplification methods (e.g., PCR) or a device (e.g., a microarray). As is described above, the expression level of the biomarker of SEQ ID NO: 21 in the patient sample may then be compared, e.g., to the expression level of the biomarker of SEQ ID NO: 21 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 21 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-20, 22-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 22 may be used to assess the responsiveness of a cancer patient (e.g., a patient with a cancer or a recurrence thereof) to dovitinib or a pharmaceutically acceptable salt thereof. The expression level of the biomarker of SEQ ID NO: 22 may be assessed using nucleic acid amplification methods (e.g., PCR) or a device (e.g., a microarray). As is described above, the expression level of the biomarker of SEQ ID NO: 22 in the patient sample may then be compared, e.g., to the expression level of the biomarker of SEQ ID NO: 22 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 22 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-21, 23-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 23 may be used to assess the responsiveness of a cancer patient (e.g., a patient with a cancer or a recurrence thereof) to dovitinib or a pharmaceutically acceptable salt thereof. The expression level of the biomarker of SEQ ID NO: 23 may be assessed using nucleic acid amplification methods (e.g., PCR) or a device (e.g., a microarray). As is described above, the expression level of the biomarker of SEQ ID NO: 23 in the patient sample may then be compared, e.g., to the expression level of the biomarker of SEQ ID NO: 23 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 23 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-22, 24-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 24 may be used to assess the responsiveness of a cancer patient (e.g., a patient with a cancer or a recurrence thereof) to dovitinib or a pharmaceutically acceptable salt thereof. The expression level of the biomarker of SEQ ID NO: 24 may be assessed using nucleic acid amplification methods (e.g., PCR) or a device (e.g., a microarray). As is described above, the expression level of the biomarker of SEQ ID NO: 24 in the patient sample may then be compared, e.g., to the expression level of the biomarker of SEQ ID NO: 24 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 24 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-23, 25-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 25 may be used to assess the responsiveness of a cancer patient (e.g., a patient with a cancer or a recurrence thereof) to dovitinib or a pharmaceutically acceptable salt thereof. The expression level of the biomarker of SEQ ID NO: 25 may be assessed using nucleic acid amplification methods (e.g., PCR) or a device (e.g., a microarray). As is described above, the expression level of the biomarker of SEQ ID NO: 25 in the patient sample may then be compared, e.g., to the expression level of the biomarker of SEQ ID NO: 25 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 25 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-24, 26-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 26 may be used to assess the responsiveness of a cancer patient (e.g., a patient with a cancer or a recurrence thereof) to dovitinib or a pharmaceutically acceptable salt thereof. The expression level of the biomarker of SEQ ID NO: 26 may be assessed using nucleic acid amplification methods (e.g., PCR) or a device (e.g., a microarray). As is described above, the expression level of the biomarker of SEQ ID NO: 26 in the patient sample may then be compared, e.g., to the expression level of the biomarker of SEQ ID NO: 26 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 26 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-25, 27-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 27 may be used to assess the responsiveness of a cancer patient (e.g., a patient with a cancer or a recurrence thereof) to dovitinib or a pharmaceutically acceptable salt thereof. The expression level of the biomarker of SEQ ID NO: 27 may be assessed using nucleic acid amplification methods (e.g., PCR) or a device (e.g., a microarray). As is described above, the expression level of the biomarker of SEQ ID NO: 27 in the patient sample may then be compared, e.g., to the expression level of the biomarker of SEQ ID NO: 27 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 27 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-26, 28-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 28 may be used to assess the responsiveness of a cancer patient (e.g., a patient with a cancer or a recurrence thereof) to dovitinib or a pharmaceutically acceptable salt thereof. The expression level of the biomarker of SEQ ID NO: 28 may be assessed using nucleic acid amplification methods (e.g., PCR) or a device (e.g., a microarray). As is described above, the expression level of the biomarker of SEQ ID NO: 28 in the patient sample may then be compared, e.g., to the expression level of the biomarker of SEQ ID NO: 28 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 28 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-27, 29-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 29 may be used to assess the responsiveness of a cancer patient (e.g., a patient with a cancer or a recurrence thereof) to dovitinib or a pharmaceutically acceptable salt thereof. The expression level of the biomarker of SEQ ID NO: 29 may be assessed using nucleic acid amplification methods (e.g., PCR) or a device (e.g., a microarray). As is described above, the expression level of the biomarker of SEQ ID NO: 29 in the patient sample may then be compared, e.g., to the expression level of the biomarker of SEQ ID NO: 29 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 29 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-28, 30-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 30 may be used to assess the responsiveness of a cancer patient (e.g., a patient with a cancer or a recurrence thereof) to dovitinib or a pharmaceutically acceptable salt thereof. The expression level of the biomarker of SEQ ID NO: 30 may be assessed using nucleic acid amplification methods (e.g., PCR) or a device (e.g., a microarray). As is described above, the expression level of the biomarker of SEQ ID NO: 30 in the patient sample may then be compared, e.g., to the expression level of the biomarker of SEQ ID NO: 30 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 30 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-29, 31-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 31 may be used to assess the responsiveness of a cancer patient (e.g., a patient with a cancer or a recurrence thereof) to dovitinib or a pharmaceutically acceptable salt thereof. The expression level of the biomarker of SEQ ID NO: 31 may be assessed using nucleic acid amplification methods (e.g., PCR) or a device (e.g., a microarray). As is described above, the expression level of the biomarker of SEQ ID NO: 31 in the patient sample may then be compared, e.g., to the expression level of the biomarker of SEQ ID NO: 31 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 31 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-30, 32-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 32 may be used to assess the responsiveness of a cancer patient (e.g., a patient with a cancer or a recurrence thereof) to dovitinib or a pharmaceutically acceptable salt thereof. The expression level of the biomarker of SEQ ID NO: 32 may be assessed using nucleic acid amplification methods (e.g., PCR) or a device (e.g., a microarray). As is described above, the expression level of the biomarker of SEQ ID NO: 32 in the patient sample may then be compared, e.g., to the expression level of the biomarker of SEQ ID NO: 32 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 32 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-31, 33-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 33 may be used to assess the responsiveness of a cancer patient (e.g., a patient with a cancer or a recurrence thereof) to dovitinib or a pharmaceutically acceptable salt thereof. The expression level of the biomarker of SEQ ID NO: 33 may be assessed using nucleic acid amplification methods (e.g., PCR) or a device (e.g., a microarray). As is described above, the expression level of the biomarker of SEQ ID NO: 33 in the patient sample may then be compared, e.g., to the expression level of the biomarker of SEQ ID NO: 33 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 33 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-32, 34-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 34 may be used to assess the responsiveness of a cancer patient (e.g., a patient with a cancer or a recurrence thereof) to dovitinib or a pharmaceutically acceptable salt thereof. The expression level of the biomarker of SEQ ID NO: 34 may be assessed using nucleic acid amplification methods (e.g., PCR) or a device (e.g., a microarray). As is described above, the expression level of the biomarker of SEQ ID NO: 34 in the patient sample may then be compared, e.g., to the expression level of the biomarker of SEQ ID NO: 34 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 34 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-33, 35-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 35 may be used to assess the responsiveness of a cancer patient (e.g., a patient with a cancer or a recurrence thereof) to dovitinib or a pharmaceutically acceptable salt thereof. The expression level of the biomarker of SEQ ID NO: 35 may be assessed using nucleic acid amplification methods (e.g., PCR) or a device (e.g., a microarray). As is described above, the expression level of the biomarker of SEQ ID NO: 35 in the patient sample may then be compared, e.g., to the expression level of the biomarker of SEQ ID NO: 35 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 35 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-34, 36-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 36 may be used to assess the responsiveness of a cancer patient (e.g., a patient with a cancer or a recurrence thereof) to dovitinib or a pharmaceutically acceptable salt thereof. The expression level of the biomarker of SEQ ID NO: 36 may be assessed using nucleic acid amplification methods (e.g., PCR) or a device (e.g., a microarray). As is described above, the expression level of the biomarker of SEQ ID NO: 36 in the patient sample may then be compared, e.g., to the expression level of the biomarker of SEQ ID NO: 36 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 36 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-35, 37-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 37 may be used to assess the responsiveness of a cancer patient (e.g., a patient with a cancer or a recurrence thereof) to dovitinib or a pharmaceutically acceptable salt thereof. The expression level of the biomarker of SEQ ID NO: 37 may be assessed using nucleic acid amplification methods (e.g., PCR) or a device (e.g., a microarray). As is described above, the expression level of the biomarker of SEQ ID NO: 37 in the patient sample may then be compared, e.g., to the expression level of the biomarker of SEQ ID NO: 37 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 37 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-36, 38-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 38 may be used to assess the responsiveness of a cancer patient (e.g., a patient with a cancer or a recurrence thereof) to dovitinib or a pharmaceutically acceptable salt thereof. The expression level of the biomarker of SEQ ID NO: 38 may be assessed using nucleic acid amplification methods (e.g., PCR) or a device (e.g., a microarray). As is described above, the expression level of the biomarker of SEQ ID NO: 38 in the patient sample may then be compared, e.g., to the expression level of the biomarker of SEQ ID NO: 38 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 38 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-37, 39-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 39 may be used to assess the responsiveness of a cancer patient (e.g., a patient with a cancer or a recurrence thereof) to dovitinib or a pharmaceutically acceptable salt thereof. The expression level of the biomarker of SEQ ID NO: 39 may be assessed using nucleic acid amplification methods (e.g., PCR) or a device (e.g., a microarray). As is described above, the expression level of the biomarker of SEQ ID NO: 39 in the patient sample may then be compared, e.g., to the expression level of the biomarker of SEQ ID NO: 39 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 39 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-38, 40-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 40 may be used to assess the responsiveness of a cancer patient (e.g., a patient with a cancer or a recurrence thereof) to dovitinib or a pharmaceutically acceptable salt thereof. The expression level of the biomarker of SEQ ID NO: 40 may be assessed using nucleic acid amplification methods (e.g., PCR) or a device (e.g., a microarray). As is described above, the expression level of the biomarker of SEQ ID NO: 40 in the patient sample may then be compared, e.g., to the expression level of the biomarker of SEQ ID NO: 40 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 40 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-39, 41-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 41 may be used to assess the responsiveness of a cancer patient (e.g., a patient with a cancer or a recurrence thereof) to dovitinib or a pharmaceutically acceptable salt thereof. The expression level of the biomarker of SEQ ID NO: 41 may be assessed using nucleic acid amplification methods (e.g., PCR) or a device (e.g., a microarray). As is described above, the expression level of the biomarker of SEQ ID NO: 41 in the patient sample may then be compared, e.g., to the expression level of the biomarker of SEQ ID NO: 41 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 41 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-40, 42-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 42 may be used to assess the responsiveness of a cancer patient (e.g., a patient with a cancer or a recurrence thereof) to dovitinib or a pharmaceutically acceptable salt thereof. The expression level of the biomarker of SEQ ID NO: 42 may be assessed using nucleic acid amplification methods (e.g., PCR) or a device (e.g., a microarray). As is described above, the expression level of the biomarker of SEQ ID NO: 42 in the patient sample may then be compared, e.g., to the expression level of the biomarker of SEQ ID NO: 42 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 42 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-41, 43-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 43 may be used to assess the responsiveness of a cancer patient (e.g., a patient with a cancer or a recurrence thereof) to dovitinib or a pharmaceutically acceptable salt thereof. The expression level of the biomarker of SEQ ID NO: 43 may be assessed using nucleic acid amplification methods (e.g., PCR) or a device (e.g., a microarray). As is described above, the expression level of the biomarker of SEQ ID NO: 43 in the patient sample may then be compared, e.g., to the expression level of the biomarker of SEQ ID NO: 43 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 43 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-42, 44-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 44 may be used to assess the responsiveness of a cancer patient (e.g., a patient with a cancer or a recurrence thereof) to dovitinib or a pharmaceutically acceptable salt thereof. The expression level of the biomarker of SEQ ID NO: 44 may be assessed using nucleic acid amplification methods (e.g., PCR) or a device (e.g., a microarray). As is described above, the expression level of the biomarker of SEQ ID NO: 44 in the patient sample may then be compared, e.g., to the expression level of the biomarker of SEQ ID NO: 44 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 44 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-43, 45-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 45 may be used to assess the responsiveness of a cancer patient (e.g., a patient with a cancer or a recurrence thereof) to dovitinib or a pharmaceutically acceptable salt thereof. The expression level of the biomarker of SEQ ID NO: 45 may be assessed using nucleic acid amplification methods (e.g., PCR) or a device (e.g., a microarray). As is described above, the expression level of the biomarker of SEQ ID NO: 45 in the patient sample may then be compared, e.g., to the expression level of the biomarker of SEQ ID NO: 45 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 45 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-44, 46-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 46 may be used to assess the responsiveness of a cancer patient (e.g., a patient with a cancer or a recurrence thereof) to dovitinib or a pharmaceutically acceptable salt thereof. The expression level of the biomarker of SEQ ID NO: 46 may be assessed using nucleic acid amplification methods (e.g., PCR) or a device (e.g., a microarray). As is described above, the expression level of the biomarker of SEQ ID NO: 46 in the patient sample may then be compared, e.g., to the expression level of the biomarker of SEQ ID NO: 46 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 46 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-45, 47-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 47 may be used to assess the responsiveness of a cancer patient (e.g., a patient with a cancer or a recurrence thereof) to dovitinib or a pharmaceutically acceptable salt thereof. The expression level of the biomarker of SEQ ID NO: 47 may be assessed using nucleic acid amplification methods (e.g., PCR) or a device (e.g., a microarray). As is described above, the expression level of the biomarker of SEQ ID NO: 47 in the patient sample may then be compared, e.g., to the expression level of the biomarker of SEQ ID NO: 47 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 47 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-46, 48-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 48 may be used to assess the responsiveness of a cancer patient (e.g., a patient with a cancer or a recurrence thereof) to dovitinib or a pharmaceutically acceptable salt thereof. The expression level of the biomarker of SEQ ID NO: 48 may be assessed using nucleic acid amplification methods (e.g., PCR) or a device (e.g., a microarray). As is described above, the expression level of the biomarker of SEQ ID NO: 48 in the patient sample may then be compared, e.g., to the expression level of the biomarker of SEQ ID NO: 48 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 48 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-47, 49-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 49 may be used to assess the responsiveness of a cancer patient (e.g., a patient with a cancer or a recurrence thereof) to dovitinib or a pharmaceutically acceptable salt thereof. The expression level of the biomarker of SEQ ID NO: 49 may be assessed using nucleic acid amplification methods (e.g., PCR) or a device (e.g., a microarray). As is described above, the expression level of the biomarker of SEQ ID NO: 49 in the patient sample may then be compared, e.g., to the expression level of the biomarker of SEQ ID NO: 49 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 49 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-48, 50-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 50 may be used to assess the responsiveness of a cancer patient (e.g., a patient with a cancer or a recurrence thereof) to dovitinib or a pharmaceutically acceptable salt thereof. The expression level of the biomarker of SEQ ID NO: 50 may be assessed using nucleic acid amplification methods (e.g., PCR) or a device (e.g., a microarray). As is described above, the expression level of the biomarker of SEQ ID NO: 50 in the patient sample may then be compared, e.g., to the expression level of the biomarker of SEQ ID NO: 50 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 50 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-49, 51-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 51 may be used to assess the responsiveness of a cancer patient (e.g., a patient with a cancer or a recurrence thereof) to dovitinib or a pharmaceutically acceptable salt thereof. The expression level of the biomarker of SEQ ID NO: 51 may be assessed using nucleic acid amplification methods (e.g., PCR) or a device (e.g., a microarray). As is described above, the expression level of the biomarker of SEQ ID NO: 51 in the patient sample may then be compared, e.g., to the expression level of the biomarker of SEQ ID NO: 51 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 51 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-50, 52-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 52 may be used to assess the responsiveness of a cancer patient (e.g., a patient with a cancer or a recurrence thereof) to dovitinib or a pharmaceutically acceptable salt thereof. The expression level of the biomarker of SEQ ID NO: 52 may be assessed using nucleic acid amplification methods (e.g., PCR) or a device (e.g., a microarray). As is described above, the expression level of the biomarker of SEQ ID NO: 52 in the patient sample may then be compared, e.g., to the expression level of the biomarker of SEQ ID NO: 52 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 52 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-51, 53-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 53 may be used to assess the responsiveness of a cancer patient (e.g., a patient with a cancer or a recurrence thereof) to dovitinib or a pharmaceutically acceptable salt thereof. The expression level of the biomarker of SEQ ID NO: 53 may be assessed using nucleic acid amplification methods (e.g., PCR) or a device (e.g., a microarray). As is described above, the expression level of the biomarker of SEQ ID NO: 53 in the patient sample may then be compared, e.g., to the expression level of the biomarker of SEQ ID NO: 53 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 53 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-52, 54-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 54 may be used to assess the responsiveness of a cancer patient (e.g., a patient with a cancer or a recurrence thereof) to dovitinib or a pharmaceutically acceptable salt thereof. The expression level of the biomarker of SEQ ID NO: 54 may be assessed using nucleic acid amplification methods (e.g., PCR) or a device (e.g., a microarray). As is described above, the expression level of the biomarker of SEQ ID NO: 54 in the patient sample may then be compared, e.g., to the expression level of the biomarker of SEQ ID NO: 54 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 54 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-53, 55-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 55 may be used to assess the responsiveness of a cancer patient (e.g., a patient with a cancer or a recurrence thereof) to dovitinib or a pharmaceutically acceptable salt thereof. The expression level of the biomarker of SEQ ID NO: 55 may be assessed using nucleic acid amplification methods (e.g., PCR) or a device (e.g., a microarray). As is described above, the expression level of the biomarker of SEQ ID NO: 55 in the patient sample may then be compared, e.g., to the expression level of the biomarker of SEQ ID NO: 55 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 55 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-54, 56-58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 56 may be used to assess the responsiveness of a cancer patient (e.g., a patient with a cancer or a recurrence thereof) to dovitinib or a pharmaceutically acceptable salt thereof. The expression level of the biomarker of SEQ ID NO: 56 may be assessed using nucleic acid amplification methods (e.g., PCR) or a device (e.g., a microarray). As is described above, the expression level of the biomarker of SEQ ID NO: 56 in the patient sample may then be compared, e.g., to the expression level of the biomarker of SEQ ID NO: 56 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 56 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-55, 57, 58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 57 may be used to assess the responsiveness of a cancer patient (e.g., a patient with a cancer or a recurrence thereof) to dovitinib or a pharmaceutically acceptable salt thereof. The expression level of the biomarker of SEQ ID NO: 57 may be assessed using nucleic acid amplification methods (e.g., PCR) or a device (e.g., a microarray). As is described above, the expression level of the biomarker of SEQ ID NO: 57 in the patient sample may then be compared, e.g., to the expression level of the biomarker of SEQ ID NO: 57 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 57 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-56, 58 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

The biomarker of SEQ ID NO: 58 may be used to assess the responsiveness of a cancer patient (e.g., a patient with a cancer or a recurrence thereof) to dovitinib or a pharmaceutically acceptable salt thereof. The expression level of the biomarker of SEQ ID NO: 58 may be assessed using nucleic acid amplification methods (e.g., PCR) or a device (e.g., a microarray). As is described above, the expression level of the biomarker of SEQ ID NO: 58 in the patient sample may then be compared, e.g., to the expression level of the biomarker of SEQ ID NO: 58 in a cell (e.g., a cancer cell) or tissue (e.g., a tumor tissue) known to be sensitive or resistant to treatment with dovitinib or a pharmaceutically acceptable salt thereof and used to determine the cancer patient's responsiveness to dovitinib or a pharmaceutically acceptable salt thereof. The biomarker of SEQ ID NO: 58 may be used alone or in combination with one or more additional biomarker(s) (e.g., one, two, three, four, five, ten, fifteen, twenty, twenty five, or all of the biomarkers shown in Tables 2 and/or 3 (e.g., the top one biomarker shown in Tables 2 and/or 3, the top two biomarker shown in Tables 2 and/or 3, the top three biomarkers shown in Tables 2 and/or 3, the top four biomarkers shown in Tables 2 and/or 3, the top five biomarkers shown in Tables 2 and/or 3, the top ten biomarkers shown in Tables 2 and/or 3, the top fifteen biomarkers shown in Tables 2 and/or 3, the top twenty biomarkers shown in Tables 2 and/or 3, the top twenty five biomarkers shown in Tables 2 and/or 3, or all of the biomarkers shown in Tables 2 and/or 3)), such as biomarker(s) of SEQ ID NOs: 1-57 to predict responsiveness of the cancer patient to treatment with dovitinib or a pharmaceutically acceptable salt thereof. The expression level of the biomarker(s) may be determined using, e.g., a microarray, PCR, or other techniques described herein, for example, using a nucleic acid probe sequence based on the target sequences shown in Tables 2 and 3.

Methods of Determining the Responsiveness of a Patient to an Immune Checkpoint Inhibitor Also described herein is a method of determining responsiveness of a patient to an immune checkpoint inhibitor, such as a PD-1 inhibitor (e.g., Pembrolizumab (KEYTRUDA®), Nivolumab (OPDIVO®), and Cemiplimab (LIBTAYO®)), a PD-L1 inhibitor (e.g., Atezolizumab (TECENTRIQ®), Avelumab (BAVENCIO®), and Durvalumab (IMFINZI®)), or a CTLA-4 inhibitor (e.g., Ipilimumab (YERVOY®), and Tremelimumab). Responsiveness of a patient (e.g., responsiveness of a tumor of a patient) to an immune checkpoint inhibitor (e.g., a PD-1 inhibitor, a PD-L1 inhibitor, a CTLA-4 inhibitor, or a FAS receptor inhibitor) can be determined based on an expression level one or more immune checkpoint biomarkers (e.g., PD-1, PD-L1, CTLA-4, and FAS receptor). The method can involve assessing the expression level of two, three or more of the immune checkpoint biomarkers. For example, a three-gene biomarker of checkpoint inhibition includes biomarkers for PD-1, PD-L1, and FAS receptor.

In some embodiments, an expression level of a three-gene biomarker of checkpoint inhibition includes an average of expression level of genes (e.g., PD-1 (e.g., SEQ ID NO: 59), PD-L1 (e.g., SEQ ID NO: 60), and FAS (e.g., SEQ ID NO: 61)) listed in Table 4.

In particular embodiments, the expression level of one or more biomarkers of immune checkpoint inhibition (e.g., a three-gene biomarker panel, such as a panel of PD-1, PD-L1, and FAS receptor) can be compared to the expression level of the biomarker(s) in a reference (e.g., the expression level of the biomarkers from a reference population of samples of tumors of the same type as those of a sample from a subject to be tested), in which the $50^{th}$ percentile of the reference, or the $60^{th}$ percentile, or the $70^{th}$ percentile, or the $80^{th}$ percentile, or the $90^{th}$ percentile, or greater, can be used to stratify tumors that are predicted to be responsive to an immune checkpoint inhibitor from tumors that are predicted to be non-response to an immune checkpoint inhibitor.

A drug response predictor (DRP) score for dovitinib can be combined with an immune checkpoint predictor score (e.g., an average of expression level of genes listed in Table 4 (e.g., PD-1 (e.g., SEQ ID NO: 59), PD-L1 (e.g., SEQ ID NO: 60), and FAS (e.g., SEQ ID NO: 61))) to identify a subject likely to respond to combination therapy with dovitinib and an immune checkpoint inhibitor. The dovitinib DRP and, e.g., the three-gene panel of checkpoint inhibition biomarkers can be given equal weight, for example by taking their average after normalization to a scale from zero to 100.

In some embodiments, a tumor of a patient (and, thus, the patient) determined to be responsive to immune checkpoint inhibitors by the methods described herein can be treated with one or more immune checkpoint inhibitors (e.g., one or more of a PD-1 inhibitor, a PD-L1 inhibitor, or a CTLA-4 inhibitor). In particular embodiments, a patient determined to be responsive to immune checkpoint inhibitors by the methods described herein can be treated with one or more immune checkpoint inhibitors (e.g., one or more of a PD-1 inhibitor, a PD-L1 inhibitor, or a CTLA-4 inhibitor) in combination with dovitinib or a pharmaceutically acceptable salt thereof. For example, a patient who is determined to be responsive to both (a) immune checkpoint inhibitors and (b) dovitinib or a pharmaceutically acceptable salt thereof by the methods described hereinabove, can be treated with a combination of (a) an immune checkpoint inhibitor (e.g., one or more of a PD-1 inhibitor, a PD-L1 inhibitor, or a CTLA-4 inhibitor) and (b) dovitinib or a pharmaceutically acceptable salt thereof.

Alternatively, a patient determined to be non-responsive to immune checkpoint inhibitors by the methods described herein can be treated with a therapeutic agent other than an immune checkpoint inhibitor, such as with one or more of an antiestrogen, an aromatase inhibitor, or an antigonadotropin. In particular embodiments, a patient determined to be non-responsive to immune checkpoint inhibitors by the methods described herein can be treated with a therapeutic agent other than an immune checkpoint inhibitor (e.g., one or more of an antiestrogen, an aromatase inhibitor, or an antigonadotropin) in combination with dovitinib or a pharmaceutically acceptable salt thereof. For example, a patient who is determined to be non-responsive to immune checkpoint inhibitors, but responsive to dovitinib or a pharmaceutically acceptable salt thereof by the methods described hereinabove, can be treated with a combination of a therapeutic agent other than an immune checkpoint inhibitor (e.g., one or more of an antiestrogen, an aromatase inhibitor, or an antigonadotropin) and dovitinib or a pharmaceutically acceptable salt thereof.

Methods of Treatment

The diagnostic methods of the invention permit the assessment of whether a patient is likely to be responsive to treatment with dovitinib or a pharmaceutically acceptable salt thereof, and can thus be used to direct the patient's treatment (e.g., as a first line therapy and/or as a second or third line therapy). A patient to be treated or tested for responsiveness to dovitinib or a pharmaceutically acceptable salt thereof according to the methods may include, e.g., a patient that has been diagnosed with cancer, a patient that has not received a cancer treatment (e.g., an anti-cancer agent other than dovitinib or a pharmaceutically acceptable salt thereof, or radiation), a patient that has received a cancer treatment (e.g., an anti-cancer agent other than dovitinib or radiation), or a patient during treatment with dovitinib or a pharmaceutically acceptable salt thereof. For example, the patient may have a hematological cancer or a solid tumor, such as a cancer type selected from myeloma (e.g., multiple myeloma), colorectal cancer (e.g., colon cancer and rectal cancer), leukemia (e.g., acute myeloid leukemia, acute lymphoid leukemia, chronic myeloid leukemia, chronic lymphocytic leukemia, acute myeloblastic leukemia, acute promyelocytic leukemia, acute myelomonocytic leukemia, acute monocytic leukemia, acute erythroleukemia, and chronic leukemia), myelodysplastic syndrome, lymphoma (e.g., diffuse large B-cell lymphoma, cutaneous T-cell lymphoma, peripheral T-cell lymphoma, Hodgkin's lymphoma, non-Hodgkin's lymphoma, Waldenstrom's macroglobulinemia, and lymphocytic lymphoma), cervical cancer, prostate cancer, esophageal cancer, melanoma, glioma (e.g., oligodendroglioma), pancreatic cancer (e.g., adenosquamous carcinoma, signet ring cell carcinoma, hepatoid carcinoma, colloid carcinoma, islet cell carcinoma, and pancreatic neuroendocrine carcinoma), ovarian cancer (e.g., ovarian adenocarcinoma or embryonal carcinoma), gastrointestinal stromal tumor, sarcoma (e.g., fibrosarcoma, myxosarcoma, liposarcoma, chondrosarcoma, osteogenic sarcoma, angiosarcoma, endotheliosarcoma, lymphangiosarcoma, lymphangioendotheliosarcoma, leiomyosarcoma, Ewing's sarcoma, and rhabdomyosarcoma), breast cancer (e.g., medullary carcinoma), ER-positive cancer, bladder cancer, head and neck cancer (e.g., squamous cell carcinoma of the head and neck), lung cancer (e.g., non-small cell lung carcinoma, large cell carcinoma, bronchogenic carcinoma, and papillary adenocarcinoma), metastatic cancer, oral cavity cancer, uterine cancer, testicular cancer (e.g., seminoma and embryonal carcinoma), skin cancer (e.g., squamous cell carcinoma and basal cell carcinoma), thyroid cancer (e.g., papillary carcinoma and medullary carcinoma), brain cancer (e.g., astrocytoma and craniopharyngioma), stomach cancer, intraepithelial cancer, bone cancer, biliary tract cancer, eye cancer, liver cancer (e.g., hepatocellular carcinoma or hepatoma), larynx cancer, kidney cancer (e.g., renal cell carcinoma and Wilms tumor), gastric cancer, blastoma (e.g., nephroblastoma, medulloblastoma, hemangioblastoma, neuroblastoma, and retinoblastoma), polycythemia vera, chordoma, synovioma, mesothelioma, adenocarcinoma, sweat gland carcinoma, sebaceous gland carcinoma, cystadenocarcinoma, bile duct carcinoma, choriocarcinoma, epithelial carcinoma, ependymoma, pinealoma, acoustic neuroma, schwannoma, meningioma, pituitary adenoma, nerve sheath tumor, cancer of the small intestine, cancer of the endocrine system, cancer of the penis, cancer of the urethra, cutaneous or intraocular melanoma, a gynecologic tumor, solid tumors of childhood, and neoplasms of the central nervous system. In particular, the cancer of the patient is, e.g., multiple myeloma, breast cancer, acute myelogenous leukemia (AML), acute lympho-blastic leukemia (ALL), chronic lymphocytic leukemia (CLL), myelodysplastic syndrome (MDS), chronic myelogenous leukemia—chronic phase (CMLCP), diffuse large B-cell lymphoma (DLBCL), cutaneous T-cell lymphoma (CTCL), peripheral T-cell lymphoma (PTCL), Hodgkin's lymphoma, hepatocellular carcinoma (HCC), cervical cancer, prostate cancer, kidney cancer, renal cell carcinoma (RCC), esophageal cancer, melanoma, glioma, pancreatic cancer, ovarian cancer, gastrointestinal stromal tumors (GIST), sarcoma, estrogen receptor-positive (ERpos) breast cancer, endometrial cancer, lung cancer, non-small cell lung carcinoma (NSCLC), mesothelioma, intestinal cancer, colon cancer, bladder cancer, adrenal cancer, gallbladder cancer, and squamous cell carcinoma of the head and neck (SCCHN). The patient may have estrogen receptor-positive (ER pos) breast cancer. The patient may also have a metastatic form of breast cancer. Alternatively, the patient may have endometrial cancer. In some embodiments, the patient may have RCC. In other embodiments, the patient may have HCC. Alternatively, the patient may have GIST. In alternative embodiments, the patient may have lung cancer. The patient may also have recurrence of cancer, such as a recurrent form of any of the above cancer types, e.g., recurrent breast cancer, recurrent endometrial cancer, recurrent RCC, recurrent HCC, recurrent GIST, or recurrent lung cancer.

A patient found to be responsive to dovitinib or a pharmaceutically acceptable salt thereof according to the methods of the invention may be preferentially selected for treatment with dovitinib or a pharmaceutically acceptable salt thereof. For example, a patient can be identified as responsive to dovitinib or a pharmaceutically acceptable salt thereof by determining the expression level of one or more biomarkers (e.g., one or more of the biomarkers shown in Table(s) 2 and/or 3, such as DDIT4 (SEQ ID NO: 1) and/or SCAMP5 (SEQ ID NO: 31)) in a biological sample (e.g., a tumor sample) obtained from the patient, and subsequently administered dovitinib or a pharmaceutically acceptable salt thereof. One or more additional therapies (e.g., surgery, radiation, or a therapeutic agent) may also be administered to the patient prior to, concurrently with, or after administration of dovitinib or a pharmaceutically acceptable salt thereof. A therapeutic agent that can be administered to the patient prior to, concurrently with, or after administration of dovitinib or a pharmaceutically acceptable salt thereof may be one or more of a histone deacetylase (HDAC) inhibitor, an immune checkpoint inhibitor, an antiestrogen, an aromatase inhibitor, an antigonadotropin, a proteasome inhibitor, an immunomodulator, a glucocorticoid, a folic acid, a monoclonal antibody, or an antineoplastic agent. In particular, a therapeutic agent that can be administered to the patient prior to, concurrently with, or after administration of dovitinib or a pharmaceutically acceptable salt thereof may be one or more of a HDAC inhibitor, an immune checkpoint inhibitor (e.g., a PD1 inhibitor (e.g., Pembrolizumab (KEYTRUDA®), Nivolumab (OPDIVO®), and Cemiplimab (LIBTAYO®)), a PD-L1 inhibitor (e.g., Atezolizumab (TECENTRIQ®), Avelumab (BAVENCIO®), and Durvalumab (IMFINZI®)), and a CTLA-4 inhibitor (e.g., Ipilimumab (YERVOY®), and Tremelimumab)), an aromatase inhibitor (e.g., a non-selective aromatase inhibitor, such as Aminoglutethimide and Testolactone (TESLAC®), a selective aromatase inhibitor, such as anastrozole (ARIMIDEX®), letrozole (FEMARA®), exemestane (AROMASIN®), vorozole (RIVIZOR®), formestane (LENTARON®), and fadrozole (AFEMA®), and other aromatase inhibitors, such as 1,4,6-Androstatrien-3,17-dione (ATD) and 4-Androstene-3,6,17-trione (6-OXO)), an antiestrogen (e.g., a selective estrogen receptor modulator (SERM) (e.g., tamoxifen, clomifene, and raloxifene), an estrogen receptor silent antagonist, and selective estrogen receptor degrader (SERD) (e.g., fulvestrant (FASLODEX®))), an antigonadotropin (e.g., gonadotropin-releasing hormone (GnRH) analogue, compounds acting on sex steroid hormone receptors (e.g., progestogens, androgens, and estrogens), and steroid synthesis inhibitors (e.g., danazol and gestrinone)), a cyclin-dependent kinase inhibitor (e.g., a CDK inhibitor selective for CDK4 and CDK6, such as palbociclib (IBRANCE®) and abemaciclib (VERZENIO®, VERZENIOS®)), venetoclax (VENCLEXTA®, VENCLYXTO®), ibrutinib (IMBRUVICA®), bortezomib, carfilzomib, thalidomide, lenalidomide, pomalidomide, prednisone, dexamethasone, cyclophosphamide, vincristine, doxorubicin, melphalan, capecitabine, tegafur, irinotecan, oxaliplatin, cetuximab, leucovorin, SN-38, everolimus, temsirolimus, bleomycin, lomustine, depsipeptide, carboplatin, erlotinib, gemcitabine, mitoxantrone, cisplatin, busulfan, epirubicin, arsenic trioxide, bendamustine, teniposide, adriamycin, decitabine, estramustine, etoposide, azaguanine, aclarubicin, mitoxantrone, mitomycin, paclitaxel, taxotere, Irofulven, 5-FU, ara-c, methylprednisolone, methotrexate, methyl-gag, belinostat, carboplatin, idarubicin, IL4-PR38, valproic acid, all-trans retinoic acid (ATRA), cytoxan, topotecan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, floxuridine, thioguanine, PSC 833, herceptin, bevacizumab, celecoxib, iressa, anastrozole, letrozole, and rituximab.

In some embodiments the therapeutic agent may be an immune checkpoint inhibitor, such as a PD1 inhibitor, a PD-L1 inhibitor, or a CTLA-4 inhibitor. The combination of a multi tyrosine kinase inhibitor (e.g., Lenvatinib (LENVIMA®)) with an immune checkpoint inhibitor (e.g., a PD1 inhibitor, such as Pembrolizumab (KEYTRUDA®)) is an established approach to obtaining superior treatment benefit to a patient. Dovitinib can also be combined with a number of immune checkpoint inhibitors, such as PD-1 inhibitors, PD-L1 inhibitors, or CTLA-4 inhibitors. For example, a PD1 inhibitor (e.g., Pembrolizumab (KEYTRUDA®), Nivolumab (OPDIVO®), and Cemiplimab (LIBTAYO®)), a PD-L1 inhibitor (e.g., Atezolizumab (TECENTRIQ®), Avelumab (BAVENCIO®), and Durvalumab (IMFINZI®)), and/or a CTLA-4 inhibitor (e.g., Ipilimumab (YERVOY®), and Tremelimumab) may be administered to the patient prior to, concurrently with, or after administration of dovitinib or a pharmaceutically acceptable salt thereof. In some embodiments, a method of administering an immune checkpoint inhibitor (e.g., a PD1 inhibitor, a PD-L1 inhibitor, or a CTLA-4 inhibitor) in combination with (e.g., prior to, concurrently with, or after administration of) dovitinib or a pharmaceutically acceptable salt thereof, the dovitinib DRP described hereinabove can be combined with an expression level of a biomarker of checkpoint inhibition (or a panel of biomarkers of checkpoint inhibitor, such as a panel of 2, 3, or more biomarkers of checkpoint inhibition (e.g., PD-1, PD-L1, CTLA-4, and FAS receptor). In particular embodiments, expression level of a three-gene biomarker of checkpoint inhibition can include an average of expression level of genes listed in Table 4 (e.g., PD-1 (e.g., SEQ ID NO: 59), PD-L1 (e.g., SEQ ID NO: 60), and FAS (e.g., SEQ ID NO: 61)). The dovitinib DRP and the three-gene biomarker of checkpoint inhibition can be given equal weight, for example by taking their average after normalization to a scale from zero to 100.

Additionally or alternatively, an aromatase inhibitor (e.g., a non-selective aromatase inhibitor, such as Aminoglutethimide and Testolactone (TESLAC®), a selective aromatase inhibitor, such as anastrozole (ARIMIDEX®), letrozole (FEMARA®), exemestane (AROMASIN®), vorozole (RIVIZOR®), formestane (LENTARON®), and fadrozole (AFEMA®), and other aromatase inhibitors, such as 1,4,6-Androstatrien-3,17-dione (ATD) and 4-Androstene-3,6,17-trione (6-OXO)) may be administered to the patient prior to, concurrently with, or after administration of dovitinib or a pharmaceutically acceptable salt thereof.

Additionally, or alternatively, an antiestrogen (e.g., a selective estrogen receptor modulator (SERM) (e.g., tamoxifen, clomifene, and raloxifene), an estrogen receptor silent antagonist, and selective estrogen receptor degrader (SERD) (e.g., fulvestrant (FASLODEX®))) may be administered to the patient prior to, concurrently with, or after administration of dovitinib or a pharmaceutically acceptable salt thereof.

Additionally, or alternatively, an antigonadotropin (e.g., gonadotropin-releasing hormone (GnRH) analogue, compounds acting on sex steroid hormone receptors (e.g., progestogens, androgens, and estrogens), and steroid synthesis inhibitors (e.g., danazol (DANOCRINE®) and gestrinone (DIMETROSE®))) may be administered to the patient prior to, concurrently with, or after administration of dovitinib or a pharmaceutically acceptable salt thereof.

The therapeutic agent (e.g., immune checkpoint inhibitor (e.g., a PD1 inhibitor, a PD-L1 inhibitor, or a CTLA-4 inhibitor), aromatase inhibitor, and/or antiestrogen (e.g., fulvestrant)) can be administered parenterally (e.g. intravenously, intramuscularly, transdermally, intradermally, intraarterially, intracranially, subcutaneously, intraorbitally, intraventricularly, intraspinally, intraperitoneally, or intranasally), enterally, or topically.

Alternatively, a patient can be, e.g., identified as less likely to be responsive to dovitinib or a pharmaceutically acceptable salt thereof by determining the expression level of one or more biomarkers (e.g., one or more of the biomarkers shown in Table(s) 2 and/or 3, such as DDIT4 (SEQ ID NO: 1) and/or SCAMPS (SEQ ID NO: 31)) in a biological sample obtained from the patient. If the patient exhibits expression levels of one or more biomarkers indicative of non-responsiveness to dovitinib, the patient can be administered a treatment other than dovitinib or a pharmaceutically acceptable salt thereof (e.g., surgery, radiation, or a therapeutic agent). In particular, the therapeutic agent may be one or more of a histone deacetylase (HDAC) inhibitor, a PD1 or PD-L1 inhibitor, ipilimumab, a cyclin-dependent kinase inhibitor (e.g., a CDK inhibitor selective for CDK4 and CDK6, such as palbociclib (IBRANCE®) and abemaciclib (VERZENIO®, VERZENIOS®)), venetoclax (VENCLEXTA®, VENCLYXTO®), ibrutinib (IMBRUVICA®), bortezomib, carfilzomib, thalidomide, lenalidomide, pomalidomide, prednisone, dexamethasone, cyclophosphamide, vincristine, doxorubicin, melphalan, capecitabine, tegafur, irinotecan, oxaliplatin, cetuximab, leucovorin, SN-38, everolimus, temsirolimus, bleomycin, lomustine, depsipeptide, carboplatin, erlotinib, gemcitabine, mitoxantrone, cisplatin, busulfan, epirubicin, arsenic trioxide, bendamustine, fulvestrant, teniposide, adriamycin, decitabine, estramustine, etoposide, azaguanine, aclarubicin, mitoxantrone, mitomycin, paclitaxel, taxotere, Irofulven, 5-FU, ara-c, methylprednisolone, methotrexate, methyl-gag, belinostat, carboplatin, idarubicin, IL4-PR38, valproic acid, all-trans retinoic acid (ATRA), cytoxan, topotecan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, tamoxifen, floxuridine, thioguanine, PSC 833, herceptin, bevacizumab, celecoxib, iressa, anastrozole, letrozole, and rituximab. The therapeutic agent can be administered parenterally (e.g. intravenously, intramuscularly, transdermally, intradermally, intra-arterially, intracranially, subcutaneously, intraorbitally, intraventricularly, intraspinally, intraperitoneally, or intranasally), enterally, or topically. In particular, the patient may be treated with, e.g., surgery, radiation, and/or administration of a therapeutic agent, such as a histone deacetylase (HDAC) inhibitor and/or docetaxel.

Administration of Dovitinib

Once a patient has been determined to be responsive to dovitinib or a pharmaceutically acceptable salt thereof, according to the methods described herein, dovitinib or a pharmaceutically acceptable salt thereof may be administered to the patient, for example, parenterally, enterally, or topically. Enteral routes of dovitinib (e.g., dovitinib or a pharmaceutically acceptable salt thereof) administration may include oral, buccal, sublabial, sublingual, or by inhalation. Parenteral routes of dovitinib (e.g., dovitinib or a pharmaceutically acceptable salt thereof) administration include intravenous, transdermal, intradermal, intramuscular, intra-arterial, intracranial, subcutaneous, intraorbital, intraventricular, intraspinal, intraperitoneal, or intranasal. The preferred route for administration of dovitinib may be oral.

Dovitinib or a pharmaceutically acceptable salt thereof can be administered at, e.g., a dose of about 5-5000 mg, 10-4500 mg, 15-4000 mg, 20-3500 mg, 25-3000 mg, 30-2500 mg, 35-2000 mg, 40-1500 mg, 45-1000 mg, 50-1000 mg, 50-950 mg, 50-900 mg, 50-850 mg, 50-800 mg, 55-800 mg, 60-800 mg, 65-800 mg, 70-800 mg, 75-800 mg, 80-800 mg, 85-800 mg, 90-800 mg, 90-500 mg, 90-300 mg, 95-800 mg, 100-800 mg, 100-500 mg, 100-250 mg, 125-800 mg, 150-800 mg, 175-800 mg, 200-800 mg, 225-800 mg, 250-800 mg, 250-500 mg, 275-800 mg, 300-800 mg, 325-800 mg, 350-800 g, 375-800 mg, 400-800 mg, 425-800 mg, 450-800 mg, 475-800 mg, 500-800 mg, 525-800 mg, 550-800 mg, 575-800 mg, 600-800 mg, 625-800 mg, 650-800 mg, 675-800 mg, 700-800 mg, 725-800 mg, 750-800 mg, or 775-800 mg. In particular, dovitinib or a pharmaceutically acceptable salt thereof may be administered at doses of about 10 mg, 50 mg, 100 mg, 200 mg, 250 mg, 500 mg, 600 mg, or 750 mg. In particular, dovitinib or a pharmaceutically acceptable salt thereof may be administered at doses of about 10 mg, 50 mg, 200 mg, or 500 mg. Preferably, dovitinib or a pharmaceutically acceptable salt thereof can be administered at a dose of about 500 mg. For example, about 500 mg of dovitinib or a pharmaceutically acceptable salt thereof can be administered orally (e.g., 5×100 mg hard gelatin capsules of dovitinib or a pharmaceutically acceptable salt thereof, or 2×250 mg film coated tablets of dovitinib or a pharmaceutically acceptable salt thereof can be administered orally), as described by Sarantopoulos et al. (*Cancer Chemother Pharmacol* 5:621-628, 2008; hereby incorporated by reference). Dovitinib or a pharmaceutically acceptable salt thereof may be administered to the patient two or more times, such as one or more times hourly, daily (e.g., once daily for up to six days (e.g., once daily for one day, once daily for two days, once daily for three days, once daily for four days, once daily for five days, or once daily for six days)), weekly, every two weeks, every three weeks, every four weeks, monthly, every two months, every three months, every six months, or every year. Preferably, dovitinib may be administered once daily. For example, dovitinib or a pharmaceutically acceptable salt thereof can be administered orally at a dose of about 500 mg once daily (e.g., dovitinib or a pharmaceutically acceptable salt thereof can be administered orally as 5×100 mg hard gelatin capsules or 2×250 mg film coated tablets once daily). Preferably, dovitinib or a pharmaceutically acceptable salt thereof can be administered orally at a dose of about 500 mg once daily for five days (e.g., dovitinib or a pharmaceutically acceptable salt thereof can be administered orally as 5×100 mg hard gelatin capsules or 2×250 mg film coated tablets once daily for five days).

Dovitinib or a pharmaceutically acceptable salt thereof (e.g., at a dose of about 500 mg once daily (e.g., as 5×100 mg hard gelatin capsules or 2×250 mg film coated tablets once daily)) can be administered in an ON: OFF schedule, such as a schedule that includes an ON schedule and an OFF schedule, wherein dovitinib or a pharmaceutically acceptable salt thereof is administered to a subject (e.g., a patient, such as a patient determined to be responsive to dovitinib or a pharmaceutically acceptable salt thereof by one or more methods described herein) during the ON schedule, and dovitinib or a pharmaceutically acceptable salt thereof is not administered to a subject (e.g., a patient, such as a patient determined to be non-responsive to dovitinib or a pharmaceutically acceptable salt thereof by one or more methods described herein) during the OFF schedule. In some embodiments, the ON schedule may be for one-ten days, such as one day, two days, three days, four days, five days, six days, seven days, eight days, nine days, or ten days. In some embodiments, the OFF schedule may be for one-ten days, such as one day, two days, three days, four days, five days, six days, seven days, eight days, nine days, or ten days. For example, dovitinib or a pharmaceutically acceptable salt thereof may be administered to a subject (e.g., a patient, such as a patient determined to be responsive to dovitinib or a pharmaceutically acceptable salt thereof by one or more methods described herein) in a one-ten days ON: one-ten days OFF schedule, wherein dovitinib or the pharmaceutically acceptable salt thereof is administered to the subject (e.g., patient) for one-ten days (e.g., for one day, two days, three days, four days, five days, six days, seven days, eight days, nine days, or ten days during the ON schedule), and dovitinib or the pharmaceutically acceptable salt thereof is not administered to the subject (e.g., patient) for one-ten days (e.g., for one day, two days, three days, four days, five days, six days, seven days, eight days, nine days, or ten days during the OFF schedule). In some embodiments, the OFF schedule may follow the ON schedule. For example, a subject (e.g., a patient) is not administered dovitinib or a pharmaceutically acceptable salt thereof for one-ten days (e.g., for one-ten days during the OFF schedule) after administration of dovitinib or the pharmaceutically acceptable salt thereof for one-ten days (e.g., for one-ten days during the ON schedule).

In particular, dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a one day ON: one day OFF schedule, wherein dovitinib or the pharmaceutically acceptable salt thereof is administered to the subject for one day (e.g., for one day during the ON schedule) and not administered to the subject for the following one day (e.g., for one day during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a two days ON: one day OFF schedule, wherein dovitinib or the pharmaceutically acceptable salt thereof is administered to the subject for two days (e.g., for two days during the ON schedule) and not administered to the subject for the following one day (e.g., for one day during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a three days ON: one day OFF schedule, wherein dovitinib or the pharmaceutically acceptable salt thereof is administered to the subject for three days (e.g., for three days during the ON schedule) and not administered to the subject for the following one day (e.g., for one day during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a four days ON: one day OFF schedule, wherein dovitinib or the pharmaceutically acceptable salt thereof is administered to the subject for four days (e.g., for four days during the ON schedule) and not administered to the subject for the following one day (e.g., for one day during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a five days ON: one day OFF schedule, wherein dovitinib or the pharmaceutically acceptable salt thereof is administered to the subject for five days (e.g., for five days during the ON schedule) and not administered to the subject for the following one day (e.g., for one day during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a six days ON: one day OFF schedule, wherein dovitinib or the pharmaceutically acceptable salt thereof is administered to the subject for six days (e.g., for six days during the ON schedule) and not administered to the subject for the following one day (e.g., for one day during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a seven days ON: one day OFF schedule, wherein dovitinib or the pharmaceutically acceptable salt thereof is administered to the subject for seven days (e.g., for seven days during the ON schedule) and not administered to the subject for the following one day (e.g., for one day during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a eight days ON: one day OFF schedule, wherein dovitinib or the pharmaceutically acceptable salt thereof is administered to the subject for eight days (e.g., for eight days during the ON schedule) and not administered to the subject for the following one day (e.g., for one day during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a nine days ON: one day OFF schedule, wherein dovitinib or the pharmaceutically acceptable salt thereof is administered to the subject for nine days (e.g., for nine days during the ON schedule) and not administered to the subject for the following one day (e.g., for one day during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a ten days ON: one day OFF schedule, wherein dovitinib or the pharmaceutically acceptable salt thereof is administered to the subject for ten days (e.g., for ten days during the ON schedule) and not administered to the subject for the following one day (e.g., for one day during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a one day ON: two days OFF schedule, wherein dovitinib or the pharmaceutically acceptable salt thereof is administered to the subject for one day (e.g., for one day during the ON schedule) and not administered to the subject for the following two days (e.g., for two days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a two days ON: two days OFF schedule, wherein dovitinib or the pharmaceutically acceptable salt thereof is administered to the subject for two days (e.g., for two days during the ON schedule) and not administered to the subject for the following two days (e.g., for two days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a three days ON: two days OFF schedule, wherein dovitinib or the pharmaceutically acceptable salt thereof is administered to the subject for three days (e.g., for three days during the ON schedule) and not administered to the subject for the following two days (e.g., for two days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a four days ON: two days OFF schedule, wherein dovitinib or the pharmaceutically acceptable salt thereof is administered to the subject for four days (e.g., for four days during the ON schedule) and not administered to the subject for the following two days (e.g., for two days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a five days ON: two days OFF schedule, wherein dovitinib or the pharmaceutically acceptable salt thereof is administered to the subject for five days (e.g., for five days during the ON schedule) and not administered to the subject for the following two days (e.g., for two days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a six days ON: two days OFF schedule, wherein dovitinib or the pharmaceutically acceptable salt thereof is administered to the subject for six days (e.g., for six days during the ON schedule) and not administered to the subject for the following two days (e.g., for two days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a seven days ON: two days OFF schedule, wherein dovitinib or the pharmaceutically acceptable salt thereof is administered to the subject for seven days (e.g., for seven days during the ON schedule) and not administered to the subject for the following two days (e.g., for two days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a eight days ON: two days OFF schedule, wherein dovitinib or the pharmaceutically acceptable salt thereof is administered to the subject for eight days (e.g., for eight days during the ON schedule) and not administered to the subject for the following two days (e.g., for two days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a nine days ON: two days OFF schedule, wherein dovitinib or the pharmaceutically acceptable salt thereof is administered to the subject for nine days (e.g., for nine days during the ON schedule) and not administered to the subject for the following two days (e.g., for two days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a ten days ON: two days OFF schedule, wherein dovitinib or the pharmaceutically acceptable salt thereof is administered to the subject for ten days (e.g., for ten days during the ON schedule) and not administered to the subject for the following two days (e.g., for two days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a one day ON: three days OFF schedule, wherein dovitinib or the pharmaceutically acceptable salt thereof is administered to the subject for one day (e.g., for one day during the ON schedule) and not administered to the subject for the following three days (e.g., for three days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a two days ON: three days OFF schedule, wherein dovitinib or the pharmaceutically acceptable salt thereof is administered to the subject for two days (e.g., for two days during the ON schedule) and not administered to the subject for the following three days (e.g., for three days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a three days ON: three days OFF schedule, wherein dovitinib or the pharmaceutically acceptable salt thereof is administered to the subject for three days (e.g., for three days during the ON schedule) and not administered to the subject for the following three days (e.g., for three days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a four days ON: three days OFF schedule, wherein dovitinib or the pharmaceutically acceptable salt thereof is administered to the subject for four days (e.g., for four days during the ON schedule) and not administered to the subject for the following three days (e.g., for three days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a five days ON: three days OFF schedule, wherein dovitinib or the pharmaceutically acceptable salt thereof is administered to the subject for five days (e.g., for five days during the ON schedule) and not administered to the subject for the following three days (e.g., for three days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a six days ON: three days OFF schedule, wherein dovitinib or the pharmaceutically acceptable salt thereof is administered to the subject for six days (e.g., for six days during the ON schedule) and not administered to the subject for the following three days (e.g., for three days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a seven days ON: three days OFF schedule, wherein dovitinib or the pharmaceutically acceptable salt thereof is administered to the subject for seven days (e.g., for seven days during the ON schedule) and not administered to the subject for the following three days (e.g., for three days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a eight days ON: three days OFF schedule, wherein dovitinib or the pharmaceutically acceptable salt thereof is administered to the subject for eight days (e.g., for eight days during the ON schedule) and not administered to the subject for the following three days (e.g., for three days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a nine days ON: three days OFF schedule, wherein dovitinib or the pharmaceutically acceptable salt thereof is administered to the subject for nine days (e.g., for nine days during the ON schedule) and not administered to the subject for the following three days (e.g., for three days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a ten days ON: three days OFF schedule, wherein dovitinib or the pharmaceutically acceptable salt thereof is administered to the subject for ten days (e.g., for ten days during the ON schedule) and not administered to the subject for the following three days (e.g., for three days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a one day ON: four days OFF schedule, wherein dovitinib or the pharmaceutically acceptable salt thereof is administered to the subject for one day (e.g., for one day during the ON schedule) and not administered to the subject for the following four days (e.g., for four days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a two days ON: four days OFF schedule, wherein dovitinib or the pharmaceutically acceptable salt thereof is administered to the subject for two days (e.g., for two days during the ON schedule) and not administered to the subject for the following four days (e.g., for four days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a three days ON: four days OFF schedule, wherein dovitinib or the pharmaceutically acceptable salt thereof is administered to the subject for three days (e.g., for three days during the ON schedule) and not administered to the subject for the following four days (e.g., for four days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a four days ON: four days OFF schedule, wherein dovitinib or the pharmaceutically acceptable salt thereof is administered to the subject for four days (e.g., for four days during the ON schedule) and not administered to the subject for the following four days (e.g., for four days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a five days ON: four days OFF schedule, wherein dovitinib or the pharmaceutically acceptable salt thereof is administered to the subject for five days (e.g., for five days during the ON schedule) and not administered to the subject for the following four days (e.g., for four days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a six days ON: four days OFF schedule, wherein dovitinib or the pharmaceutically acceptable salt thereof is administered to the subject for six days (e.g., for six days during the ON schedule) and not administered to the subject for the following four days (e.g., for four days during the OFF schedule).

Dovitinib or a pharmaceutically acceptable salt thereof (e.g., at a dose of about 500 mg once daily) may be administered (e.g., orally) to a subject (e.g., a patient, such as a patient determined to be responsive to dovitinib or a pharmaceutically acceptable salt thereof by one or more methods described herein) in a seven days ON: four days OFF schedule, wherein dovitinib or the pharmaceutically acceptable salt thereof is administered to the subject for seven days (e.g., for seven days during the ON schedule) and not administered to the subject for the following four days (e.g., for four days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a eight days ON: four days OFF schedule, wherein dovitinib or the pharmaceutically acceptable salt thereof is administered to the subject for eight days (e.g., for eight days during the ON schedule) and not administered to the subject for the following four days (e.g., for four days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a nine days ON: four days OFF schedule, wherein dovitinib or the pharmaceutically acceptable salt thereof is administered to the subject for nine days (e.g., for nine days during the ON schedule) and not administered to the subject for the following four days (e.g., for four days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a ten days ON: four days OFF schedule, wherein dovitinib or the pharmaceutically acceptable salt thereof is administered to the subject for ten days (e.g., for ten days during the ON schedule) and not administered to the subject for the following four days (e.g., for four days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a one day ON: five days OFF schedule, wherein dovitinib or the pharmaceutically acceptable salt thereof is administered to the subject for one day (e.g., for one day during the ON schedule) and not administered to the subject for the following five days (e.g., for five days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a two days ON: five days OFF schedule, wherein dovitinib or the pharmaceutically acceptable salt thereof is administered to the subject for two days (e.g., for two days during the ON schedule) and not administered to the subject for the following five days (e.g., for five days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a three days ON: five days OFF schedule, wherein dovitinib or the pharmaceutically acceptable salt thereof is administered to the subject for three days (e.g., for three days during the ON schedule) and not administered to the subject for the following five days (e.g., for five days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a four days ON: five days OFF schedule, wherein dovitinib or the pharmaceutically acceptable salt thereof is administered to the subject for four days (e.g., for four days during the ON schedule) and not administered to the subject for the following five days (e.g., for five days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a five days ON: five days OFF schedule, wherein dovitinib or the pharmaceutically acceptable salt thereof is administered to the subject for five days (e.g., for five days during the ON schedule) and not administered to the subject for the following five days (e.g., for five days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a six days ON: five days OFF schedule, wherein dovitinib or the pharmaceutically acceptable salt thereof is administered to the subject for six days (e.g., for six days during the ON schedule) and not administered to the subject for the following five days (e.g., for five days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a seven days ON: five days OFF schedule, wherein dovitinib or the pharmaceutically acceptable salt thereof is administered to the subject for seven days (e.g., for seven days during the ON schedule) and not administered to the subject for the following five days (e.g., for five days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a eight days ON: five days OFF schedule, wherein dovitinib or the pharmaceutically acceptable salt thereof is administered to the subject for eight days (e.g., for eight days during the ON schedule) and not administered to the subject for the following five days (e.g., for five days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a nine days ON: five days OFF schedule, wherein dovitinib or the pharmaceutically acceptable salt thereof is administered to the subject for nine days (e.g., for nine days during the ON schedule) and not administered to the subject for the following five days (e.g., for five days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a ten days ON: five days OFF schedule, wherein dovitinib or the pharmaceutically acceptable salt thereof is administered to the subject for ten days (e.g., for ten days during the ON schedule) and not administered to the subject for the following five days (e.g., for five days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a one day ON: six days OFF schedule, wherein dovitinib or the pharmaceutically acceptable salt thereof is administered to the subject for one day (e.g., for one day during the ON schedule) and not administered to the subject for the following six days (e.g., for six days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a two days ON:

six days OFF schedule, wherein dovitinib or the pharmaceutically acceptable salt thereof is administered to the subject for two days (e.g., for two days during the ON schedule) and not administered to the subject for the following six days (e.g., for six days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a three days ON: six days OFF schedule, wherein dovitinib or the pharmaceutically acceptable salt thereof is administered to the subject for three days (e.g., for three days during the ON schedule) and not administered to the subject for the following six days (e.g., for six days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a four days ON: six days OFF schedule, wherein dovitinib or the pharmaceutically acceptable salt thereof is administered to the subject for four days (e.g., for four days during the ON schedule) and not administered to the subject for the following six days (e.g., for six days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a five days ON: six days OFF schedule, wherein dovitinib or the pharmaceutically acceptable salt thereof is administered to the subject for five days (e.g., for five days during the ON schedule) and not administered to the subject for the following six days (e.g., for six days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a six days ON: six days OFF schedule, wherein dovitinib or the pharmaceutically acceptable salt thereof is administered to the subject for six days (e.g., for six days during the ON schedule) and not administered to the subject for the following six days (e.g., for six days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a seven days ON: six days OFF schedule, wherein dovitinib or the pharmaceutically acceptable salt thereof is administered to the subject for seven days (e.g., for seven days during the ON schedule) and not administered to the subject for the following six days (e.g., for six days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a eight days ON: six days OFF schedule, wherein dovitinib or the pharmaceutically acceptable salt thereof is administered to the subject for eight days (e.g., for eight days during the ON schedule) and not administered to the subject for the following six days (e.g., for six days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a nine days ON: six days OFF schedule, wherein dovitinib or the pharmaceutically acceptable salt thereof is administered to the subject for nine days (e.g., for nine days during the ON schedule) and not administered to the subject for the following six days (e.g., for six days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a ten days ON: six days OFF schedule, wherein dovitinib or the pharmaceutically acceptable salt thereof is administered to the subject for ten days (e.g., for ten days during the ON schedule) and not administered to the subject for the following six days (e.g., for six days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a one day ON: seven days OFF schedule, wherein dovitinib or the pharmaceutically acceptable salt thereof is administered to the subject for one day (e.g., for one day during the ON schedule) and not administered to the subject for the following seven days (e.g., for seven days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a two days ON: seven days OFF schedule, wherein dovitinib or the pharmaceutically acceptable salt thereof is administered to the subject for two days (e.g., for two days during the ON schedule) and not administered to the subject for the following seven days (e.g., for seven days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a three days ON:

seven days OFF schedule, wherein dovitinib or the pharmaceutically acceptable salt thereof is administered to the subject for three days (e.g., for three days during the ON schedule) and not administered to the subject for the following seven days (e.g., for seven days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a four days ON: seven days OFF schedule, wherein dovitinib or the pharmaceutically acceptable salt thereof is administered to the subject for four days (e.g., for four days during the ON schedule) and not administered to the subject for the following seven days (e.g., for seven days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a five days ON: seven days OFF schedule, wherein dovitinib or the pharmaceutically acceptable salt thereof is administered to the subject for five days (e.g., for five days during the ON schedule) and not administered to the subject for the following seven days (e.g., for seven days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a six days ON: seven days OFF schedule, wherein dovitinib or the pharmaceutically acceptable salt thereof is administered to the subject for six days (e.g., for six days during the ON schedule) and not administered to the subject for the following seven days (e.g., for seven days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a seven days ON: seven days OFF schedule, wherein dovitinib or the pharmaceutically acceptable salt thereof is administered to the subject for seven days (e.g., for seven days during the ON schedule) and not administered to the subject for the following seven days (e.g., for seven days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a eight days ON: seven days OFF schedule, wherein dovitinib or the pharmaceutically acceptable salt thereof is administered to the subject for eight days (e.g., for eight days during the ON schedule) and not administered to the subject for the following seven days (e.g., for seven days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a nine days ON: seven days OFF schedule, wherein dovitinib or the pharmaceutically acceptable salt thereof is administered to the subject for nine days (e.g., for nine days during the ON schedule) and not administered to the subject for the following seven days (e.g., for seven days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a ten days ON: seven days OFF schedule, wherein dovitinib or the pharmaceutically acceptable salt thereof is administered to the subject for ten days (e.g., for ten days during the ON schedule) and not administered to the subject for the following seven days (e.g., for seven days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a one day ON: eight days OFF schedule, wherein dovitinib or the pharmaceutically acceptable salt thereof is administered to the subject for one day (e.g., for one day during the ON schedule) and not administered to the subject for the following eight days (e.g., for eight days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a two days ON: eight days OFF schedule, wherein dovitinib or the pharmaceutically acceptable salt thereof is administered to the subject for two days (e.g., for two days during the ON schedule) and not administered to the subject for the following eight days (e.g., for eight days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a three days ON: eight days OFF schedule, wherein dovitinib or the pharmaceutically acceptable salt thereof is administered to the subject for three days (e.g., for three days during the ON schedule) and not administered to the subject for the following eight days (e.g., for eight days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a four days ON: eight days OFF schedule, wherein dovitinib or the pharmaceutically acceptable salt thereof is administered to the subject for four days (e.g., for four days during the ON schedule) and not administered to the subject for the following eight days (e.g., for eight days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a five days ON: eight days OFF schedule, wherein dovitinib or the pharmaceutically acceptable salt thereof is administered to the subject for five days (e.g., for five days during the ON schedule) and not administered to the subject for the following eight days (e.g., for eight days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a six days ON: eight days OFF schedule, wherein dovitinib or the pharmaceutically acceptable salt thereof is administered to the subject for six days (e.g., for six days during the ON schedule) and not administered to the subject for the following eight days (e.g., for eight days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a seven days ON: eight days OFF schedule, wherein dovitinib or the pharmaceutically acceptable salt thereof is administered to the subject for seven days (e.g., for seven days during the ON schedule) and not administered to the subject for the following eight days (e.g., for eight days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a eight days ON: eight days OFF schedule, wherein dovitinib or the pharmaceutically acceptable salt thereof is administered to the subject for eight days (e.g., for eight days during the ON schedule) and not administered to the subject for the following eight days (e.g., for eight days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a nine days ON: eight days OFF schedule, wherein dovitinib or the pharmaceutically acceptable salt thereof is administered to the subject for nine days (e.g., for nine days during the ON schedule) and not administered to the subject for the following eight days (e.g., for eight days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a ten days ON: eight days OFF schedule, wherein dovitinib or the pharmaceutically acceptable salt thereof is administered to the subject for ten days (e.g., for ten days during the ON schedule) and not administered to the subject for the following eight days (e.g., for eight days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a one day ON: nine days OFF schedule, wherein dovitinib or the pharmaceutically acceptable salt thereof is administered to the subject for one day (e.g., for one day during the ON schedule) and not administered to the subject for the following nine days (e.g., for nine days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a two days ON: nine days OFF schedule, wherein dovitinib or the pharmaceutically acceptable salt thereof is administered to the subject for two days (e.g., for two days during the ON schedule) and not administered to the subject for the following nine days (e.g., for nine days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a three days ON: nine days OFF schedule, wherein dovitinib or the pharmaceutically acceptable salt thereof is administered to the subject for three days (e.g., for three days during the ON schedule) and not administered to the subject for the following nine days (e.g., for nine days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a four days ON: nine days OFF schedule, wherein dovitinib or the pharmaceutically acceptable salt thereof is administered to the subject for four days (e.g., for four days during the ON schedule) and not administered to the subject for the following nine days (e.g., for nine days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a five days ON: nine days OFF schedule, wherein dovitinib or the pharmaceutically acceptable salt thereof is administered to the subject for five days (e.g., for five days during the ON schedule) and not administered to the subject for the following nine days (e.g., for nine days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a six days ON: nine days OFF schedule, wherein dovitinib or the pharmaceutically acceptable salt thereof is administered to the subject for six days (e.g., for six days during the ON schedule) and not administered to the subject for the following nine days (e.g., for nine days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a seven days ON: nine days OFF schedule, wherein dovitinib or the pharmaceutically acceptable salt thereof is administered to the subject for seven days (e.g., for seven days during the ON schedule) and not administered to the subject for the following nine days (e.g., for nine days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a eight days ON: nine days OFF schedule, wherein dovitinib or the pharmaceutically acceptable salt thereof is administered to the subject for eight days (e.g., for eight days during the ON schedule) and not administered to the subject for the following nine days (e.g., for nine days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a nine days ON: nine days OFF schedule, wherein dovitinib or the pharmaceutically acceptable salt thereof is administered to the subject for nine days (e.g., for nine days during the ON schedule) and not administered to the subject for the following nine days (e.g., for nine days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a ten days ON: nine days OFF schedule, wherein dovitinib or the pharmaceutically acceptable salt thereof is administered to the subject for ten days (e.g., for ten days during the ON schedule) and not administered to the subject for the following nine days (e.g., for nine days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a one day ON: ten days OFF schedule, wherein dovitinib or the pharmaceutically acceptable salt thereof is administered to the subject for one day (e.g., for one day during the ON schedule) and not administered to the subject for the following ten days (e.g., for ten days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a two days ON: ten days OFF schedule, wherein dovitinib or the pharmaceutically acceptable salt thereof is administered to the subject for two days (e.g., for two days during the ON schedule) and not administered to the subject for the following ten days (e.g., for ten days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a three days ON: ten days OFF schedule, wherein dovitinib or the pharmaceutically acceptable salt thereof is administered to the subject for three days (e.g., for three days during the ON schedule) and not administered to the subject for the following ten days (e.g., for ten days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a four days ON: ten days OFF schedule, wherein dovitinib or the pharmaceutically acceptable salt thereof is administered to the subject for four days (e.g., for four days during the ON schedule) and not administered to the subject for the following ten days (e.g., for ten days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a five days ON: ten days OFF schedule, wherein dovitinib or the pharmaceutically acceptable salt thereof is administered to the subject for five days (e.g., for five days during the ON schedule) and not administered to the subject for the following ten days (e.g., for ten days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a six days ON: ten days OFF schedule, wherein dovitinib or the pharmaceutically acceptable salt thereof is administered to the subject for six days (e.g., for six days during the ON schedule) and not administered to the subject for the following ten days (e.g., for ten days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a seven days ON: ten days OFF schedule, wherein dovitinib or the pharmaceutically acceptable salt thereof is administered to the subject for seven days (e.g., for seven days during the ON schedule) and not administered to the subject for the following ten days (e.g., for ten days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a eight days ON: ten days OFF schedule, wherein dovitinib or the pharmaceutically acceptable salt thereof is administered to the subject for eight days (e.g., for eight days during the ON schedule) and not administered to the subject for the following ten days (e.g., for ten days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a nine days ON: ten days OFF schedule, wherein dovitinib or the pharmaceutically acceptable salt thereof is administered to the subject for nine days (e.g., for nine days during the ON schedule) and not administered to the subject for the following ten days (e.g., for ten days during the OFF schedule).

Dovitinib or a pharmaceutically acceptable salt thereof (e.g., at a dose of about 500 mg once daily (e.g., as 5×100 mg hard gelatin capsules or 2×250 mg film coated tablets once daily)) may be administered (e.g., orally) to a subject (e.g., a patient, such as a patient determined to be responsive to dovitinib or a pharmaceutically acceptable salt thereof by one or more methods described herein) in a ten days ON: ten days OFF schedule, wherein dovitinib or the pharmaceutically acceptable salt thereof is administered to the subject for ten days (e.g., for ten days during the ON schedule) and not administered to the subject for the following ten days (e.g., for ten days during the OFF schedule).

The method may further include administering a second dose of dovitinib or a pharmaceutically acceptable salt thereof to the patient two days, four days, six days, one week, two weeks, three weeks, four weeks, or five weeks after administration of a first dose of dovitinib or a pharmaceutically acceptable salt thereof. The administration of dovitinib or a pharmaceutically acceptable salt thereof can be repeated at such a frequency for a certain period of time, followed by a period without treatment. Such repeated administrations can occur over a course of therapy lasting a specified length of time (e.g., at least 1 week, 2 weeks, 3 weeks, 1 month, 2 months, 3 months, 6 months, 8 months, 10 months, 12 months, 18 months, 24 months, 36 months, 48 months, or 60 months).

The patient may be administered a pharmaceutically acceptable salt of dovitinib. Pharmaceutically acceptable salts of dovitinib described herein may include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of dovitinib described herein or separately by reacting a free base group with a suitable organic acid.

Dovitinib may have ionizable groups so as to be capable of preparation as pharmaceutically acceptable salts. These salts may be acid addition salts involving inorganic or organic acids or the salts may, in the case of acidic forms of dovitinib be prepared from inorganic or organic bases. Frequently, dovitinib may be prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-optionally substituted hydroxyl-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

Dovitinib or a pharmaceutically acceptable salt thereof can be administered in a pharmaceutical composition that includes one or more pharmaceutically acceptable carriers, excipients, or diluents. Examples of suitable carriers, excipients, or diluents of dovitinib or a pharmaceutically acceptable salt thereof include, e.g., saline, sterile water, polyalkylene glycols, oils of vegetable origin, hydrogenated napthalenes, suitable buffer, 1,3-butanediol, Ringer's solution and/or sodium chloride solution. Exemplary formulations for parenteral administration can include solutions prepared in water suitably mixed with a surfactant, e.g., hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Other exemplary carriers, excipients, or diluents are described in the *Handbook of Pharmaceutical Excipients*, 6th Edition, Rowe et al., Eds., *Pharmaceutical Press* (2009), hereby incorporated by reference in its entirety.

A pharmaceutical composition can be formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating dovitinib or a pharmaceutically acceptable salt thereof in the required amount in an appropriate solvent with one or a combination of ingredients enumerated above, as required, followed by filtered sterilization. Dispersions can be prepared by incorporating dovitinib or a pharmaceutically acceptable salt thereof into a sterile vehicle which contains a basic dispersion medium and the required other ingredients from those enumerated above. In the case of sterile powders for the preparation of sterile injectable solutions, the preferred methods of preparation can be vacuum drying and freeze-drying which yields a powder of dovitinib or a pharmaceutically acceptable salt thereof plus any additional desired ingredient from a previously sterile-filtered solution thereof.

Oral compositions can include an inert diluent or an edible carrier. The composition can be enclosed in a gelatin capsule or compressed into a tablet. For the purpose of oral therapeutic administration, dovitinib or a pharmaceutically acceptable salt thereof can be incorporated with excipients and used in the form of tablets, troches, or gelatin capsules. In particular, dovitinib or a pharmaceutically acceptable salt thereof can be formulated as hard gelatin capsules (e.g., hard gelatin capsules of 10 mg, 50 mg, 100 mg, 200 mg, or 250 mg) or film coated tablets (e.g., film coated tablets of 10 mg, 50 mg, 100 mg, 200 mg, or 250 mg). Preferably, dovitinib or a pharmaceutically acceptable salt thereof can be formulated as hard gelatin capsules (e.g., hard gelatin capsules of 100 mg) or film coated tablets (e.g., film coated tablets of 250 mg), as described by Sarantopoulos et al. (*Cancer Chemother Pharmacol* 5:621-628, 2008; hereby incorporated by reference). Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated can be used in the formulation. Such penetrants are generally known, and include, for example, for transmucosal administration, detergents, bile salts, and fusidic acid derivatives. Transmucosal administration can be accomplished through the use of nasal sprays or suppositories. For transdermal administration, dovitinib or a pharmaceutically acceptable salt thereof may be formulated into ointments, salves, gels, or creams as generally known in the art.

Dovitinib or a pharmaceutically acceptable salt thereof can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions can also be used as pharmaceutically acceptable carriers. These can be prepared according to methods known to those skilled in the art.

The pharmaceutical compositions can be included in a container, pack, or dispenser together with instructions for administration.

Methods of formulating pharmaceutical agents are known in the art, e.g., Niazi, Handbook of Pharmaceutical Manufacturing Formulations (Second Edition), CRC Press 2009, describes formulation development for liquid, sterile, compressed, semi-compressed and OTC forms. Transdermal and mucosal delivery, lymphatic system delivery, nanoparticles, controlled drug release systems, theranostics, protein and peptide drugs, and biologics delivery are described in Wang et al., Drug Delivery: Principles and Applications (Second Edition), Wiley 2016; formulation and delivery of peptide and protein agent is described, e.g., in Banga, Therapeutic Peptides and Proteins: Formulation, Processing, and Delivery Systems (Third Edition), CRC Press 2015.

Kits

Kits of the invention can be used for determining the responsiveness of a cancer patient (e.g., a hematological cancer, such as multiple myeloma, or a solid tumor, such as breast cancer or ovarian cancer) to dovitinib or a pharmaceutically acceptable salt thereof. Kits of the invention can include reagents and/or materials for, e.g., collecting and/or purifying nucleic acids from biological samples (such as those obtained from a patient to be treated with dovitinib or a pharmaceutically acceptable salt thereof), reagents for amplifying such nucleic acids to produce an amplified sample, and/or at least one device of the invention. Reagents for amplifying nucleic acids may include, e.g., PCR reagents, including but not limited to DNA polymerase, RNA polymerase, PCR buffer, magnesium chloride solutions, nucleic acid primers (e.g., primers designed to target particular biomarkers of responsiveness to dovitinib or a pharmaceutically acceptable salt thereof), and/or any other PCR reagents as are well known in the art. In particular, kits useful in the method may include includes one or more of the following: a kit for RNA extraction from tumors (e.g., Trizol for mRNA, mirVana miRNA isolation kit from Ambion Inc), a kit for RNA labeling (e.g., MessageAmp from Ambion Inc., FlashTag from Genisphere Inc), a microarray for measuring biomarker expression (e.g., HG-U133A, HG-U133_Plus2 or miRNA-1.0 from Affymetrix Inc), a microarray hybridization station and scanner (e.g., GeneChip System 3000Dx from Affymetrix Inc), and/or software for analyzing the expression of biomarker genes or RNAs (e.g., miRNAs) as described in herein (e.g., implemented in R from R-Project or S-Plus from Insightful Corp.).

For example, a kit of the invention can include one or more probes capable of detecting one or more biomarkers of Table(s) 2 and/or 3 (e.g., the kit may include probes for the biomarkers of Tables 2 and 3). Such probes can, for example, include nucleic acids capable of hybridizing to the biomarker based on nucleic acid sequence complementarity. In particular, a probe has at least 85% sequence identity (e.g., 85%, 90%, 95%, 97%, 98%, 99%, or 100% sequence identity) to a nucleic acid sequence that is complementary or identical to at least 5 (e.g., at least 15) consecutive nucleotides of one or more biomarkers. The probes can be attached a solid surface, such as a microarray. The kit may include NanoString capture probes, NanoString reporter probes, and/or one or more nCounter cartridges. The kit may include reagents for next generation sequencing, including but not limited to poly(T) oligonucleotides, dye terminators, sequencing adapters, adapter ligation reagents, reverse transcriptase, primers (e.g., random primers), DNA-cleaving enzymes, polymerases, and/or any combination thereof. The kit may also be one that includes a protein array and/or reagents for detection of the polypeptide product(s) of one or more biomarkers of Table(s) 2 and/or 3.

Further embodiments include the following:

1. A method of determining responsiveness of a subject with a cancer to dovitinib or a pharmaceutically acceptable salt thereof comprising:
   (a) contacting a sample from the subject comprising one or more nucleic acid molecules with a device comprising:
      (i) one or more single-stranded nucleic acid molecules capable of specifically hybridizing with the nucleotides of one or more biomarkers of sensitivity selected from the biomarkers of Table 2; and/or
      (ii) one or more single-stranded nucleic acid molecules capable of specifically hybridizing with the nucleotides of one or more biomarkers of resistance selected from the biomarkers of Table 3; and
   (b) measuring hybridization between the one or more nucleic acid molecules from the sample and the single-stranded nucleic acid molecules of the device to detect a level of expression of the one or more biomarkers of sensitivity and/or the one or more biomarkers of resistance.

2. The method of count 1, wherein the subject is determined to be responsive to dovitinib or a pharmaceutically acceptable salt thereof if:
   (i) the level of expression of the one or more biomarkers of sensitivity is substantially similar to the level of expression of the one or more biomarkers of sensitivity in a cell or tissue known to be sensitive to dovitinib or a pharmaceutically acceptable salt thereof;
   (ii) the level of expression of the one or more biomarkers of resistance is substantially similar to the level of expression of the one or more biomarkers of resistance in a cell or tissue known to be sensitive to dovitinib or a pharmaceutically acceptable salt thereof;
   (iii) the level of expression of the one or more biomarkers of sensitivity is substantially dissimilar to the level of expression of the one or more biomarkers of sensitivity in a cell or tissue known to be resistant to dovitinib or a pharmaceutically acceptable salt thereof; and/or
   (iv) the level of expression of the one or more biomarkers of resistance is substantially dissimilar to the level of expression of the one or more biomarkers of resistance in a cell or tissue known to be resistant to dovitinib or a pharmaceutically acceptable salt thereof.

3. The method of count 1 or 2, further comprising administering dovitinib or a pharmaceutically acceptable salt thereof to the subject.

4. The method of count 1, further comprising administering one or more cancer therapies other than dovitinib or a pharmaceutically acceptable salt thereof to the subject.

5. The method of count 4, wherein:
   (i) the level of expression of the one or more biomarkers of sensitivity is substantially dissimilar to the level of expression of the one or more biomarkers of sensitivity in a cell or tissue known to be sensitive to dovitinib or a pharmaceutically acceptable salt thereof;
(ii) the level of expression of the one or more biomarkers of resistance is substantially dissimilar to the level of expression of the one or more biomarkers of resistance in a cell or tissue known to be sensitive to dovitinib or a pharmaceutically acceptable salt thereof;
(iii) the level of expression of the one or more biomarkers of sensitivity is substantially similar to the level of expression of the one or more biomarkers of sensitivity in a cell or tissue known to be resistant to dovitinib or a pharmaceutically acceptable salt thereof; and/or
(iv) the level of expression of the one or more biomarkers of resistance is substantially similar to the level of expression of the one or more biomarkers of resistance in a cell or tissue known to be resistant to dovitinib or a pharmaceutically acceptable salt thereof.

6. The method of any one of counts 2-5, wherein:
(i) sensitivity of a cell or tissue known to be sensitive to dovitinib or a pharmaceutically acceptable salt thereof is based on GI50 data of NCI60 cell lines; and/or
(ii) resistance of a cell or tissue known to be resistant to dovitinib or a pharmaceutically acceptable salt thereof is based on GI50 data of NCI60 cell lines.

7. The method of count 4, wherein the one or more cancer therapies comprises surgery, radiation, or a therapeutic agent.

8. The method of count 7, wherein the therapeutic agent is selected from the group consisting of a histone deacetylase (HDAC) inhibitor, an immune checkpoint inhibitor, a cyclin-dependent kinase (CDK) inhibitor, bortezomib, carfilzomib, thalidomide, lenalidomide, pomalidomide, prednisone, dexamethasone, cyclophosphamide, vincristine, doxorubicin, melphalan, capecitabine, tegafur, irinotecan, oxaliplatin, cetuximab, leucovorin, SN-38, everolimus, temsirolimus, bleomycin, lomustine, depsipeptide, carboplatin, erlotinib, gemcitabine, mitoxantrone, cisplatin, busulfan, epirubicin, arsenic trioxide, bendamustine, fulvestrant, teniposide, adriamycin, decitabine, estramustine, etoposide, azaguanine, aclarubicin, mitoxantrone, mitomycin, paclitaxel, taxotere, Irofulven, 5-FU, ara-c, methylprednisolone, methotrexate, methyl-gag, belinostat, carboplatin, idarubicin, IL4-PR38, valproic acid, all-trans retinoic acid (ATRA), cytoxan, topotecan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, tamoxifen, floxuridine, thioguanine, PSC 833, herceptin, bevacizumab, celecoxib, iressa, anastrozole, letrozole, and rituximab.

9. The method of count 8, wherein the immune checkpoint inhibitor is a PD1 inhibitor, a PD-L1 inhibitor, or a CTLA-4 inhibitor.

10. A method of treating a cancer in a subject in need thereof comprising administering dovitinib or a pharmaceutically acceptable salt thereof to the subject, wherein the subject has been determined to be responsive to dovitinib or the pharmaceutically acceptable salt thereof according to the method of count 1.

11. A method of treating a subject with a cancer, the method comprising:
(a) contacting a sample from the subject comprising one or more nucleic acid molecules with a device comprising:
(i) one or more single-stranded nucleic acid molecules capable of specifically hybridizing with the nucleotides of one or more biomarkers of sensitivity selected from the biomarkers of Table 2; and/or
(ii) one or more single-stranded nucleic acid molecules capable of specifically hybridizing with the nucleotides of one or more biomarkers of resistance selected from the biomarkers of Table 3;
(b) measuring hybridization between the one or more nucleic acid molecules from the sample and the single-stranded nucleic acid molecules of the device to detect a level of expression of the one or more biomarkers of sensitivity and/or the one or more biomarkers of resistance; and
(c) administering dovitinib or a pharmaceutically acceptable salt thereof to the subject.

12. The method of count 11, wherein the subject is administered dovitinib or the pharmaceutically acceptable salt thereof if:
(i) the level of expression of the one or more biomarkers of sensitivity is substantially similar to the level of expression of the one or more biomarkers of sensitivity in a cell or tissue known to be sensitive to dovitinib or a pharmaceutically acceptable salt thereof;
(ii) the level of expression of the one or more biomarkers of resistance is substantially similar to the level of expression of the one or more biomarkers of resistance in a cell or tissue known to be sensitive to dovitinib or a pharmaceutically acceptable salt thereof;
(iii) the level of expression of the one or more biomarkers of sensitivity is substantially dissimilar to the level of expression of the one or more biomarkers of sensitivity in a cell or tissue known to be resistant to dovitinib or a pharmaceutically acceptable salt thereof; and/or
(iv) the level of expression of the one or more biomarkers of resistance is substantially dissimilar to the level of expression of the one or more biomarkers of resistance in a cell or tissue known to be resistant to dovitinib or a pharmaceutically acceptable salt thereof.

13. The method of count 12, wherein:
(i) sensitivity of a cell or tissue known to be sensitive to dovitinib or a pharmaceutically acceptable salt thereof is based on GI50 data of NCI60 cell lines; and/or
(ii) resistance of a cell or tissue known to be resistant to dovitinib or a pharmaceutically acceptable salt thereof is based on GI50 data of NCI60 cell lines.

14. The method of count 11, further comprising administering one or more additional therapies to the subject prior to, concurrently with, or after administration of dovitinib or the pharmaceutically acceptable salt thereof.

15. The method of count 14, wherein the one or more additional therapies comprises surgery, radiation, or a therapeutic agent.

16. The method of count 15, wherein the therapeutic agent is selected from the group consisting of a histone deacetylase (HDAC) inhibitor, an immune checkpoint inhibitor, an antiestrogen, an aromatase inhibitor, an antigonadotropin, a proteasome inhibitor, an immunomodulator, a glucocorticoid, a folic acid, a monoclonal antibody, and an antineoplastic agent, wherein optionally the therapeutic agent is fulvestrant, ipilimumab, a cyclin-dependent kinase (CDK) inhibitor, bortezomib, carfilzomib, thalidomide, lenalidomide, pomalidomide, prednisone, dexamethasone, cyclophosphamide, vincristine, doxorubicin, melphalan, capecitabine, tegafur, irinotecan, oxaliplatin, cetuximab, leucovorin, SN-38, everolimus, temsirolimus, bleomycin, lomustine, depsipeptide, carboplatin, erlotinib, gemcitabine, mitoxantrone, cisplatin, busulfan, epirubicin, arsenic trioxide, bendamustine, teniposide, adriamycin, decitabine, estramustine, etoposide, azaguanine, aclarubicin, mitoxantrone, mitomycin, paclitaxel, taxotere, Irofulven, 5-FU, ara-c, methylprednisolone, methotrexate, methyl-gag, belinostat, carboplatin, idarubicin, IL4-PR38, valproic acid, all-trans retinoic acid (ATRA), cytoxan, topotecan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, tamoxifen, clomifene, raloxifene, floxuridine, thioguanine, PSC 833, herceptin, bevacizumab, celecoxib, iressa, anastrozole, letrozole, or rituximab.

17. The method of count 16, wherein the therapeutic agent is an immune checkpoint inhibitor, wherein optionally the immune checkpoint inhibitor is a PD1 inhibitor, a PD-L1 inhibitor, or a CTLA-4 inhibitor.

18. The method of any one of counts 1-17, further comprising determining an expression level of one or more biomarkers of responsiveness to an immune checkpoint inhibitor,
   wherein preferentially the one or more biomarkers are selected from the group consisting of PD-1, PD-L1, CTLA-4, and FAS receptor, such as a three-gene biomarker of PD-1, PD-L1, and FAS receptor, wherein optionally the expression level of the three-gene biomarker of checkpoint inhibition comprises an average of expression level of genes listed in Table 4; and
   wherein preferentially the method further comprises administering the immune checkpoint inhibitor to the subject that has been determined to be responsive to the immune checkpoint inhibitor.

19. The method of count 16, wherein the therapeutic agent is an antiestrogen, wherein optionally the antiestrogen is a selective estrogen receptor modulator, an estrogen receptor silent antagonist, or a selective estrogen receptor degrader.

20. The method of count 19, wherein the antiestrogen is fulvestrant.

21. The method of count 16, wherein the therapeutic agent is an aromatase inhibitor.

22. The method of count 16, wherein the therapeutic agent is an antigonadotropin, wherein optionally the antigonadotropin is gonadotropin-releasing hormone (GnRH) analogue, progestogen, or androgen.

23. The method of any one of counts 16-22, wherein the therapeutic agent is administered parenterally, enterally, or topically.

24. The method of count 23, wherein the therapeutic agent is administered intravenously, intramuscularly, transdermally, intradermally, intra-arterially, intracranially, subcutaneously, intraorbitally, intraventricularly, intraspinally, intraperitoneally, or intranasally.

25. The method of any one of counts 3 and 10-24, wherein dovitinib or the pharmaceutically acceptable salt thereof is administered parenterally, enterally, or topically.

26. The method of count 24, wherein dovitinib or the pharmaceutically acceptable salt thereof is administered intravenously, intramuscularly, transdermally, intradermally, intra-arterially, intracranially, subcutaneously, intraorbitally, intraventricularly, intraspinally, intraperitoneally, or intranasally.

27. The method of count 24, wherein dovitinib or the pharmaceutically acceptable salt thereof is administered orally.

28. The method of any one of counts 3 and 10-27, comprising administering dovitinib or the pharmaceutically acceptable salt thereof to the subject two or more times.

29. The method of count 28, comprising administering dovitinib or the pharmaceutically acceptable salt thereof to the subject one or more times daily, weekly, every two weeks, every three weeks, or monthly.

30. The method of count 29, comprising administering dovitinib or the pharmaceutically acceptable salt thereof to the subject once daily.

31. The method of count 30, comprising administering dovitinib or the pharmaceutically acceptable salt thereof to the subject once daily for five days.

32. The method of any one of counts 3 and 10-31, comprising administering dovitinib or the pharmaceutically acceptable salt thereof to the subject in an ON: OFF schedule.

33. The method of count 32, comprising administering dovitinib or the pharmaceutically acceptable salt thereof to the subject in a five days ON: two days OFF schedule.

34. The method of any one of counts 3 and 10-33, comprising administering a second dose of dovitinib or the pharmaceutically acceptable salt thereof to the subject two days, four days, six days, one week, two weeks, three weeks, four weeks, or five weeks after administration of a first dose of dovitinib or the pharmaceutically acceptable salt thereof.

35. The method of any one of counts 3 and 10-34, wherein dovitinib or the pharmaceutically acceptable salt thereof is administered in a dosage form.

36. The method of count 35, wherein dovitinib or the pharmaceutically acceptable salt thereof is administered to the subject at a dose of about 5-5000 mg.

37. The method of count 36, wherein dovitinib or the pharmaceutically acceptable salt thereof is administered to the subject at a dose of about 10 mg, 50 mg, or 200 mg.

38. The method of count 36, wherein dovitinib or the pharmaceutically acceptable salt thereof is administered to the subject at a dose of about 50-800 mg.

39. The method of count 38, wherein dovitinib or the pharmaceutically acceptable salt thereof is administered to the subject at a dose of about 500 mg.

40. The method of count 39, wherein dovitinib or the pharmaceutically acceptable salt thereof is administered to the subject at a dose of about 500 mg once daily.

41. The method of count 40, wherein dovitinib or the pharmaceutically acceptable salt thereof is administered to the subject at a dose of about 500 mg once daily for five days.

42. The method of count 41, wherein dovitinib or the pharmaceutically acceptable salt thereof is administered to the subject at a dose of about 500 mg once daily in a five days ON: two days OFF schedule.

43. The method of any one of counts 3 and 10-42, wherein the contacting step (a) and the measuring step (b) occur prior to, concurrent to, or after administration of dovitinib or the pharmaceutically acceptable salt thereof to the subject.

44. The method of any one of counts 3 and 10-43, wherein the contacting step (a) and/or the measuring step (b) occur multiple times.

45. The method of any one of counts 1-44, wherein the device is a microarray.

46. The method of count 45, wherein the microarray is a deoxyribonucleic acid (DNA)-based platform.

47. The method of any one of counts 1-46, wherein the device comprises at least two, at least three, at least four, at least five, at least six, at least seven, at least eight, at least nine, at least ten, or more single-stranded nucleic acid molecules of (i) and/or (ii).

48. The method of any one of counts 1-47, wherein the one or more single-stranded nucleic acid molecules of the device have a length in the range of 10-100 nucleotides.

49. The method of count 48, wherein the one or more single-stranded nucleic acid molecules have a length in the range of 20-60 nucleotides.

50. The method of any one of counts 1-49, wherein the method comprises converting the level of expression of the one or more biomarkers of sensitivity and/or the one or more biomarkers of resistance into a mean score, wherein the mean score indicates the responsiveness of the subject to dovitinib or a pharmaceutically acceptable salt thereof.

51. The method of count 50, further comprising subtracting the mean score for the one or more biomarkers of resistance from the mean score for the one or more biomarkers of sensitivity to obtain a difference score, wherein the difference score indicates the responsiveness of the subject to dovitinib or a pharmaceutically acceptable salt thereof.

52. The method of count 50 or 51, wherein the mean score and/or the difference score above a cutoff value indicates that the subject is responsive to dovitinib or a pharmaceutically acceptable salt thereof.

53. The method of count 52, wherein the cutoff value is established as the $50^{th}$ percentile, or 60th percentile, or $70^{th}$ percentile, or $80^{th}$ percentile, or $90^{th}$ percentile or greater in a reference population, such as a sample(s) from a tumor of the same type as that of the subject.

54. The method of any one of counts 1-53, wherein the level of expression of the one or more biomarkers of sensitivity and/or the one or more biomarkers of resistance is determined by microarray analysis or nucleic acid amplification methods.

55. The method of count 54, wherein the nucleic acid amplification method is reverse transcription quantitative real-time polymerase chain reaction (RT-qPCR).

56. The method of any one of counts 1-55, wherein:
(i) the level of expression of the biomarkers of sensitivity is determined by detecting the level of mRNA transcribed from a gene coding one or more of the biomarkers of Table 2; and/or
(ii) the level of expression of the biomarkers of resistance is determined by detecting the level of mRNA transcribed from a gene coding one or more of the biomarkers of Table 3.

57. The method of any one of counts 1-56, wherein the biomarkers of sensitivity are selected from:
(a) one or more of SEQ ID NOs: 1-15; and/or
(b) one or more of SEQ ID NOs: 16-30.

58. The method of any one of counts 1-57, wherein the biomarkers of resistance are selected from:
(a) one or more of SEQ ID NOs: 31-45; and/or
(b) one or more of SEQ ID NOs: 46-58.

59. The method of any one of counts 1-58, wherein:
(i) the biomarkers of sensitivity are selected from at least 5, at least 10, at least 15, at least 20, at least 25, or at least 27 of the biomarkers of Table 2; and/or
(ii) the biomarkers of resistance are selected from at least 5, at least 10, at least 15, at least 20, at least 25, or at least 27 of the biomarkers of Table 3.

60. The method of any one of counts 1-59, wherein:
(i) the biomarker of sensitivity is DDIT4 (SEQ ID NO: 1); and/or
(ii) the biomarker of resistance is SCAMPS (SEQ ID NO: 31).

61. The method of any one of counts 1-60, wherein the cancer is selected from a solid tumor cancer and a hematological cancer.

62. The method of any one of counts 1-61, wherein the cancer is selected from the group consisting of:
multiple myeloma, breast cancer, acute myelogenous leukemia (AML), acute lympho-blastic leukemia (ALL), chronic lymphocytic leukemia (CLL), myelodysplastic syndrome (MDS), chronic myelogenous leukemia—chronic phase (CMLCP), diffuse large B-cell lymphoma (DLBCL), cutaneous T-cell lymphoma (CTCL), peripheral T-cell lymphoma (PTCL), Hodgkin's lymphoma, hepatocellular carcinoma (HCC), cervical cancer, prostate cancer, kidney cancer, renal cell carcinoma (RCC), esophageal cancer, melanoma, glioma, pancreatic cancer, ovarian cancer, gastrointestinal stromal tumors (GIST), sarcoma, breast cancer, estrogen receptor-positive (ERpos) breast cancer, metastatic breast cancer, endometrial cancer, lung cancer, non-small cell lung carcinoma (NSCLC), mesothelioma, intestinal cancer, colon cancer, bladder cancer, adrenal cancer, gallbladder cancer, and squamous cell carcinoma of the head and neck (SCCHN).

63. The method of count 62, wherein the cancer is breast cancer.

64. The method of count 63, wherein the breast cancer is estrogen receptor-positive (ER pos) breast cancer or is a metastatic form of breast cancer.

65. The method of count 62, wherein the cancer is endometrial cancer.

66. The method of count 62, wherein the cancer is renal cell carcinoma (RCC).

67. The method of count 62, wherein the cancer is hepatocellular carcinoma (HCC).

68. The method of count 62, wherein the cancer is gastrointestinal stromal tumor (GIST).

69. The method of count 62, wherein the cancer is lung cancer.

70. The method of any one of counts 1-69, wherein the subject has recurrence of cancer.

71. The method of any one of counts 1-70, wherein the sample from the subject is a tumor sample.

The following examples are intended to illustrate, rather than limit, the invention.

EXAMPLES

Example 1. Identification of Biomarkers of Sensitivity and Resistance to Dovitinib The drug dovitinib was submitted to NCI for testing in their NCI60 panel of cell lines. The measured growth inhibition, expressed as −log(GI50) values for cell lines in the panel, are as shown in Table 1:

TABLE 1

| Measured growth inhibition by dovitinib in NCI60 panel. | |
|---|---|
| Cell line | −log($GI_{50}$) |
| CCRF-CEM | 6.23 |
| HL-60(TB) | 5.97 |
| K-562 | 6.26 |
| MOLT-4 | 6.48 |
| RPMI-8226 | 5.83 |
| SR | 6.35 |

TABLE 1-continued

Measured growth inhibition by dovitinib in NCI60 panel.

| Cell line | $-\log(GI_{50})$ |
|---|---|
| A549/ATCC | 6.25 |
| EKVX | 5.12 |
| HOP-62 | 5.84 |
| HOP-92 | 6.45 |
| NCI-H226 | 6.45 |
| NCI-H23 | 5.61 |
| NCI-H322M | 6.12 |
| NCI-H460 | 6.33 |
| NCI-H522 | 5.5 |
| COLO 205 | 5.65 |
| HCC-2998 | 5.88 |
| HCT-116 | 6.38 |
| HCT-15 | 6.37 |
| HT29 | 5.85 |
| KM12 | 7.38 |
| SW-620 | 6.26 |
| SF-268 | 5.66 |
| SF-295 | 5.22 |
| SF-539 | 6.37 |
| SNB-19 | 5.58 |
| SNB-75 | 6.01 |
| U251 | 6.26 |
| LOX IMVI | 6.06 |
| MALME-3M | 6.31 |
| M14 | 6.41 |
| MDA-MB-435 | 5.97 |
| SK-MEL-2 | 6.05 |
| SK-MEL-28 | 5.83 |
| SK-MEL-5 | 5.75 |
| UACC-257 | 5.47 |
| UACC-62 | 5.44 |
| IGROV1 | 6.6 |
| OVCAR-3 | 5.17 |
| OVCAR-4 | 6.24 |
| OVCAR-5 | 5.75 |
| OVCAR-8 | 5.84 |
| NCI/ADR-RES | 5.57 |
| SK-OV-3 | 6.29 |
| 786-0 | 6.14 |
| A498 | 6.87 |
| ACHN | 6.48 |
| CAKI-1 | 6.33 |
| RXF 393 | 6.66 |
| SN12C | 6.17 |
| TK-10 | 5.11 |
| UO-31 | 6.66 |
| PC-3 | 5.95 |
| DU-145 | 5.94 |
| MCF7 | 5.93 |
| MDA-MB-231/ATCC | 5.63 |
| HS 578T | 6.01 |
| BT-549 | 5.98 |
| T-47D | 5 |
| MDA-MB-468 | 5.59 |

Baseline DNA chip measurements of 61 of the cancer cell lines in Table 1 (excluding M14 HEC-1 ECC-1 SNG-II HEC-88nu SR IM-9 Namalwa MC/CAR U266 JVM-13 NCEB-1 ARH-77) were performed using Affymetrix HG-U133Plus2 arrays and logit normalized. For each array, the logit transformation was performed followed by a Z-transformation to mean zero and SD 1, and correlated to growth inhibition ($-\log(GI50)$). The expression level of each of the genes of Tables 2 and 3 in each cell line was correlated to the growth of those cell lines ($\log(GI50)$) in the presence of dovitinib. The Pearson correlation coefficient was then determined to identify genes positively and negatively correlated to sensitivity to dovitinib. Tables 2 and 3 show the top positively correlated genes (the biomarkers of sensitivity) and negatively correlated genes (the biomarkers of resistance). In particular, genes with a Pearson correlation greater than 0.25 or below −0.25 can be classified as biomarkers of sensitivity or resistance, respectively.

Example 2. Dovitinib Versus Sorafenib for Third-Line Targeted Treatment of Patients with Metastatic Renal Cell Carcinoma: An Open-Label, Randomized Phase 3 Trial (ClinicalTrials.gov, Number NCT01223027)

Gene expression data (Affymetrix) and clinical response data was obtained from 73 patients in the dovitinib arm. The DRP was applied to calculate a score for each patient (mean of genes in Table 2 minus mean of genes in Table 3). The score for each patient was compared to a reference population with the same diagnosis. For the reference population the dovitinib and sorafenib arms were combined (N=148). This allowed the calculation of a percentile score for each patient. Patients were grouped according to RECIST v1.1 response (centrally assessed) and included in FIG. 1. As is seen in FIG. 1, the higher the percentile score of a patient, the higher is the predicted likelihood of response to the treatment.

Example 3. Dovitinib in Patients with Gastrointestinal Stromal Tumor Refractory and/or Intolerant to Imatinib (ClinicalTrials.gov Identifier: NCT01478373)

Gene expression data (Affymetrix) and clinical response data was obtained from 14 patients. The DRP was applied to calculate a score for each patient (mean of genes in Table 2 minus mean of genes in Table 3). The score for each patient was compared to a reference population with the same diagnosis. For the reference population public data sets were downloaded from the GEO database (GSE20708, GSE17743, GSE8167, N=83). This allowed the calculation of a percentile score for each patient. Patients were grouped according to RECIST v1.1 response (locally assessed, no central assessment) and included in FIG. 1. As is seen in FIG. 1, the higher the percentile score of a patient, the higher is the predicted likelihood of response to the treatment.

Example 4. Second-Line Dovitinib (TKI258) in Patients with FGFR2-Mutated or FGFR2-Non-Mutated Advanced or Metastatic Endometrial Cancer: A Non-Randomised, Open-Label, Two-Group, Two-Stage, Phase 2 Study (ClinicalTrials.gov Identifier: NCT01379534)

Gene expression data (Affymetrix) and clinical response data was obtained from 29 patients. The DRP was applied to calculate a score for each patient (mean of genes in Table 2 minus mean of genes in Table 3). The score for each patient was compared to a reference population with the same diagnosis. For the reference population a public data set was downloaded from the GEO database (GSE17025, N=91). This allowed the calculation of a percentile score for each patient. Patients were grouped according to RECIST v1.1 response (central assessment) and included in FIG. 1. As is seen in FIG. 1, the higher the percentile score of a patient, the higher is the predicted likelihood of response to the treatment.

Example 5. Randomized, Open-Label Phase 2 Study Comparing Frontline Dovitinib Versus Sorafenib in Patients with Advanced Hepatocellular Carcinoma (ClinicalTrials.gov Identifier: NCT01232296)

Gene expression data (Affymetrix) and clinical response data was obtained from 6 patients in the dovitinib arm. The DRP was applied to calculate a score for each patient (mean of genes in Table 2 minus mean of genes in Table 3). The score for each patient was compared to a reference population with the same diagnosis. For the reference population the sorafenib+dovitinib arms were combined (N=18) and a public data set was downloaded from the GEO database (GSE6222, N=13). This allowed the calculation of a percentile score for each patient. Patients were grouped according to RECIST v1.1 response (modified central assessment) and included in FIG. 1. As is seen in FIG. 1, the higher the percentile score of a patient, the higher is the predicted likelihood of response to the treatment.

Example 6. Phase II, Randomized, Placebo-Controlled Study of Dovitinib in Combination with Fulvestrant in Postmenopausal Patients with HR+, HER2− Breast Cancer that had Progressed During or after Prior Endocrine Therapy (ClinicalTrials.gov Identifier: NCT01528345)

Gene expression data (Affymetrix) and clinical response data was obtained from 19 patients in the dovitinib plus fulvestrant arm. The DRP was applied to calculate a score for each patient (mean of genes in Table 2 minus mean of genes in Table 3). The score for each patient was compared to a reference population with the same diagnosis. For the reference population 819 breast cancer patients screened for a LiPlaCis trial in Denmark were used (ClinicalTrials.gov Identifier: NCT01861496). That allowed the calculation of a percentile score for each patient. Patients were grouped according to RECIST v1.1 response (local assessment, no central assessment performed) and included in FIG. 1. As is seen in FIG. 1, the higher the percentile score of a patient, the higher is the predicted likelihood of response to the treatment.

Example 7. Predicting Response Rate as a Function of DRP Cutoff

Figure 2:
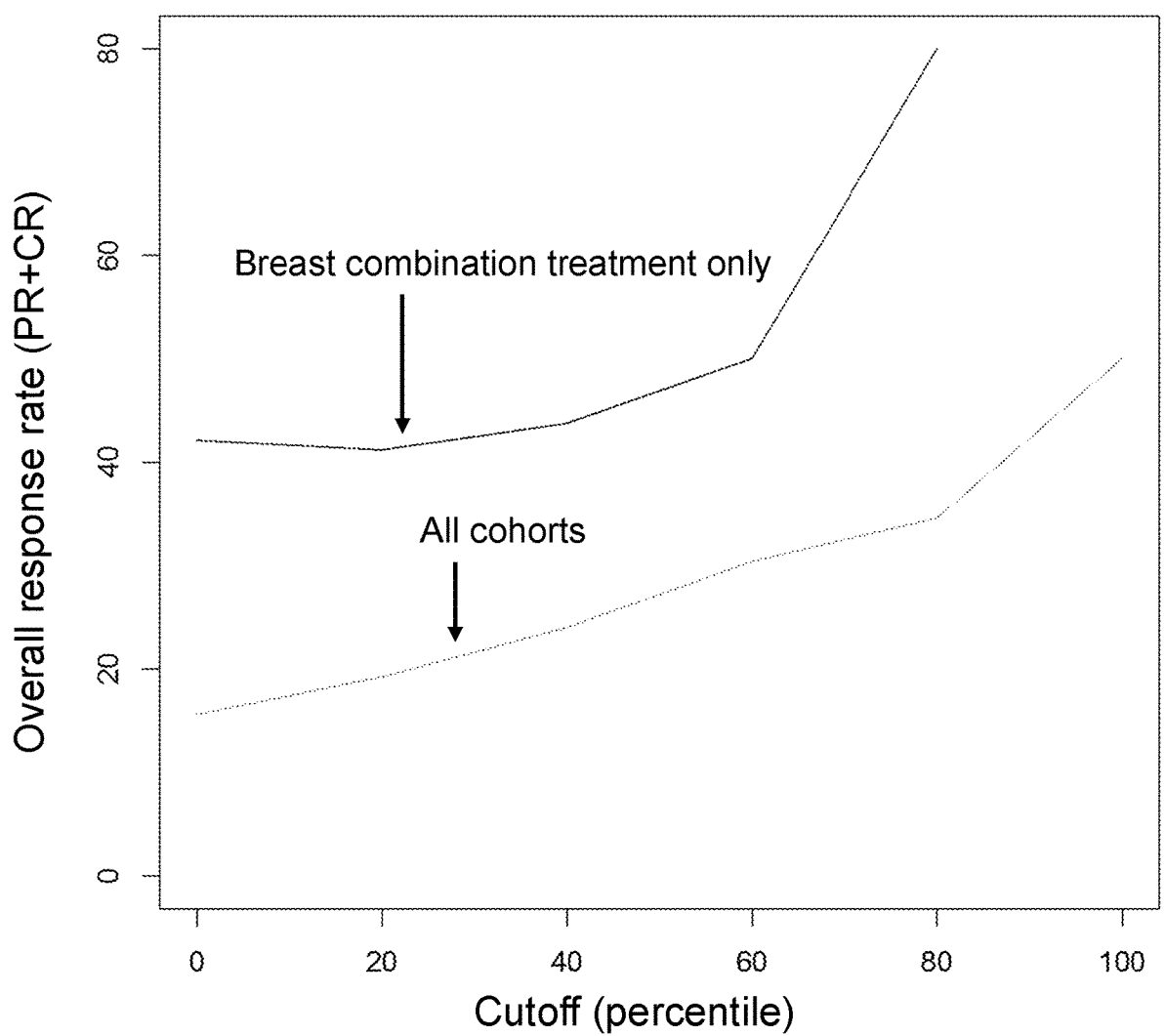
FIG. 2 is a graph showing response rate as a function of DRP score cutoff.

As shown in FIG. 2, the response rate depends on the cutoff applied to the DRP scores demonstrated in FIG. 1; the higher the cutoff, the higher the predicted likelihood of and the rate of response to the treatment. Using FIG. 2 as a guide, it is evident that the dovitinib DRP biomarker can substantially increase the response rate in a selected subset of patients in any cancer type. For all the five cohorts from Examples 2-6 (curve marked as "All cohorts"), the average overall response rate (ORR=CR+PR) without the DRP is 16%. At a cutoff of 50, the ORR is 26%. At a cutoff of 80, the ORR is 35%. For combination treatment, however, the response rate can be much higher. The curve marked as "Breast combination treatment only" shows the response rate in dovitinib+fulvestrant combination therapy in breast cancer. It reaches 80% with a cutoff of 80.

Example 8. Predicting Responsiveness of Breast Cancer Patients to Dovitinib

The diagnostic methods described herein can be used to predict the responsiveness of a breast cancer patient to treatment with dovitinib or a pharmaceutically acceptable salt thereof. In particular, the breast cancer patient may be one that has not previously received any cancer treatment or one that has received a cancer treatment other than dovitinib or a pharmaceutically acceptable salt thereof. Moreover, the patient may be one diagnosed with breast cancer or with recurrence of breast cancer.

A biological sample (e.g., a breast tissue sample, such as a breast tissue sample obtained by biopsy) may be obtained from the patient through methods well known in the art. The sample may be frozen and/or prepared, e.g., by formalin fixation and paraffin embedding. In particular, mRNA can be isolated from the sample and a gene expression profile can be determined, e.g., using a microarray platform, such as the Affymetrix HG-U133A, for one or more of the biomarkers shown in Table(s) 2 and/or 3. One or more of the biomarkers shown in Table(s) 2 and/or 3 can also be measured, e.g., by sequencing or PCR-based techniques, such as those described herein.

For example, the expression level of one or more biomarkers of sensitivity to dovitinib or a pharmaceutically acceptable salt thereof can be determined in the sample from the patient, such as one or more biomarkers of SEQ ID NO: 1, SEQ ID NOs: 1-5, SEQ ID NOs: 1-10, SEQ ID NOs: 1-15, SEQ ID NOs: 1-20, or SEQ ID NOs: 1-25. In particular, the biomarker is DDIT4 (SEQ ID NO: 1). The expression level of one or more biomarkers of resistance to dovitinib can also be determined in the sample from the patient, such as one or more of SEQ ID NO: 31, SEQ ID NOs: 31-35, SEQ ID NOs: 31-40; SEQ ID NOs: 31-45; SEQ ID NOs: 31-50; or SEQ ID NOs: 31-55. In particular, the biomarker is SCAMP5 (SEQ ID NO: 31). The patient's responsiveness to dovitinib or a pharmaceutically acceptable salt thereof can also be assessed by calculating a difference score for the patient (mean of expression of the biomarkers of sensitivity noted above minus the mean of expression of the biomarkers of resistance noted above).

The breast cancer patient would be determined to be responsive to dovitinib or a pharmaceutically acceptable salt thereof when the expression level of the one or more biomarkers of sensitivity is similar to (e.g., substantially similar to) the expression level of the biomarkers of sensitivity in a cell or tissue known to be sensitive to dovitinib or a pharmaceutically acceptable salt thereof. The breast cancer patient would also be determined to be responsive to dovitinib or a pharmaceutically acceptable salt thereof when the expression level of one or more of the biomarkers of resistance is similar to (e.g., substantially similar to) the expression level of the biomarkers of resistance in a cell or tissue known to be sensitive to dovitinib or a pharmaceutically acceptable salt thereof. The breast cancer patient would also be determined to be responsive to dovitinib or a pharmaceutically acceptable salt thereof when difference score for the patient is similar to (e.g., substantially similar to) the difference score in a cell or tissue known to be sensitive to dovitinib or a pharmaceutically acceptable salt thereof (e.g., the difference score of a reference subject having the same diagnosis as the patient that is already determined to be responsive to dovitinib or a pharmaceutically acceptable salt thereof).

Alternatively, the breast cancer patient may be determined to be responsive to dovitinib or a pharmaceutically acceptable salt thereof if the expression level of one or more of the biomarkers of sensitivity is dissimilar to (e.g., substantially dissimilar to) the expression level of the biomarkers of sensitivity in a cell or tissue known to be resistant to dovitinib or a pharmaceutically acceptable salt thereof. The breast cancer patient may also be responsive to dovitinib or a pharmaceutically acceptable salt thereof if the expression level of one or more of the biomarkers of resistance is dissimilar to (e.g., substantially dissimilar to) the expression level of the biomarkers of resistance in a cell or tissue known to be resistant to dovitinib or a pharmaceutically acceptable salt thereof. The breast cancer patient would also be determined to be responsive to dovitinib or a pharmaceutically acceptable salt thereof when difference score for the patient is dissimilar to (e.g., substantially dissimilar to) the difference score in a cell or tissue known to be resistant to dovitinib or a pharmaceutically acceptable salt thereof (e.g., the difference score of a reference subject having the same diagnosis as the patient that is already determined to be resistant to dovitinib or a pharmaceutically acceptable salt thereof).

If the patient is predicted to be responsive, then the patient can be administered dovitinib or a pharmaceutically acceptable salt thereof, such as dovitinib or a pharmaceutically acceptable salt thereof administered orally at a dose of about 5-5000 mg (e.g., about 50-800 mg). Conversely, if the patient is predicted to be non-responsive to dovitinib (e.g., dovitinib or a pharmaceutically acceptable salt thereof) treatment, then the patient can be administered one or more therapies other than dovitinib or a pharmaceutically acceptable salt thereof, such as radiation or a therapeutic agent (e.g., doxorubicin, epirubicin, paclitaxel, docetaxel, 5-fluorouracil (5-FU), cyclophosphamide, carboplatin, cisplatin, vinorelbine, gemcitabine, mitoxantrone, ixabepilone, eribulin, irinotecan, capecitabine, tegafur, oxaliplatin, and/or another therapeutic agent described herein).

Example 9. Predicting Responsiveness of Endometrial Cancer Patients to Dovitinib The diagnostic methods of the present invention can be used to predict the responsiveness of an endometrial cancer patient to treatment with dovitinib or a pharmaceutically acceptable salt thereof. In particular, the endometrial cancer patient may be one that has not previously received any cancer treatment or one that has received a cancer treatment other than dovitinib or a pharmaceutically acceptable salt thereof. Moreover, the patient may be one diagnosed with endometrial cancer or with recurrence of endometrial cancer.

A biological sample (e.g., an ovarian tissue sample, such as an endometrial tissue sample obtained by biopsy) may be obtained from the patient through methods well known in the art. The sample may be frozen and/or prepared, e.g., by formalin fixation and paraffin embedding. In particular, mRNA can be isolated from the sample and a gene expression profile can be determined, e.g., using a microarray platform, such as the Affymetrix HG-U133A, for one or more of the biomarkers shown in Table(s) 2 and/or 3. One or more of the biomarkers shown in Table(s) 2 and/or 3 can also be measured, e.g., by sequencing or PCR-based techniques, such as those described herein.

For example, the expression level of one or more biomarkers of sensitivity to dovitinib or a pharmaceutically acceptable salt thereof can be determined in the sample from the patient, such as one or more biomarkers of SEQ ID NO: 1, SEQ ID NOs: 1-5, SEQ ID NOs: 1-10, SEQ ID NOs: 1-15, SEQ ID NOs: 1-20, or SEQ ID NOs: 1-25. In particular, the biomarker is DDIT4 (SEQ ID NO: 1). The expression level of one or more biomarkers of resistance to dovitinib can also be determined in the sample from the patient, such as one or more of SEQ ID NO: 31, SEQ ID NOs: 31-35, SEQ ID NOs: 31-40; SEQ ID NOs: 31-45; SEQ ID NOs: 31-50; or SEQ ID NOs: 31-55. In particular, the biomarker is SCAMPS (SEQ ID NO: 31). The patient's responsiveness to dovitinib or a pharmaceutically acceptable salt thereof can also be assessed by calculating a difference score for the patient (mean of expression of the biomarkers of sensitivity noted above minus the mean of expression of the biomarkers of resistance noted above).

The endometrial cancer patient would be determined to be responsive to dovitinib or a pharmaceutically acceptable salt thereof when the expression level of the one or more biomarkers of sensitivity is similar to (e.g., substantially similar to) the expression level of the biomarkers of sensitivity in a cell or tissue known to be sensitive to dovitinib or a pharmaceutically acceptable salt thereof. The endometrial cancer patient would also be determined to be responsive to dovitinib or a pharmaceutically acceptable salt thereof when the expression level of one or more of the biomarkers of resistance is similar to (e.g., substantially similar to) the expression level of the biomarkers of resistance in a cell or tissue known to be sensitive to dovitinib or a pharmaceutically acceptable salt thereof. The endometrial cancer cancer patient would also be determined to be responsive to dovitinib or a pharmaceutically acceptable salt thereof when difference score for the patient is similar to (e.g., substantially similar to) the difference score in a cell or tissue known to be sensitive to dovitinib or a pharmaceutically acceptable salt thereof (e.g., the difference score of a reference subject having the same diagnosis as the patient that is already determined to be responsive to dovitinib or a pharmaceutically acceptable salt thereof).

Alternatively, the endometrial cancer patient would be determined to responsive to dovitinib or a pharmaceutically acceptable salt thereof when the expression level of one or more of the biomarkers of sensitivity is dissimilar to (e.g., substantially dissimilar to) the expression level of the biomarkers of sensitivity in a cell or tissue known to be resistant to dovitinib or a pharmaceutically acceptable salt thereof. The endometrial cancer patient would also be determined to be responsive to dovitinib or a pharmaceutically acceptable salt thereof when the expression level of one or more of the biomarkers of resistance is dissimilar to (e.g., substantially dissimilar to) the expression level of the biomarkers of resistance in a cell or tissue known to be resistant to dovitinib or a pharmaceutically acceptable salt thereof. The endometrial cancer cancer patient would also be determined to be responsive to dovitinib or a pharmaceutically acceptable salt thereof when difference score for the patient is dissimilar to (e.g., substantially dissimilar to) the difference score in a cell or tissue known to be resistant to dovitinib or a pharmaceutically acceptable salt thereof (e.g., the difference score of a reference subject having the same diagnosis as the patient that is already determined to be resistant to dovitinib or a pharmaceutically acceptable salt thereof).

If the patient is predicted to be responsive, then the patient can be administered dovitinib or a pharmaceutically acceptable salt thereof, such as dovitinib or a pharmaceutically acceptable salt thereof administered orally at a dose of about 5-5000 mg (e.g., about 50-800 mg, such as about 500 mg). Conversely, if the patient is predicted to be non-responsive to dovitinib (e.g., dovitinib or a pharmaceutically acceptable salt thereof) treatment, then the patient can be administered one or more therapies other than dovitinib or a pharmaceutically acceptable salt thereof, such as radiation or a therapeutic agent (e.g., carboplatin, cisplatin, docetaxel, paclitaxel, and/or other therapeutic agents described herein).

Example 10. Treating a Cancer Patient with Dovitinib

Cancer patients (e.g., those diagnosed with breast cancer, endometrial cancer, RCC, HCC, GIST, or lung cancer) can be treated with dovitinib or a pharmaceutically acceptable salt thereof after being predicted to be responsive to treatment with dovitinib or a pharmaceutically acceptable salt thereof by the methods described herein. In particular, the cancer patient may be one that has not previously received any cancer treatment or one that has received a cancer treatment other than dovitinib or a pharmaceutically acceptable salt thereof. Moreover, the patient may be one diagnosed with a cancer (e.g., breast cancer, endometrial cancer, RCC, HCC, GIST, or lung cancer) or with recurrence thereof.

The cancer patient can be determined to be responsive to dovitinib or a pharmaceutically acceptable salt thereof following the methods exemplified in the aforementioned Examples 8 and 9. Once the patient has been determined to be responsive to dovitinib or a pharmaceutically acceptable salt thereof, according to the methods described herein, dovitinib or a pharmaceutically acceptable salt thereof may be administered to the patient, for example, orally as a daily dose of 500 mg (e.g., the patient can be administered a hard gelatin capsule or a film coated tablet containing 500 mg of dovitinib or a pharmaceutically acceptable salt thereof). Alternative dosing regimens and forms of dovitinib or a pharmaceutically acceptable salt thereof (e.g., hard gelatin capsules of 10 mg, 50 mg, 100 mg, 200 mg, 250 mg, or 500 mg, such as hard gelatin capsules of 100 mg (e.g., 5×100 mg hard gelatin capsules daily)) or film coated tablets (e.g., film coated tablets of 10 mg, 50 mg, 100 mg, 200 mg, 250 mg, or 500 mg, such as film coated tablets of 250 mg (e.g., 2×250 mg film coated tablets daily)) can also be administered. Dovitinib or a pharmaceutically acceptable salt thereof may be administered to the patient alone or in combination with an additional therapy, such as a PD1 or PDL1 inhibitor, an aromatase inhibitor, and/or a fulvestrant, which can be administered prior to, concurrently with, or after administration of dovitinib or the pharmaceutically acceptable salt thereof.

Dovitinib or a pharmaceutically acceptable salt thereof may be administered to the patient one or more times during a first treatment regimen (e.g., one or more times daily for up to six days or more, such as once daily for five days). Dovitinib or a pharmaceutically acceptable salt thereof may be administered to the patient in an ON: OFF schedule, such as a one-ten days ON: one-ten days OFF schedule (e.g., a five days ON: two days OFF schedule). The patient can be administered a second treatment regimen of dovitinib or a pharmaceutically acceptable salt thereof two days, four days, six days, one week, two weeks, three weeks, four weeks, or five weeks after administration of the first treatment regimen of dovitinib or a pharmaceutically acceptable salt thereof. The administration of dovitinib or a pharmaceutically acceptable salt thereof can be repeated at such a frequency for a certain period of time, followed by a period without treatment. Such repeated administrations can occur over a course of therapy lasting a specified length of time (e.g., at least 1 week, 2 weeks, 3 weeks, 1 month, 2 months, 3 months, 6 months, or 1 year or more).

Example 11. Combining Dovitinib with an Immune Checkpoint Inhibitor

Figure 3:
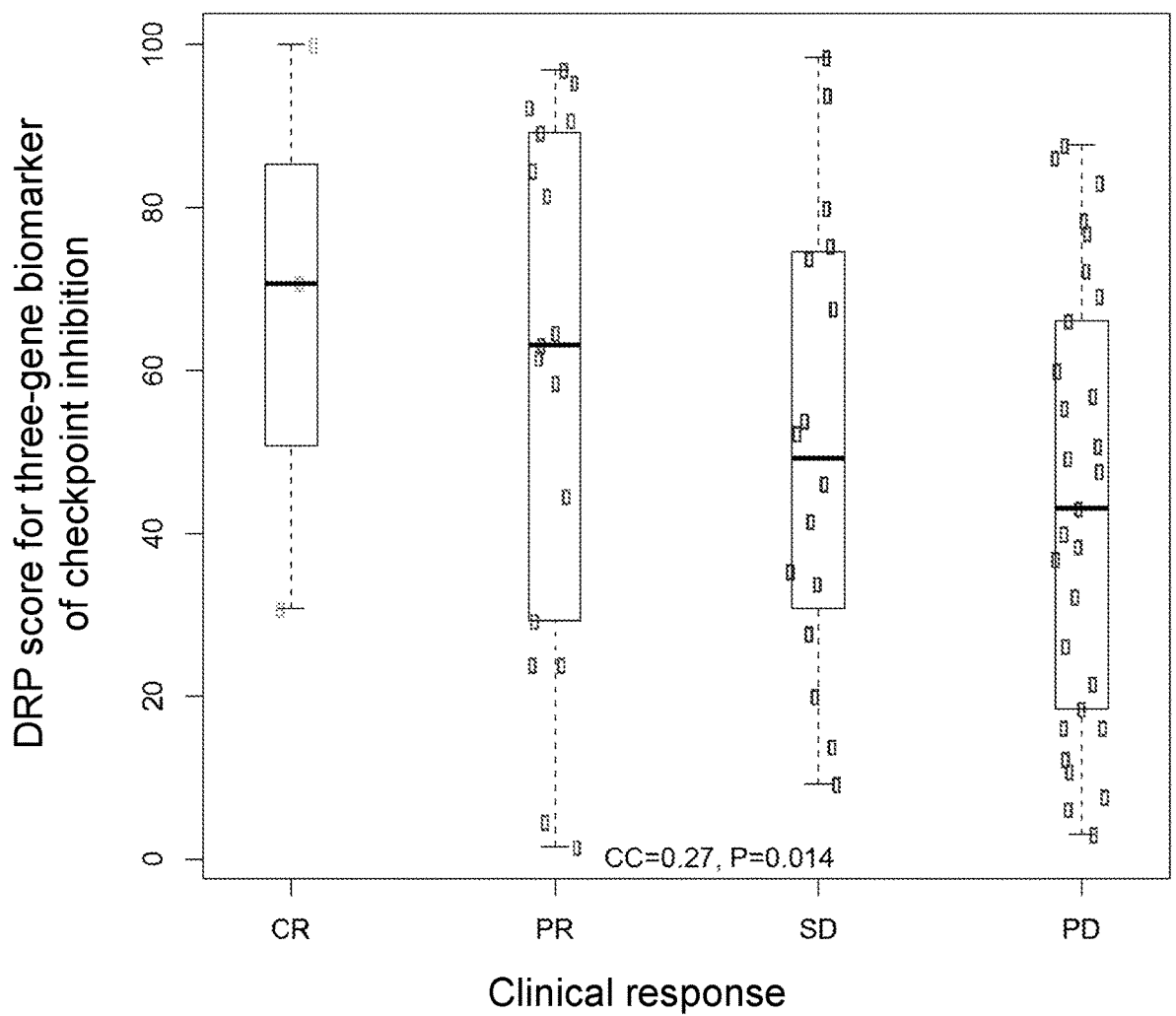
FIG. 3 is a graph showing correlation between DRP score of a three-gene biomarker of checkpoint inhibition and clinical response of 65 solid tumors (including, e.g., non-small cell lung carcinoma, head and neck squamous cell carcinoma, and melanoma) to the PD-1 inhibitors, Pembrolizumab and Nivolumab. A Pearson correlation between percentile score and clinical response (complete remission (CR)=1, partial response (PR)=2, stable disease (SD)=3, progressive disease (PD)=4, non-CR/non-PD=3, central evaluation without confirmation, where available) is −0.27, P=0.014 one sided. The horizontal line shows a cutoff of 50.

Biomarkers for checkpoint inhibitors, such as, e.g., PD-1, PD-L1, CTLA-4, FAS receptor, apoptosis, and T-cell killing via granzyme and perforin, can be used to determine a subject's responsiveness to treatment with an immune checkpoint inhibitor. FIG. 3 shows how a mean of the expression of PD-1, PD-L1, and FAS receptor in the tumor of each patient (solid tumors from 65 patients were tested) can be correlated to sensitivity to a checkpoint inhibitor (nivolumab and pembrolizumab were tested in the patients). In this example, clinical and NanoString expression data were obtained from Prat et al. (*Cancer Res.* 77:3540-3550, 2017), which used tumor samples from subjects with non-small cell lung carcinoma, head and neck squamous cell carcinoma, and melanoma. The higher the percentile score of a patient whose sample is tested for the level of these biomarkers, relative to the percentile shown in FIG. 3, the higher is the predicted likelihood of response to treatment with an immune checkpoint inhibitor.

As is shown in FIG. 3, the three-gene biomarker of checkpoint inhibition, which includes an average of expression level of the genes listed in Table 4 (e.g., PD-1 (e.g., SEQ ID NO: 59), PD-L1 (e.g., SEQ ID NO: 60), and FAS (e.g., SEQ ID NO: 61)) can be used to predict the likelihood that a test subject (e.g., a tumor sample from the test subject can be used) will be responsive to one or more immune checkpoint inhibitors. When determining the average expression level of the genes of Table 4, the FAS gene should not be given more weight than the PD-1 and PD-L1 genes. Therefore, e.g., if using an Affymetrix array, which may contain multiple FAS gene probes in the probeset, the expression of the FAS genes (such as those listed in Table 4) should be averaged before combining the number with the PD-1 and PD-L1 probesets. The higher the percentile score of the test subject whose sample is tested for the level of these biomarkers, relative to the percentile shown in FIG. 3, the higher is the predicted likelihood of response to treatment with an immune checkpoint inhibitor.

When predicting responsiveness to combination therapy with dovitinib (or a pharmaceutically acceptable salt thereof) and an immune checkpoint inhibitor (e.g., a PD-1 inhibitor, a PD-L1 inhibitor, or a CTLA-4 inhibitor), the dovitinib DRP and the three-gene biomarker of checkpoint inhibition can be given equal weight, for example by taking their average after normalization to a scale from zero to 100.

TABLE 4

Three-gene biomarker of checkpoint inhibition

| Gene | Synonyms | Affy ID | Representative probe sequence | SEQ ID NO: |
|---|---|---|---|---|
| PD-1 | CD279, PDCD1 | 207634_at | GAGGCAGTAAGCGGGCAGGCAGAGC | 59 |
| PD-L1 | CD274 | 223834_at | TGGTTTAGGGGTTCATCGGGGCTGA | 60 |
| FAS | CD95, TNFRSF6 | 215719_x_at, 216252_x_at, 204780_s_at, 204781_s_at" | ACCAAGGTTCTCATGAATCTCCAAC | 61 |

OTHER EMBODIMENTS

All publications, patents, and patent applications mentioned in the above specification are hereby incorporated by reference. Various modifications and variations of the described device and methods of use of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention. For example, it is anticipated that measuring the level of proteins, metabolites, identifying genetic mutations and DNA copy number variations, all will be useful in determining patient responsiveness.

The invention claimed is:

1. A method of treating a human subject diagnosed with renal cell carcinoma, gastrointestinal stromal tumor, breast cancer, hepatocellular carcinoma, or endometrial cancer comprising administering dovitinib or a pharmaceutically acceptable salt thereof to the subject, wherein the subject has been determined to be responsive to dovitinib or the pharmaceutically acceptable salt thereof according to a method comprising:
   (a) contacting a tumor sample from the subject comprising nucleic acid molecules with a device comprising:
      (i) single-stranded nucleic acid molecules capable of specifically hybridizing with the nucleotides of DDIT4; and
      (ii) single-stranded nucleic acid molecules capable of specifically hybridizing with the nucleotides of SCAMP3;
   (b) detecting a level of expression of DDIT4 and SCAMP3; and
   (c) calculating a difference score for the subject by subtracting the level of expression of SCAMP3 from the level of expression of DDIT4, wherein the difference score is above a cutoff value of the $50^{th}$ percentile or greater of the difference score in a reference population with the same diagnosis as the subject.

2. The method of claim 1, further comprising administering one or more cancer therapies other than dovitinib or a pharmaceutically acceptable salt thereof to the subject, wherein, optionally, the one or more cancer therapies comprises surgery, radiation, or a therapeutic agent.

3. The method of claim 2, wherein the therapeutic agent is selected from the group consisting of a histone deacetylase (HDAC) inhibitor, an immune checkpoint inhibitor, a cyclin-dependent kinase (CDK) inhibitor, bortezomib, carfilzomib, thalidomide, lenalidomide, pomalidomide, prednisone, dexamethasone, cyclophosphamide, vincristine, doxorubicin, melphalan, capecitabine, tegafur, irinotecan, oxaliplatin, cetuximab, leucovorin, SN-38, everolimus, temsirolimus, bleomycin, lomustine, depsipeptide, carboplatin, erlotinib, gemcitabine, mitoxantrone, cisplatin, busulfan, epirubicin, arsenic trioxide, bendamustine, fulvestrant, teniposide, adriamycin, decitabine, estramustine, etoposide, azaguanine, aclarubicin, mitoxantrone, mitomycin, paclitaxel, taxotere, Irofulven, 5-FU, ara-c, methylprednisolone, methotrexate, methyl-gag, belinostat, carboplatin, idarubicin, IL4-PR38, valproic acid, all-trans retinoic acid (ATRA), cytoxan, topotecan, suberoylanilide hydroxamic acid, leukeran, fludarabine, vinblastine, dacarbazine, hydroxyurea, tegafur, daunorubicin, mechlorethamine, streptozocin, carmustine, mercaptopurine, dactinomycin, tretinoin, ifosfamide, tamoxifen, floxuridine, thioguanine, PSC 833, herceptin, bevacizumab, celecoxib, iressa, anastrozole, letrozole, and rituximab.

4. The method of claim 3, wherein the immune checkpoint inhibitor is a PD1 inhibitor, a PD-L1 inhibitor, or a CTLA-4 inhibitor.

5. The method of claim 1, further comprising determining an expression level of one or more biomarkers of responsiveness to an immune checkpoint inhibitor in a tumor sample from the subject, wherein the one or more biomarkers of responsiveness to an immune checkpoint inhibitor is selected from the group consisting of PD-1, PD-L1, CTLA-4, and FAS receptor.

6. The method of claim 5, wherein the method further comprises administering the immune checkpoint inhibitor to the subject.

7. The method of claim 1, comprising:
   (a) administering dovitinib or the pharmaceutically acceptable salt thereof to the subject two or more times;
   (b) administering dovitinib or the pharmaceutically acceptable salt thereof to the subject one or more times daily, weekly, every two weeks, every three weeks, or monthly;
   (c) administering dovitinib or the pharmaceutically acceptable salt thereof to the subject once daily for five days; or
   (d) administering dovitinib or the pharmaceutically acceptable salt thereof to the subject in an ON: OFF schedule.

8. The method of claim 7, comprising administering dovitinib or the pharmaceutically acceptable salt thereof to the subject in a five days ON: two days OFF schedule.

9. The method of claim 1, wherein dovitinib or the pharmaceutically acceptable salt thereof is administered to the subject:
   (a) at a dose of about 5-5000 mg;
   (b) at a dose of about 10 mg, 50 mg, 200 mg, or 500 mg;
   (c) at a dose of about 50-800 mg;
   (d) at a dose of about 500 mg once daily;
   (e) at a dose of about 500 mg once daily for five days;
   (f) at a dose of about 500 mg once daily in a five days ON: two days OFF schedule.

10. The method of claim 1, wherein the device is a microarray, wherein, optionally, the microarray is a deoxyribonucleic acid (DNA)-based platform.

11. The method of claim 1, wherein:
   (a) the device comprises at least two, at least three, at least four, at least five, at least six, at least seven, at least eight, at least nine, at least ten, or more single-stranded nucleic acid molecules of (i) and/or (ii);
   (b) the one or more single-stranded nucleic acid molecules of the device have a length in the range of 10-100 nucleotides;
   (c) the level of expression of DDIT4 and/or SCAMP3 is determined by microarray analysis or nucleic acid amplification methods.

12. The method of claim 1, wherein:
   (i) the level of expression of DDIT4 is determined by detecting the level of mRNA transcribed from a gene encoding DDIT4; and/or
   (ii) the level of expression of SCAMP3 is determined by detecting the level of mRNA transcribed from a gene encoding SCAMP3.

13. The method of claim 1, wherein the subject has recurrence of the renal cell carcinoma, gastrointestinal stromal tumor, breast cancer, hepatocellular carcinoma, or endometrial cancer.

14. The method of claim 1, wherein the cutoff value is at a $60^{th}$ percentile or greater of the difference score in a reference population with the same diagnosis as the subject.

15. The method of claim 14, wherein the cutoff value is at a $70^{th}$ percentile or greater of the difference score in a reference population with the same diagnosis as the subject.

16. The method of claim 15, wherein the cutoff value is at a $80^{th}$ percentile or greater of the difference score in a reference population with the same diagnosis as the subject.

17. The method of claim 16, wherein the cutoff value is at a $90^{th}$ percentile or greater of the difference score in a reference population with the same diagnosis as the subject.

18. The method of claim 1, wherein the breast cancer is estrogen receptor-positive (ERpos) breast cancer and/or metastatic breast cancer.

19. The method of claim 1, further comprising determining responsiveness of the subject to dovitinib or a pharmaceutically acceptable salt thereof according to steps (a)-(c).

20. A method of treating a human subject diagnosed with renal cell carcinoma, gastrointestinal stromal tumor, breast cancer, hepatocellular carcinoma, or endometrial cancer comprising administering dovitinib or a pharmaceutically acceptable salt thereof to the subject with a difference score determined from a tumor sample from the subject that is above a cutoff value of the $50^{th}$ percentile or greater of the difference score in a reference population with the same diagnosis as the subject, wherein the difference score is the difference between a level of expression of SCAMP3 and a level of expression of DDIT4.

21. The method of claim 20, wherein the cutoff value is at a $60^{th}$ percentile or greater of the difference score in a reference population with the same diagnosis as the subject.

22. The method of claim 21, wherein the cutoff value is at a $70^{th}$ percentile or greater of the difference score in a reference population with the same diagnosis as the subject.

23. The method of claim 22, wherein the cutoff value is at a $80^{th}$ percentile or greater of the difference score in a reference population with the same diagnosis as the subject.

24. The method of claim 23, wherein the cutoff value is at a 90th percentile or greater of the difference score in a reference population with the same diagnosis as the subject.

* * * * *